United States Patent
Andrews et al.

(10) Patent No.: US 9,493,476 B2
(45) Date of Patent: *Nov. 15, 2016

(54) MACROCYCLIC COMPOUNDS AS TRK KINASE INHIBITORS

(71) Applicant: Array BioPharma Inc., Boulder, CO (US)

(72) Inventors: Steven W. Andrews, Boulder, CO (US); Kevin Ronald Condroski, Wallingford, CT (US); Julia Haas, Boulder, CO (US); Yutong Jiang, Boulder, CO (US); Gabrielle R. Kolakowski, Boulder, CO (US); Jeongbeob Seo, Baltimore, MD (US); Hong-Woon Yang, Superior, CO (US); Qian Zhao, Louisville, CO (US)

(73) Assignee: Array BioPharma, Inc., Boulder, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/575,663

(22) Filed: Dec. 18, 2014

(65) Prior Publication Data

US 2015/0336970 A1 Nov. 26, 2015

Related U.S. Application Data

(63) Continuation of application No. 13/698,922, filed as application No. PCT/US2011/036452 on May 13, 2011, now Pat. No. 8,933,084.

(60) Provisional application No. 61/346,767, filed on May 20, 2010, provisional application No. 61/426,716, filed on Dec. 23, 2010.

(51) Int. Cl.
| C07D 487/22 | (2006.01) |
| A61K 31/519 | (2006.01) |
| C07D 487/04 | (2006.01) |
| C07D 519/00 | (2006.01) |
| C07D 471/22 | (2006.01) |
| C07D 498/22 | (2006.01) |

(52) U.S. Cl.
CPC ........... *C07D 487/22* (2013.01); *C07D 471/22* (2013.01); *C07D 487/04* (2013.01); *C07D 498/22* (2013.01); *C07D 519/00* (2013.01)

(58) Field of Classification Search
CPC . C07D 487/22; C07D 471/22; A61K 31/519
See application file for complete search history.

(56) References Cited

U.S. PATENT DOCUMENTS

| 7,491,794 B2 | 2/2009 | Blatt et al. |
| 7,550,470 B2 | 6/2009 | Fraley |
| 8,119,592 B2 | 2/2012 | Beigelman et al. |
| 8,299,021 B2 | 10/2012 | Blatt et al. |
| 8,450,322 B2 | 5/2013 | Andrews et al. |
| 8,513,263 B2 | 8/2013 | Haas et al. |
| 8,791,123 B2 * | 7/2014 | Allen ................... C07D 487/04 514/259.3 |
| 8,865,698 B2 * | 10/2014 | Haas .................... C07D 471/04 514/180 |
| 8,933,084 B2 * | 1/2015 | Andrews ............. C07D 487/04 514/247 |
| 9,127,013 B2 | 9/2015 | Haas et al. |
| 2006/0094699 A1 | 5/2006 | Kampen et al. |
| 2007/0025540 A1 | 2/2007 | Travis |
| 2007/0042941 A1 | 2/2007 | Hirashima et al. |
| 2010/0029633 A1 | 2/2010 | Allen et al. |
| 2011/0166122 A1 | 7/2011 | Andrews et al. |
| 2011/0195948 A1 | 8/2011 | Haas et al. |
| 2013/0203776 A1 | 8/2013 | Andrews et al. |
| 2013/0217662 A1 | 8/2013 | Andrews et al. |
| 2015/0218652 A1 | 8/2015 | Doebele et al. |

FOREIGN PATENT DOCUMENTS

| CN | 1938311 | 3/2007 |
| CN | 101119996 | 2/2008 |
| CN | 101208093 | 6/2008 |

(Continued)

OTHER PUBLICATIONS

American Cancer Society," Sarcoma: Adult Soft Tissue Cancer," Jun. 2014, retrieved on Apr. 27, 2015, http://www.cancer.org/cancer/sarcoma-adultsofttissuecancer/detailedguide/sarcoma-adult-soft-tissue-cancer-key-statistics, 45 pages.

Burns et al., ""Pharmacokinetics (PK) of LOXO-101 During the First-in-Human Phase I Study in Patients with Advanced Solid Tumors,"" Interim Update AACR Annual Meeting, Mar. 2015, Philadelphia, PA., 1 page.

(Continued)

*Primary Examiner* — Golam M M Shameem
(74) *Attorney, Agent, or Firm* — Fish & Richardson P.C.

(57) ABSTRACT

Compounds of Formula I: and pharmaceutically acceptable salts thereof, wherein ring A, ring B, W, m, D, $R^2$, $R^{2a}$, $R^3$, $R^{3a}$, and Z are as defined herein, are inhibitors of Trk kinases and are useful in the treatment of pain, cancer, inflammation, neurodegenerative diseases and certain infectious diseases.

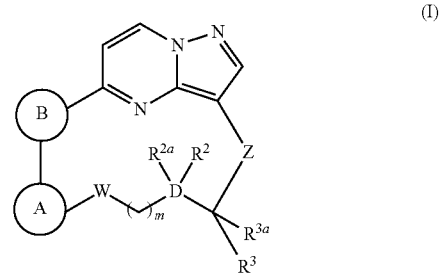

(I)

14 Claims, No Drawings

(56) References Cited

FOREIGN PATENT DOCUMENTS

| | | |
|---|---|---|
| EP | 1873157 | 1/2008 |
| EP | 1948633 | 8/2011 |
| JP | 2004-087707 | 3/2004 |
| JP | 2004-277337 | 10/2004 |
| JP | 2005-008581 | 1/2005 |
| JP | 2007-504276 | 3/2007 |
| JP | 2007-514712 | 6/2007 |
| JP | 2008-523034 | 7/2008 |
| JP | 2008-285464 | 11/2008 |
| JP | 2009-502734 | 1/2009 |
| JP | 2009-511487 | 3/2009 |
| JP | 2009-541242 | 11/2009 |
| JP | 2010-508315 | 3/2010 |
| JP | 2011-520887 | 7/2011 |
| JP | 2012-506446 | 3/2012 |
| JP | 2012-507569 | 3/2012 |
| WO | WO 98/49167 | 11/1998 |
| WO | WO 2004/022561 | 3/2004 |
| WO | WO 2004/052286 | 6/2004 |
| WO | WO 2004/052315 | 6/2004 |
| WO | WO 2004/087707 | 10/2004 |
| WO | WO 2004/089415 | 10/2004 |
| WO | WO 2004/089471 | 10/2004 |
| WO | WO 2005/049033 | 6/2005 |
| WO | WO 2006/087538 | 8/2006 |
| WO | WO 2006/115452 | 11/2006 |
| WO | WO 2007/013673 | 2/2007 |
| WO | WO 2007/015824 | 2/2007 |
| WO | WO 2007/024680 | 3/2007 |
| WO | WO 2007/025090 | 3/2007 |
| WO | WO 2007/025540 | 3/2007 |
| WO | WO 2007/038314 | 4/2007 |
| WO | WO 2007/044410 | 4/2007 |
| WO | WO 2007/044449 | 4/2007 |
| WO | WO 2007/044893 | 4/2007 |
| WO | WO 2007/048066 | 4/2007 |
| WO | WO 2007/062805 | 6/2007 |
| WO | WO 2007/084815 | 7/2007 |
| WO | WO 2007/102679 | 9/2007 |
| WO | WO 2007/113000 | 10/2007 |
| WO | WO 2007/129161 | 11/2007 |
| WO | WO 2008/016131 | 2/2008 |
| WO | WO 2008/030579 | 3/2008 |
| WO | WO 2008/037477 | 4/2008 |
| WO | WO 2008/052734 | 5/2008 |
| WO | WO 2008/058126 | 5/2008 |
| WO | WO 2008/115974 | 9/2008 |
| WO | WO 2008/155421 | 12/2008 |
| WO | WO 2009/052145 | 4/2009 |
| WO | WO 2009/060197 | 5/2009 |
| WO | WO 2009/140128 | 11/2009 |
| WO | WO 2010/033941 | 4/2010 |
| WO | WO 2010/048314 | 4/2010 |
| WO | WO 2010/051549 | 5/2010 |
| WO | WO 2011/006074 | 1/2011 |
| WO | WO 2011/146336 | 11/2011 |
| WO | WO 2011/146366 | 11/2011 |
| WO | WO 2012/034091 | 3/2012 |
| WO | WO 2012/034095 | 3/2012 |
| WO | WO 2013/059740 | 4/2013 |
| WO | WO 03/080064 | 10/2013 |
| WO | WO 2014/036387 | 3/2014 |
| WO | WO 2014/047572 | 3/2014 |

OTHER PUBLICATIONS

Davies et al., "Resistance to ROS1 inhibition mediated by EGFR pathway activation in non-small cell lung cell," PLoS One, 2013, 8(12):e82236, 13 pages.

Doebele et al., "An oncogenic NTRK fusion in a soft tissue sarcoma patient with response to the tropomysin-related kinase (TRK) inhibitor LOXO-101," American Association for Cancer Research, Jul. 27, 2015, retrieved Jul. 27, 2015, http://www.cancerdiscovery.aacjournals.org, 33 pages.

Dolle et al., "Nerve growth factor-induced migration of endothelial cells," J. Pharmacol Exp Ther, 2005, 315(3):1220-1227.

Frey et al., "7-Aminopyrazolo[1,5-a]pyrimidines as potent multitargeted receptor tyrosine kinase inhibitors," J. Med. Chem, Jul. 2008, 51(13):3777-3787.

Keysar et al., "A patient tumor transplant model of Squamous cell cancer identifies PI3K inhibitors as candidate therapeutics in defined molecular bins," Molecular Oncology, 2013, 7(4):776-790.

Klijn et al., "A comprehensive transcriptional portrait of human cancer cell lines," Nat Biotechnol., 2015, 33(3):306-312.

Linch et al., "Systemic treatment of soft-tissue sarcoma [mdash] gold standard and novel therapies," Nature Reviews Clinical Oncology, 2014, 11(4):187-202.

Lorigan et al., "Phase III trial of two investigational schedules of ifosfamide compared with standard-dose doxorubicin in advanced or metastatic soft tissue sarcoma: a European Organisation for Research and Treatment of Cancer Soft Tissue and Bone Sarcoma Group Study," J. Clin Oncol., 2007, 25(21):3144-3150.

Lovly et al., "Inflammatory myofibroblastic tumors harbor multiple potentially actionable kinase fusions," Cancer Discov., 2014, 4(8):889-895.

Pulciani et al., "Oncogenes in solid human tumours," Nature, 1982, 300(5892):539-542.

Santoro et al., "Doxorubicin versus CYVADIC versus doxorubicin plus ifosfamide in first-line treatment of advanced soft tissue sarcomas: a randomized study of the European Organization for Reasearh and Treatment of Cancer Soft Tissue and Bone Sarcoma Group," J. Clin Oncol., 1995, 13(7):1537-1545.

Sleijfer et al., "Prognastic and predictive factors for outcome to firs-line ifosfamide-containing chemotherapy for adult patients with advanced soft tissue sarcomas:an exploratory, retrospective analysis on large series from the European Organization for Research and Treatment of Cancer-Soft Tissue and Bone Sarcoma Group," Eur J. Cancer, 2010, 46(1):72-83.

Sleijfer et al., "Using single-agent therapy in adult patients with advanced soft tissue sarcoma can still be considered standard care," Oncologist, 2005, 10(10):833-841.

Smith et al., "Annotation of human cancers with EGFR signaling-associated protein complexes using proximity ligation assays," Sci Signal, 2015, 8(359):ra4, 12 pages.

Stephens et al., "Trk receptors use redundant signal transduction pathways involving SHC and PLC-gamma 1 to mediate NGF responses," Neuron, Mar. 1994, 12(3):691-705.

Taipale et al., "Chaperones as thermodynamic sensors of drug-target interactions reveal kinase inhibitor specifities in living cells," Nat Biotech, 2013, 31(7):630-637.

Vaishnavi et al., "TRKing Down an Old Oncogene in a New Era of Targeted Therapy," Cancer Discovery, Jan. 2015, 5(1):25-34.

Winski et al., "LOXO-101, a pan-TRK inhibitor, for the treatment of TRK-driven cancers," 26th EORTC-NCI-AACR Symposium on Molecular Targets and Cancer Therapeutics, Barcelona, Spain, 2014, 175.

Leukemia, Wikipedia The Free Encyclopedia, Dec. 8, 2001, https://en.wikipedia.org/wiki/Leukemia, 15 pages.

Thiele, "On Trk—the TrkB signal transduction pathway is an increasingly important target in cancer biology," Clinical Cancer Research, 2009, 105(19):5962-5967.

Harwood et al., "Experimental organic chemistry—Principles and practice," Experimental Chemistry—Organic Chemistry and Reaction, Jan. 1, 1989, 127-132.

Hong et al., "Clinical Safety and activity from a Phase 1 study of LOXO-101, a selective TRKA/B/C inhibitor, in solid-tumor patients with NTRK gene fusions," 2016 AACR Annual Meeting, Apr. 17, 2016, 32 pages.

International Search Report and Written Opinion in International Application No. PCT/US2015/060953, Feb. 8, 2016, 12 pages.

Mekinist, Highlights of Prescribing Information, Initial Approval 2013, revised Nov. 2015, Novartis Pharmaceuticals Corp., 27 pages.

(56) References Cited

OTHER PUBLICATIONS

Nagasubruamanian et al., "Brief Report: Infantile Fibrsarcoma With NTRK3-ETV6 Fusion Successfully Treated With the Tropomyosin-Related Kinase Inhibitor LOXO-101," Pediatric Blood & Cancer, 2016, DOI 10.1002, 3 pages.

NCT02122913, "Oral TRK Inhibitor LOXO-101 for Treatment of Advanced Adult Solid Tumors," ClinicalTrials.gov, First received Apr. 16, 2014, Last Updated Dec. 7, 2015, https://clinicaltrials.gov/ct2/show/NCT02122913.

NCT02050919, "Sorafenib Tosylate, Combination Chemotherapy, Radiation Therapy, and Surgery in Treating Patients With High-Risk Stage IIB-IV Soft Tissue Sarcoma," ClinicalTrials.gov, First received Jan. 29, 2014, Last Updated Dec. 16, 2015, https://www.clinicaltrials.gov/ct2/show/NCT02050919, 5 pages.

Rutkowski et al., "Treatment of advanced dermatofibrosarcoma protuberans with imatinib mesylate with or without surgical resection," J. Eur. Acad. Dermatol. Venereol., 2011, 25:264-270.

Tafinlar, Highlights of Prescribing Information, GlaxoSmithKline, Jan. 2014, 41 pages.

Xalkori, Highlights of Prescribing Information, Pfizer Labs, Initial approval 2011, revised Mar. 2016, 20 pages.

Zelboraf, Highlights of Prescribing Information, Genentech USA, Initial Approval 2011, revised Aug. 2015, 18 pages.

Adriaenssens et al., "Nerve Growth Factor Is a Potential Therapeutic Target in Breast Cancer," Cancer Res., 2008, 68(2):346-351.

Asaumi et al., "Expression of neurotrophins and their receptors (TRK) during fracture healing," Bone, 2000, 26(6):625-633.

Bardelli, "Mutational analysis of the tyrosine kinome in colorectal cancers," Science, 2003, 300:949.

Brodeur, "Neuroblastoma: biological insights into a clinical enigma," Nat. Rev. Cancer, 2003, 3:203-216.

Brzezianska et al., "Rearrangements of NTRK1 oncogene in papillary thyroid carcinoma," Neuroendocrinology Letters, 2007, 28(3):221-229.

Campos et al., "Enantioselective, palladium-catalyzed alpha-arylation of N-Boc-pyrrolidine," J. Am. Chem Soc., 2006, 128:3538-3539.

Caria et al., "Cytogenetic and molecular events in adenoma and well-differentiated thyroid follicular-cell neoplasia," Cancer Genet. Cytogenet., 2010, 203:21-29.

Chang-Qi et al., "Brain derived neurotrophic factor (BDNF) contributes to the pain hypersensitivity following surgical incision in the rats," Molecular Pain, 2008, 4:27.

Chinese Office Action in Chinese Patent Application No. CN 201180025013.9, Apr. 28, 2014, 11 pages.

Chinese Office Action in Chinese Patent Application No. CN201080040095.X, mailed Feb. 27, 2015, 8 pages (English translation).

Cho et al., "Expression of mRNA for brain-derived neurotrophic factor in the dorsal root ganglion following peripheral inflammation," Brain Research, 1997, 749:358-362.

Colombian Office Action in Colombian Application No. CO 12-022-116-4, Feb. 14, 2014, 8 pages.

Colombian Office Action in Colombian Application No. CO 12-229421-4, Jan. 21, 2014, 6 pages.

Dang et al., "Expression of nerve growth factor receptors is correlated with progression and prognosis of human pancreatic cancer," J. Gastroenterology and Hepatology, 2006, 21(5): 850-858.

Davidson et al., "Expression and activation of the nerve growth factor receptor TrkA in serous ovarian carcinoma," Clin. Cancer Res , 2003, 9(6):2248-2259.

Delafoy et al., "Role of nerve growth factor in the trinitrobenzene sulfonic acid-induced colonic hypersensitivity," Pain, 2003, 105:489-497.

Di Mola et al., "Nerve growth factor and Trk high affinity receptor (TrkA) gene expression in inflammatory bowel disease," Gut, 2000, 46(5):670-678.

Dionne et al., "Cell cycle-independent death of prostate adenocarcinoma is induced by the trk tyrosine kinase inhibitor CEP-751 (KT6587)," Clin. Cancer Research, 1998, 4(8):1887-1898.

Doebele et al., "Phase II Trial of Stereotactic Body Radiation Therapy Combined with Erlotinib for Patients With Limited but Progressive Metastatic Non-Small-Cell Lung Cancer," J. Clin. Oncol., 2014, 32:9 pages.

Dou et al., "Increased nerve growth factor and its receptors in atopic dermatitis: an . immunohistochemical study," Archives of Dermatological Research, 2006, 298(1):31-37.

Du et al., "Expression of NGF family and their receptors in gastric carcinoma: a cDNA microarray study," World Journal of Gastroenterology, http://www.wjgnet.com/1007-9327/full/v9/17/1431.htm, Jul. 2003, 9(7):1431-1434.

Eguchi et al., "Fusion of ETV6 to neurotrophin-3 receptor TRKC in acute myeloid leukemia with t(12;15)(p13;q25)," Blood, 1999, 93(4):1355-1363.

Duranti et al., "Homologation of Mexiletine alkyl chanin and stereoselective blockade of skelatal muscle sodium channels," Euro. J. Med. Chem., 2000, 35:147-156.

European Search Report in European Application No. 13197815.7, mailed Apr. 1, 2014, 5 pages.

Euthus et al., "ETV6-NTRK3—Trk-ing the primary event in human secretory breast cancer," Cancer Cell, 2002, 2(5):347-348.

Frattini et al., "The integrated landscape of driver genomic alterations in glioblastoma," Nature Genet., 2013, 45:1141-1149.

Freund-Michel and Frossard, "The nerve growth factor and its receptors in airway inflammatory diseases," Pharmacology & Therapeutics, 2008, 117(1):52-76.

Greco et al., "Rearrangements of NTRK1 gene in papillary thyroid carcinoma," Molecular and Cellular Endocrinology, 2010, 321(1):44-49.

Green & Wuts, eds, "Protective Groups in Organic Synthesis," John Wiley & Sons Inc.

Gruber-Olipitz et al., "Neurotrophin 3/TrkC-regulated proteins in the human medulloblastoma cell line DAOY," J. Proteome Research, 2008, 7(5):1932-1944.

Gwak et al., "Attenuation of mechanical hyperalgesia following spinal cord injury by administration of antibodies to nerve growth factor in the rat." Neurosci. Left., 2003, 336:117-120.

Hansen et al., "Autophagic cell death induced by TrkA receptor activation in human glioblastoma cells," J. Of Neurochemistry, 2007, 103:259-275.

Herzberg et al., "NGF involvement in pain induced by chronic constriction injury of the rat sciatic nerve," Neuroreport, 1997, 8:1613-1618.

Hu et al., "Decrease in bladder overactivity with REN1820 in rats with cyclophosphamide induced cystitis," J. Urology, 2005, 173(3):1016-1021.

Hu et al., "Identification of brain-derived neurotrophic factor as a novel angiogenic protein in multiple myeloma" Cancer Genetics and Cytogenetics, 2007, 178:1-10.

Igaz et al., "Biological and clinical significance of the JAK-STAT pathway; lessons from knockout mice," Inflamm. Res., 2001, 50:435-441.

Ihle et al., "The Roles of Jaks and Stats in Cytokine Signaling," Canc. J. Sci. Am., 1998, 4(1):84-91.

International Preliminary Report on Patentability in International Application No. PCT/US2009/057729, mailed Mar. 22, 2011, 7 pages.

International Preliminary Report on Patentability in International Application No. PCT/US2009/061519, mailed Apr. 26, 2011, 6 pages.

International Preliminary Report on Patentability in International Application No. PCT/US2010/041538, mailed Jan. 10, 2012, 7 pages.

International Preliminary Report on Patentability in International Application No. PCT/US2011/036452, mailed Nov. 29, 2012, 6 pages.

International Search Report and Written Opinion in International Application No. PCT/US2009/0161519, mailed Feb. 2, 2010, 8 pages.

(56) References Cited

OTHER PUBLICATIONS

International Search Report and Written Opinion in International Application No. PCT/US2009/057729, mailed Feb. 4, 2010, 10 pages.
International Search Report and Written Opinion in International Application No. PCT/US2010/041538, mailed Oct. 1, 2010, 10 pages.
International Search Report and Written Opinion in International Application No. PCT/US2011/036452, Aug. 18, 2011, 9 pages.
Jaggar et al., "Inflammation of the rat urinary bladder is associated with a referred thermal hyperalgesia which is nerve growth factor dependent," Br. J. Anaesth, 1999, 83:442-448.
Japanese Office Action in Japanese Application No. JP 2013-511239, dated Mar. 4, 2015, 2 pages (English translation).
Jin et al., "TrkC plays an essential role in breast tumor growth and metastasis," Carcinogenesis, 2010, 31(11):1939-1947.
Jones et al., "Recurrent somatic alterations of FGFR1 and NTRK2 in pilocytic astrocytoma," Nature Genetics, 2013, 45:927-932.
Kim et al., "NTRK1 fusion in glioblastoma multiforme," PloS One, 2014, 9(3):e91940.
Kolokythas et al., "Nerve growth factor and tyrosine kinase A receptor in oral squamous cell carcinoma: is there an association with perineural invasion?" J. Oral Maxillofacial Surgery, 2010, 68(6):1290-1295.
Kremer et al., "The safety and efficacy of a JAK inhibitor in patients with active rheumatoid arthritis: Results of a double-blind, placebo-controlled phase IIa trial of three dosage levels of CP-690,550 versus placebo," Arth. & Rheum., 2009, 60:1895-1905.
Kruettgen et al., "The dark side of the NGF family: neurotrophins in neoplasias," Brain Pathology, 2006, 16:304-310.
Lamb et al., "Nerve growth factor and gastric hyperalgesia in the rat," Neurogastrenterol. Motil., 2003, 15:355-361.
Li et al., "Lumbar 5 ventral root transection-induced upregulation of nerve growth factor in sensory neurons and their target tissues: a mechanism in neuropathic pain," Mol. Cell. Neurosci., 2003, 23:232-250.
Li et al., "Correlation of expressions of GFAP, Nt-3, TRK and NCAM with neurotropic molecular mechanism and clinical factors in adenoid cystic carcinoma of salivary gland," Chinese Journal of Cancer Prevention and Treatment, 2009, 16(6): 428-430 (with English abstract).
Li et al., "Brain derived neurotrophic factor (BDNF) contributes to the pain hypersensitivity following surgical incision in the rats," Molecular Pain, 2008, 4(28):1-11.
Ma and Woolf, "The progressive tactile hyperalgesia induced by peripheral inflammation is nerve growth factor dependent," Neuroreport, 1997, 8:807-810.
Marchetti et al., "Frequent mutations in the neurotrophic tyrosine receptor kinase gene family in large cell neuroendocrine carcinoma of the lung," Human Mutation, 2008, 29(5):609-616.
Martin-Zanca et al., "A human oncogene formed by the fusion of truncated tropomyosin and protein tyrosine kinase sequences," Nature, 1986, 319:743.
Matayoshi, "Actions of brain-derived neurotrophic factor on spinal nociceptive transmission during inflammation in the rat," J. Physiol., 2005, 569:685-695.
McMahon et al., "The biological effects of endogenous nerve growth factor on adult sensory neurons revealed by a trkA-IgG fusion molecule," Nat. Med., 1995, 1:774-780.
McMahon., "VEGF Receptor Signaling in Tumor Angiogenesis," The Oncologist, 2000, 5(1): 3-10.
Melo-Jorge et al., The Chagas' disease parasite Trypanosoma cruzi exploits nerve growth factor receptor TrkA to infect mammalian hosts Cell Host & Microbe, 2007, 1(4):251-261.
Meyer et al., "Remarkable leukemogenic potency and quality of a constitutively active neurotrophin receptor, deltaTrkA," Leukemia, 2007, 21:2171-2180.
Nakagawara, "Trk receptor tyrosine kinases: a bridge between cancer and neural development," Cancer Letters, 2001, 169:107-114.

National Cancer Institute at the National Institutes of Health, posted on or before Jan. 5, 2000, retrieved on Jan. 13, 2015, http://www.cancer.gov/, 2 pages.
National Comprehensive Cancer Network, posted on or before Dec. 3, 1998, retrieved on Jan. 13, 2015, http://www.nccn.org/, 1 page.
Ni et al., "siRNA interference with a proliferation-inducing ligand gene in the Sgr-7901 gastric carcinoma cell line," Asian Pacific Journal of Cancer Prevention, 2012, 13:1511-1514.
Perrault et al., "The Synthesis of N-Aryl-5(S)-aminomethyl-2-oxazolidinone Antibacterials and Derivatives in One Step from Aryl Carbamates," Org. Process Res. Dev., 2003, 7:533-546.
O'Shea, "Jaks, STATs, cytokine signal transduction, and immunoregulation: are we there yet?" Immunity, 1997, 7:1-11.
Papatsoris et al., "Manipulation of the nerve growth factor network in prostate cancer," Exper Opin Invest Drugs, 2007, 16(3):303-309.
Patani et al., "Bioisosterism: A rational approach in Drug Design," Chem Rev., Dec. 1996, 96(8):3147-3176.
Patapoutian et al., "Trk receptors: mediators of neurotrophin action," Current Opinion in Neurobiology, 2001, 11:272-280.
Perez-Pinera et al., "The Trk tyrosine kinase inhibitor K252a regulates growth of lung adenocarcinomas," Molecular and Cellular Biochemistry, 2007, 295(1&2):19-26.
Philippines Office Action in Philippines Application No. Ph Jan. 2012/500048, May 30, 2014, 2 pages.
Pierottia and Greco, "Oncogenic rearrangements of the NTRK1/NGF receptor," Cancer Letters, 2006, 232:90-98.
Pinedo et al., "Translational Research: The Role of VEGF in Tumor Angiogenesis," The Oncologist, 2000, 5(1): 1-2.
Pinski et al., "Trk receptor inhibition induces apoptosis of proliferating but not quiescent human osteoblasts," Cancer Res, 2002, 62:986-989.
Ramer and Bisby, "Adrenergic innervation of rat sensory ganglia following proximal or distal painful sciatic neuropathy: distinct mechanisms revealed by anti-NGF treatment," Eur. J. Neurosci., 1999, 11:837-846.
Raychaudhuri et al., 'K252a, a high-affinity nerve growth factor receptor blocker, improves psoriasis: an in vivo study using the severe combined immunodeficient mouse-human skin model, J. Investigative Dermatology, 2004, 122(3):812-819.
Reuther et al., "Identification and characterization of an activating TrkA deletion mutation in acute myeloid leukemia," Mol. Cell. Biol. 2000, 20:8655-8666.
Ricci et al., 'Neurotrophins and neurotrophin receptors in human lung cancer, Am. J. Respiratory Cell and Molecular Biology, Yr, 25(4): 439-446.
Ro et al., "Effect of NGF and anti-NGF on neuropathic pain in rats following chronic constriction injury of the sciatic nerve," Pain, 1999, 79:265-274.
Ross et al., "New routes to targeted therapy of intrahepatic cholangiocarcinomas revealed by next-generation sequencing," Oncologist, 2014, 19:235-242.
Shelton et al., "Nerve growth factor mediates hyperalgesia and cachexia in auto-immune arthritis," Pain, 2005, 116:8-16.
Silverman, The Organic Chemistry of Drug Design and Drug Action, Second Edition, 2007, 20-21.
Sohrabji et al., "Estrogen-BDNF interactions: implications for neurodegenerative diseases," Frontiers in Neuroendocrinology, 2006, 27(4):404-414.
Stransky et al., "The landscape of kinase fusions in cancer," Nature comm., 2014, 5:4846.
Tacconelli et al., "TrkA alternative splicing: a regulated tumor-promoting switch in human neuroblastoma," Cancer Cell, 2004, 6:347-360.
Taiwan Office Action in Taiwan Application No. 098135670, Jan. 20, 2014, 7 pp. (with English Translation).
Taiwan Search Report in Taiwan Application No. 098132033, Dec. 13, 2013, 1 p. (English translation only).
Theodosiou et al., "Hyperalgesia due to nerve damage: role of nerve growth factor," Pain, 1999, 81:245-255.
Thompson et al., "Brain-derived neurotrophic factor is an endogenous modulator of nociceptive responses in the spinal cord," Proc.Natl. Acad. Sci. Usa, 1999, 96:7714-7718.

(56) References Cited

OTHER PUBLICATIONS

Truzzi et al., "Neurotrophins and their receptors stimulate melanoma cell proliferation and migration," J. Investigative Dermatology, 2008, 128(8):2031-2040.

Truzzi et al., "Neurotrophins in healthy and diseased skin ," Dermato-Endrocrinology, 2008, 3(1):32-36.

Vaishnavi et al., 'Oncogenic and drug-sensitive NTRK1 rearrangements in lung cancer, Nature Med., 2013, 19:1469-1472.

Van Gurp et al., "Phase 1 dose-escalation study of CP-690 550 in stable renal allograft recipients: preliminary findings of safety, tolerability, effects on lymphocyte subsets and pharmacokinetics," Am. J. Transpl., 2008, 8:1711-1718.

Van Noesel et al., "Pediatric neuroblastomas: genetic and epigenetic 'danse macabre'," Gene, 2004, 325:1-15.

Wadhwa et al., "Expression of the neurotrophin receptors Trk a and Trk B in adult human astrocytoma and glioblastoma," Journal of Biosciences, 2003, 28(2):181-188.

Walch et al., "Role of neurotrophins and neurotrophins receptors in the in vitro invasion and heparanase production of human prostate cancer cells," Clin. Exp. Metastasis, 1999, 17:307-314.

Wang et al., "Trk kinase inhibitors as new treatments for cancer and pain," Expert Opin. Ther Patents, Mar. 2009, 19(3):305-319.

Wiesner et al., "Kinase fusions are frequent in Spitz tumours and spitzoid melanomas," Nature Comm., 2014, 5:3116.

Woolf et al., "Letter to Neuroscience: Nerve Growth Factor Contributes to the Generation of Inflammatory Sensory Hypersensitivity," Neuroscience, 1994, 62:627-331.

Wu et al., "The genomic landscape of diffuse intrinsic pontine glioma and pediatric non-brainstem high-grade glioma," Nature Genetics, 2014, 444-450.

Yilmaz et al., "Theraputic targeting of Trk supresses tumor proliferation and enhances cisplatin activity in HNSCC," Cancer Biology and Therapy, 2010, 10(6):644-653.

Zahn et al., "Effect of blockade of nerve growth factor and tumor necrosis factor on pain behaviors after plantar incision," J. Pain, 2004, 5:157-163.

Zhang et al., "Expression of nerve growth factor receptors and their prognostic value in human pancreatic cancer," Oncology Reports, 2005, 14:161-171.

Zheng et al., "Anchored multiplex PCR for targeted next-generation sequencing," Nature Med., Dec. 2014, 20(12):1479-1486.

\* cited by examiner

MACROCYCLIC COMPOUNDS AS TRK KINASE INHIBITORS

The present invention relates to novel compounds, to pharmaceutical compositions comprising the compounds, to processes for making the compounds and to the use of the compounds in therapy. More particularly, it relates to certain macrocyclic compounds which exhibit Trk family protein tyrosine kinase inhibition, and which are useful in the treatment of pain, cancer, inflammation, neurodegenerative diseases and certain infectious diseases.

The current treatment regimes for pain conditions utilize several classes of compounds. The opioids (such as morphine) have several drawbacks including emetic, constipatory and negative respiratory effects, as well as the potential for addiction. Non-steroidal anti-inflammatory analgesics (NSAIDs, such as COX-1 or COX-2 types) also have drawbacks including insufficient efficacy in treating severe pain and the potential for internal gastrointestinal bleeding. In addition, COX-1 inhibitors can cause ulcers of the mucosa. Accordingly, there is a continuing need for new and more effective treatments for the relief of pain, especially chronic pain.

Trk's are high affinity receptor tyrosine kinases activated by a group of soluble growth factors called neurotrophins (NT). The Trk receptor family has three members: TrkA, TrkB and TrkC. Among the neurotrophins are (i) nerve growth factor (NGF) which activates TrkA, (ii) brain-derived neurotrophic factor (BDNF) and NT-4/5 which activate TrkB and (iii) NT3 which activates TrkC. Trk's are widely expressed in neuronal tissue and are implicated in the maintenance, signaling and survival of neuronal cells (Patapoutian, A. et al., *Current Opinion in Neurobiology*, 2001, 11, 272-280).

Inhibitors of the Trk/neurotrophin pathway have been demonstrated to be effective in numerous pre-clinical animal models of pain. For example, antagonistic NGF and TrkA antibodies such as RN-624 have been shown to be efficacious in inflammatory and neuropathic pain animal models (Woolf, C. J. et al. (1994) *Neuroscience* 62, 327-331; Zahn, P. K. et al. (2004) *J. Pain* 5, 157-163; McMahon, S. B. et al., (1995) *Nat. Med.* 1, 774-780; Ma, Q. P. and Woolf, C. J. (1997) *Neuroreport* 8, 807-810; Shelton, D. L. et al. (2005) *Pain* 116, 8-16; Delafoy, L. et al. (2003) *Pain* 105, 489-497; Lamb, K. et al. (2003) *Neurogastroenterol. Motil.* 15, 355-361; Jaggar, S. I. et al. (1999) *Br. J. Anaesth.* 83, 442-448) and neuropathic pain animal models (Ramer, M. S. and Bisby, M. A. (1999) *Eur. J. Neurosci.* 11, 837-846; Ro, L. S. et al. (1999); *Pain* 79, 265-274 Herzberg, U. et al. (1997) *Neuroreport* 8, 1613-1618; Theodosiou, M. et al. (1999) *Pain* 81, 245-255; Li, L. et al. (2003) *Mol. Cell. Neurosci.* 23, 232-250; Gwak, Y. S. et al. (2003) *Neurosci. Lett.* 336, 117-120).

It has also been shown that NGF secreted by tumor cells and tumor invading macrophages directly stimulates TrkA located on peripheral pain fibers. Using various tumor models in both mice and rats, it was demonstrated that neutralizing NGF with a monoclonal antibody inhibits cancer related pain to a degree similar or superior to the highest tolerated dose of morphine. In addition, activation of the BDNF/TrkB pathway has been implicated in numerous studies as a modulator of various types of pain including inflammatory pain (Matayoshi, S., *J. Physiol.* 2005, 569: 685-95), neuropathic pain (Thompson, S. W., *Proc. Natl. Acad. Sci. USA* 1999, 96:7714-18) and surgical pain (Li, C.-Q. et al., *Molecular Pain*, 2008, 4(28), 1-11).

Recent literature has also shown that overexpression, activation, amplification and/or mutation of Trk kinases are associated with many cancers including neuroblastoma (Brodeur, G. M., *Nat. Rev. Cancer* 2003, 3, 203-216), ovarian (Davidson. B., et al., *Clin. Cancer Res.* 2003, 9, 2248-2259), colorectal cancer (Bardelli, A., *Science* 2003, 300, 949), melanoma (Truzzi, F., et al., *Dermato-Endocrinology* 2008, 3 (1), pp. 32-36), head and neck cancer (Yilmaz, T., et al., *Cancer Biology and Therapy* 2010, 10 (6), pp. 644-653), gastric carcinoma (Du, J. et al., *World Journal of Gastroenterology* 2003, 9 (7), pp. 1431-1434), lung carcinoma (Ricci A., et al., *American Journal of Respiratory Cell and Molecular Biology* 25 (4), pp. 439-446), breast cancer (Jin, W., et al., *Carcinogenesis* 2010, 31 (11), pp. 1939-1947), Glioblastoma (Wadhwa, S., et al., *Journal of Biosciences* 2003, 28 (2), pp. 181-188), medulloblastoma (Gruber-Olipitz, M., et al., *Journal of Proteome Research* 2008, 7 (5), pp. 1932-1944), secratory breast cancer (Euthus, D. M., et al., *Cancer Cell* 2002, 2 (5), pp. 347-348), salivary gland cancer (Li, Y.-G., et al., *Chinese Journal of Cancer Prevention and Treatment* 2009, 16 (6), pp. 428-430), papillary thyroid carcinoma (Greco, A., et al., *Molecular and Cellular Endocrinology* 2010, 321 (1), pp. 44-49) and adult myeloid leukemia (Eguchi, M., et al., *Blood* 1999, 93 (4), pp. 1355-1363). In preclinical models of cancer, non-selective small molecule inhibitors of Trk A, B and C were efficacious in both inhibiting tumor growth and stopping tumor metastasis (Nakagawara, A. (2001) *Cancer Letters* 169:107-114; Meyer, J. et al. (2007) *Leukemia*, 1-10; Pierottia, M. A. and Greco A., (2006) *Cancer Letters* 232:90-98; Eric Adriaenssens, E., et al. *Cancer Res* (2008) 68:(2) 346-351).

In addition, inhibition of the neurotrophin/Trk pathway has been shown to be effective in treatment of pre-clinical models of inflammatory diseases with NGF antibodies or non-selective small molecule inhibitors of Trk A, B and C. For example, inhibition of the neurotrophin/Trk pathway has been implicated in preclinical models of inflammatory lung diseases including asthma (Freund-Michel, V; Frossard, N., *Pharmacology & Therapeutics* (2008), 117(l), 52-76), interstitial cystitis (Hu Vivian, Y., et. al. *The Journal of Urology* (2005), 173(3), 1016-21), inflammatory bowel diseases including ulcerative colitis and Crohn's disease (Di Mola, F. F., et. al., *Gut* (2000), 46(5), 670-678) and inflammatory skin diseases such as atopic dermatitis (Dou, Y.-C., et. al. *Archives of Dermatological Research* (2006), 298(1), 31-37), eczema and psoriasis (Raychaudhuri, S. P., et al., *J. Investigative Dermatology* (2004), 122(3), 812-819).

The neurotrophin/Trk pathway, particularly BDNF/TrkB, has also been implicated in the etiology of neurodegenerative diseases including multiple sclerosis, Parkinson's disease and Alzheimer's Disease (Sohrabji, F., Lewis, Danielle K., *Frontiers in Neuroendocrinology* (2006), 27(4), 404-414).

The TrkA receptor is also thought to be critical to the disease process in the infection of the parasitic infection of *Trypanosoma cruzi* (Chagas disease) in human hosts (de Melo-Jorge, M., et al., *Cell Host & Microbe* (2007), 1(4), 251-261).

Several classes of small molecule inhibitors of Trk kinases said to be useful for treating pain or cancer are known (*Expert Opin. Ther. Patents* (2009) 19(3)).

There remains a need, however, for compounds and methods for the treatment of pain, in particular chronic pain, as well as for the treatment of cancer, inflammation, neurodegenerative diseases and certain infectious diseases.

SUMMARY OF THE INVENTION

It has now been found that macrocyclic compounds are inhibitors of Trk kinases, in particular inhibitors of TrkA and/or TrkB and/or TrkC, and are useful for treating disorders and diseases such as cancer and pain, including chronic and acute pain. Compounds which are inhibitors of TrkA and/or TrkB may be useful in the treatment of multiple types of pain including inflammatory pain, neuropathic pain, and pain associated with cancer, surgery and bone fracture. In addition, compounds of the invention may be useful for treating inflammation, neurodegenerative diseases and certain infectious diseases.

Accordingly, in one aspect present invention provides novel compounds having the general Formula I:

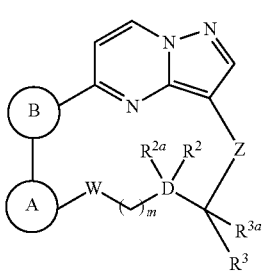

and stereoisomers and pharmaceutically acceptable salts and solvates thereof, wherein ring A, ring B, W, m, D, $R^2$, $R^{2a}$, $R^3$, $R^{3a}$ and Z are as defined herein.

In another aspect, the present invention provides novel compounds having the general Formula I:

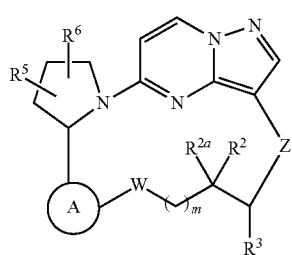

or pharmaceutically acceptable salts or solvates thereof, wherein ring A, W, m, $R^2$, $R^{2a}$, $R^3$, Z, $R^5$ and $R^6$ are as defined herein.

In another aspect of the invention, there are provided pharmaceutical compositions comprising compounds of Formula I and a carrier, diluent or excipient.

In another aspect of the invention, there is provided a method for treating or preventing pain, cancer, inflammation, neurodegenerative diseases and certain infectious diseases in a mammal, comprising administering to said mammal an effective amount of a compound of Formula I.

In another aspect of the invention, there is provided a use of a compound of Formula I in the manufacture of a medicament for the treatment or prevention of pain, cancer, inflammation, neurodegenerative diseases and certain infectious diseases.

In another aspect of the invention, there is provided a use of a compound of Formula I in the treatment or prevention of pain, cancer, inflammation, neurodegenerative diseases and certain infectious diseases.

Another aspect provides intermediates for preparing compounds of Formula I. In one embodiment, certain compounds of Formula I may be used as intermediates for the preparation of other compounds of Formula I.

Another aspect includes processes for preparing, methods of separation, and methods of purification of the compounds described herein.

DETAILED DESCRIPTION OF THE INVENTION

One embodiment of this invention provides compounds of the general Formula I containing a pyrazolo[1,5-a]pyrimidinyl ring and having the structure:

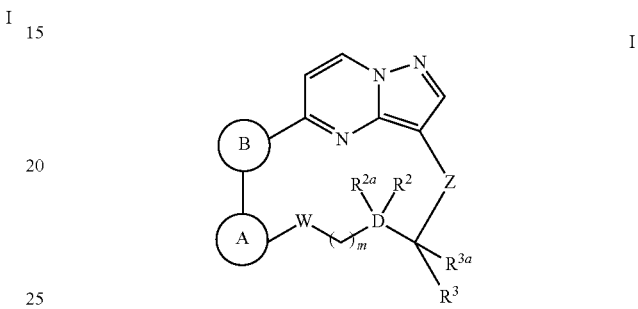

or pharmaceutically acceptable salts or solvates thereof, wherein:

ring A is selected from rings A-1, A-2 and A-3 having the structures:

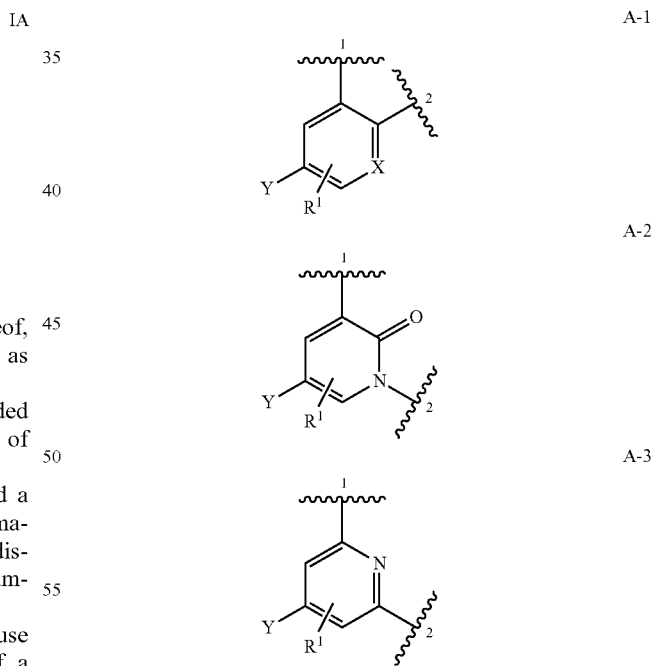

wherein the wavy line labeled 1 indicates the point of attachment of ring A to ring B and the wavy line labeled 2 indicates the point of attachment of ring A to W;

X is N or CH;

Y is H or F;

$R^1$ is H, (1-3C)alkoxy or halogen;

ring B is selected from rings B-1 and B-2 having the structures:

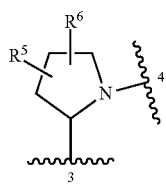

B-1

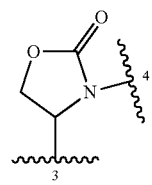

B-2 wherein the wavy line labeled 3 indicates the point of attachment to ring A and the wavy line labeled 4 indicates the point of attachment to the pyrazolo[1,5-a]pyrimidine ring of Formula I;

W is O, NH or CH$_2$, wherein when ring A is A-2, then W is CH$_2$;

m is 0, 1 or 2;

D is carbon;

R$^2$ and R$^{2a}$ are independently H, F, (1-3 C)alkyl or OH, provided that R$^2$ and R$^{2a}$ are not both OH;

R$^3$ and R$^{3a}$ are independently H, (1-3 C)alkyl or hydroxy (1-3 C)alkyl;

or D is carbon or nitrogen, R$^2$ and R$^3$ are absent and R$^{2a}$ and R$^{3a}$ together with the atoms to which they are attached form a 5-6 membered heteroaryl ring having 1-2 ring heteroatoms;

Z is *—NR$^{4a}$C(=O)—, *—ONHC(=O)—, *—NR$^{4b}$CH$_2$— or *—OC(=O)—, wherein the asterisk indicates the point of attachment of Z to the carbon bearing R$^3$;

R$^{4a}$ is H, (1-6C)alkyl, fluoro(1-6C)alkyl, difluoro(1-6C)alkyl, trifluoro(1-6C)alkyl, hydroxy(1-6C alkyl) or dihydroxy(2-6C alkyl);

R$^{4b}$ is H, (1-6C)alkyl, fluoro(1-6C)alkyl, difluoro(1-6C)alkyl, trifluoro(1-6C)alkyl, hydroxy(1-6C alkyl), dihydroxy(2-6C alkyl), (1-6C alkyl)C(O)—, (3-6C cycloalkyl)C(O)—, Ar$^1$C(O)—, HOCH$_2$C(O)—, (1-6C alkyl)sulfonyl, (3-6C cycloalkyl)sulfonyl, Ar$^2$(SO$_2$)—, HO$_2$CCH$_2$— or (1-6C alkyl)NH(CO)—;

Ar$^1$ is phenyl optionally substituted with one or more substituents independently selected from halogen, (1-6C)alkyl, and (1-6C)alkoxy;

Ar$^2$ is phenyl optionally substituted with one or more substituents independently selected from halogen, (1-6C)alkyl, and (1-6C)alkoxy; and R$^5$ and R$^6$ are independently H, halogen, OH, (1-6C)alkyl or hydroxy(1-6C)alkyl.

In one embodiment of Formula I, ring B is ring B-2 having the structure:

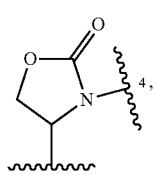

B-2

D is carbon, R$^2$ and R$^{2a}$ am independently (1-3 C)alkyl, and R$^3$ and R$^{3a}$ are independently H, (1-3 C)alkyl or hydroxy (1-3 C)alkyl, or D is carbon or nitrogen, R$^2$ and R$^3$ are absent and R$^{2a}$ and R$^{3a}$ together with the atoms to which they are attached form a 5-6 membered heteroaryl ring having 1-2 ring heteroatoms.

In one embodiment of Formula I, ring A is ring A-1 having the structure

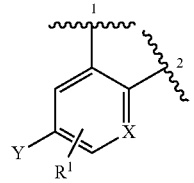

A-1 wherein X, Y and R$^1$ are as defined for Formula I. In one embodiment of Formula I, X is CH. In one embodiment, X is N. In one embodiment of Formula I, Y is F. In one embodiment, Y is H. In one embodiment of Formula I, R$^1$ is H. In one embodiment, R$^1$ is (1-3C)alkoxy. A particular example is methoxy. In one embodiment, R$^1$ is halogen. In one embodiment, R$^1$ is F.

Particular examples of ring A when represented by structure A-1 include the structures:

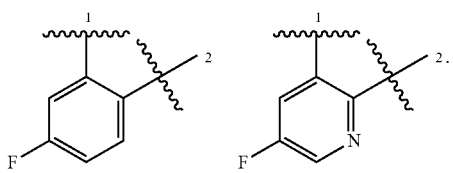 [SMILES: *c1ccc(F)cc1* ; *c1cc(F)cnc1*]

In one embodiment, ring A is ring A-2 having the structure

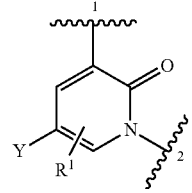

A-2 wherein Y is H or F. In one embodiment, Y is F. In one embodiment, Y is H. In one embodiment, R$^1$ is H. In one embodiment, R$^1$ is (1-3C)alkoxy. A particular example is methoxy. In one embodiment, R$^1$ is halogen. In one embodiment, R$^1$ is F.

Particular examples of ring A when represented by ring A-2 are the structures:

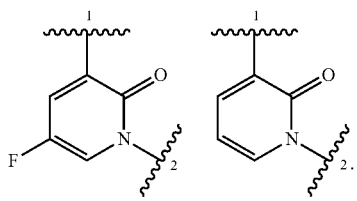

In one embodiment of Formula I, ring A is ring A-3 having the structure

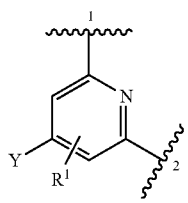

A-3 wherein Y and $R^1$ is as defined for Formula I. In one embodiment, Y is F. In one embodiment, Y is H. In one embodiment, $R^1$ is H. In one embodiment. $R^1$ is (1-3C)alkoxy. A particular example is methoxy. In one embodiment, $R^1$ is halogen. In one embodiment, $R^1$ is F.

Particular examples of ring A when represented by ring A-3 are the structures:

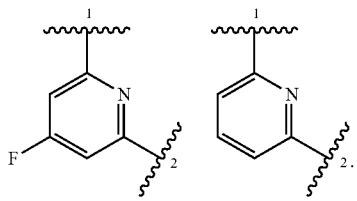 [SMILES: *c1cc(F)cc(*)n1 ; *c1cccc(*)n1]

In one embodiment of Formula I, W is O.

In one embodiment, W is NH.

In one embodiment, W is $CH_2$.

In one embodiment of Formula I, D is carbon, $R^2$ and $R^{2a}$ are independently H. F, (1-3 C)alkyl or OH (provided that $R^2$ and $R^{2a}$ are not both OH), and $R^3$ and $R^{3a}$ are independently H, (1-3 C)alkyl or hydroxy(1-3 C)alkyl.

In one embodiment, $R^2$ and $R^{2a}$ are independently H, F, methyl or OH, provided that $R^2$ and $R^{2a}$ are not both OH.

In one embodiment, $R^2$ and $R^{2a}$ are both H.

In one embodiment, $R^2$ is H and $R^{2a}$ is F.

In one embodiment, $R^2$ and $R^{2a}$ are both F.

In one embodiment, $R^2$ is H and $R^{2a}$ is OH.

In one embodiment, $R^2$ is H and $R^{2a}$ is methyl.

In one embodiment, $R^2$ and $R^{2a}$ are both methyl.

In one embodiment, $R^3$ and $R^{3a}$ are independently H, (1-3C)alkyl or hydroxy(1-3 C)alkyl.

In one embodiment, $R^{3a}$ is H. In one embodiment, $R^3$ is H. In one embodiment, both $R^3$ and $R^{3a}$ are H.

In one embodiment, $R^{3a}$ is (1-3C)alkyl. Examples include methyl, ethyl, propyl and isopropyl. In one embodiment, $R^3$ is (1-3C)alkyl. Examples include methyl, ethyl, propyl and isopropyl.

In one embodiment, $R^{3a}$ is (1-3C)alkyl and $R^3$ is H. In one embodiment, $R^{3a}$ is methyl and $R^3$ is H.

In one embodiment, both $R^{3a}$ and $R^3$ are (1-3C)alkyl. In one embodiment, $R^{3a}$ and $R^{3a}$ are both methyl.

In one embodiment, $R^1$ is hydroxy(1-3C)alkyl. Examples include hydroxymethyl, 2-hydroxyethyl, 2-hydroxypropyl, and 3-hydroxypropyl. In one embodiment, $R^3$ is hydroxymethyl, 2-hydroxyethyl, 2-hydroxypropyl, or 3-hydroxypropyl and $R^{3a}$ is H.

In one embodiment of Formula I, D is carbon or nitrogen, $R^2$ and $R^3$ are absent, and $R^{2a}$ and $R^{3a}$ together with the atoms to which they are attached form a 5-6 membered heteroaryl ring having 1-2 ring heteroatoms. In one embodiment, $R^{2a}$ and $R^{3a}$ together with the atoms to which they are attached form a 5-6 membered heteroaryl ring having 1-2 ring nitrogen atoms. Examples of heteroaryl rings include pyridyl and pyrazolyl rings. Specific examples of heteroaryl rings include the structures:

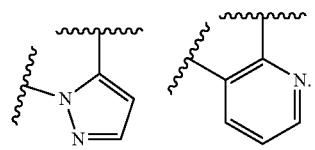 [SMILES: *c1ccnn1* ; *c1cccnc1*]

In one embodiment, Z is *—$NR^{4a}C(=O)$—.

In one embodiment, $R^{4a}$ is H.

In one embodiment, $R^{4a}$ is (1-6C)alkyl. Examples include methyl, ethyl, propyl, isopropyl, butyl, and isobutyl.

In one embodiment, $R^{4a}$ is fluoro(1-6C)alkyl. Examples include fluoromethyl and 2-fluoroethyl.

In one embodiment, $R^{4a}$ is difluoro(1-6C)alkyl. Example include difluoromethyl and 2,2-difluoroethyl.

In one embodiment, $R^{4a}$ is trifluoro(1-6C)alkyl. Examples include trifluoromethyl and 2,2,2-trifluoroethyl.

In one embodiment, $R^{4a}$ is hydroxy(1-6C alkyl). Examples include hydroxymethyl, 2-hydroxyethyl, 2-hydroxypropyl and 3-hydroxypropyl.

In one embodiment, $R^{4a}$ is dihydroxy(2-6C alkyl). An example includes 2,3-dihydroxypropyl.

In one embodiments, $R^{4a}$ is H or (1-6C)alkyl. In one embodiment, $R^{4a}$ is H or Me.

An example of Z when represented by *—$NR^{4a}C(=O)$— is *—$ONHC(=O)$—.

In one embodiment, Z is *—$NR^{4b}CH_2$—.

In one embodiment, $R^{4b}$ is H.

In one embodiment, $R^{4b}$ is selected from (1-6C)alkyl, fluoro(1-6C)alkyl, difluoro(1-6C)alkyl, and trifluoro(1-6C) alkyl.

In one embodiment, $R^{4b}$ is (1-6C)alkyl. Examples include methyl, ethyl, propyl, isopropyl, butyl and tert-butyl. In one embodiment, $R^{4b}$ is methyl.

In one embodiment, $R^{4b}$ is fluoro(1-6C)alkyl. Examples include fluoromethyl and 2-fluoroethyl.

In one embodiment, $R^{4b}$ is difluoro(1-6C)alkyl. Example include difluoromethyl and 2,2-difluoroethyl.

In one embodiment, $R^{4b}$ is trifluoro(1-6C)alkyl. Examples include trifluoromethyl and 2,2,2-trifluoroethyl.

In one embodiment, $R^{4b}$ is selected from (1-6C alkyl)C(O)—, (3-6C cycloalkyl)C(O)—. $Ar^1C(O)$— and $HOCH_2C(O)$—.

In one embodiment, $R^{4b}$ is (1-6C alkyl)C(O)—. Examples include $CH_3C(O)$—, $CH_3CH_2C(O)$—, $CH_3CH_2CH_2C(O)$—, and $(CH_3)_2CHC(O)$—. In one embodiment, $R^4$ is $CH_3C(O)$—.

In one embodiment, $R^{4b}$ is (3-6C cycloalkyl)C(O)—. Examples include cyclopropylC(O)—, cyclobutylC(O)—, cyclopentylC(O)— and cyclohexylC(O)—.

In one embodiment, $R^{4b}$ is $Ar^1C(O)$—. An example is phenylC(O)—.

In one embodiment, $R^{4b}$ is $HOCH_2C(O)$—.

In one embodiment, $R^{4b}$ is selected from (1-6C alkyl)sulfonyl, (3-6C cycloalkyl)sulfonyl, and $Ar^2(SO_2)$—.

In one embodiment, $R^{4b}$ is (1-6C alkyl)sulfonyl. Examples include methylsulfonyl, ethylsulfonyl and propylsulfonyl.

In one embodiment, $R^{4b}$ is (3-6C cycloalkyl)sulfonyl. Examples include cyclopropylsulfonyl, cyclobutylsulfonyl, cyclopentylsulfonyl and cyclohcxylsulfonyl. In one embodiment, $R^4$ is methylsulfonyl.

In one embodiment, $R^{4b}$ is $Ar^2(SO_2)$—. An example is phenylsulfonyl.

In one embodiment, $R^{4b}$ is $HO_2CCH_2$—.

In one embodiment, $R^{4b}$ is (1-6C alkyl)NH(CO)—. Examples include $CH_3NHC(O)$—, $CH_3CH_2NHC(O)$—, $CH_3CH_2CH_2NHC(O)$—, and $(CH_3)_2CHNHC(O)$—. In one embodiment. $R^4$ is $CH_3NHC(O)$—.

In one embodiment, $R^{4b}$ is selected from H, methyl, —C(O)CH_3, methylsulfonyl, —C(O)CH_2OH, —CH_2COOH and —C(O)NHCH_2CH_3.

In one embodiment, Z is *—OC(=O)—.

In one embodiment of Formula I, ring B is ring B-1:

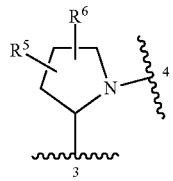

B-1 where $R^5$ and $R^6$ are independently H, halogen, OH, (1-6C)alkyl or hydroxy(1-6C)alkyl.

In one embodiment, $R^5$ and $R^6$ are independently H, F, OH, (1-6C)alkyl or hydroxy(1-6C)alkyl. In one embodiment, $R^5$ is H and $R^6$ is H, F, OH, (1-6C)alkyl or hydroxy(1-6C)alkyl.

In one embodiment, $R^5$ and $R^6$ are independently H, F, OH, (1-3C)alkyl or hydroxy(1-3C)alkyl. In one embodiment, $R^5$ is hydrogen and $R^6$ is H, F, OH, (1-3C)alkyl or hydroxy(1-3C)alkyl.

In one embodiment, $R^5$ and $R^6$ are independently H, F, OH, methyl, ethyl, $HOCH_2$— or $HOCH_2CH_2$—. In one embodiment, $R^5$ is hydrogen and $R^6$ is H, F, OH, methyl, ethyl, $HOCH_2$— or $HOCH_2CH_2$—.

In one embodiment, $R^5$ and $R^6$ are independently H. F, or methyl. In one embodiment, $R^5$ is H and $R^6$ is H, F, or methyl.

In one embodiment, $R^5$ is H and $R^6$ is F.
In one embodiment, $R^5$ is H and $R^6$ is methyl.
In one embodiment, $R^5$ and $R^6$ are both H.
In one embodiment, $R^5$ and $R^6$ are both F.
In one embodiment, $R^5$ and $R^6$ are both methyl.

In one embodiment, ring B is ring B-1 which is optionally substituted with one or two substituents independently selected from OH and F, provided that two OH substituents are not on the same ring carbon atom.

Particular examples of ring B when represented by ring B-1 include the structures:

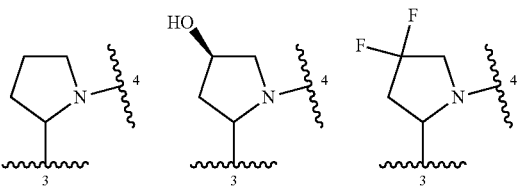 [SMILES: *C1CCCN1* ; *C1C[C@@H](O)CN1* ; *C1CC(F)(F)CN1*]

In one embodiment of Formula I, ring B is ring B-2 having the formula:

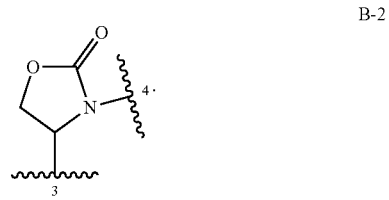

B-2

In one embodiment, m is 0.
In one embodiment, m is 1.
In one embodiment, m is 2.

One embodiment of this invention provides compounds of the general Formula I or pharmaceutically acceptable salts or solvates thereof, wherein:

ring B is ring B-1:

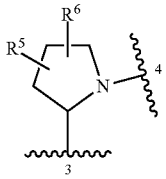

B-1 ring A is selected from rings A-1. A-2 and A-3 having the structures:

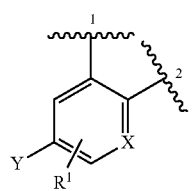

A-1

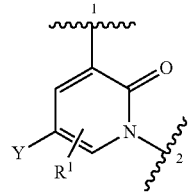

A-2 ring A is selected from rings A-1, A-2 and A-3 having the structures:

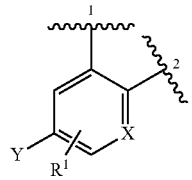

A-1

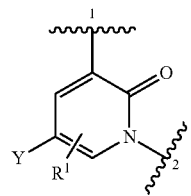

A-2

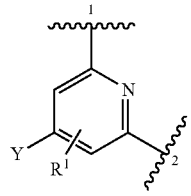

A-3

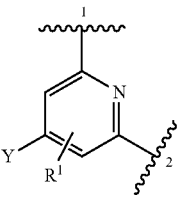

wherein the wavy line labeled 1 indicates the point of attachment of ring A to the pyrrolidine ring of Formula I and the wavy line labeled 2 indicates the point of attachment of ring A to W;
X is N or CH;
Y is H or F;
$R^1$ is H, (1-3C)alkoxy or halogen;
W is O, NH or $CH_2$, wherein when ring A is A-2, then W is $CH_2$;
m is 0, 1 or 2;
D is carbon;
$R^2$ and $R^{2a}$ are independently H, F, (1-3 C)alkyl or OH, provided that $R^2$ and $R^{2a}$ are not both OH;
$R^3$ and $R^{3a}$ are independently H, (1-3 C)alkyl or hydroxy (1-3 C)alkyl;
or $R^2$ and $R^3$ are absent and $R^{2a}$ and $R^{3a}$ together with the atoms to which they are attached form a bivalent 5-6 membered heteroaryl ring having 1-2 ring nitrogen atoms;
Z is *—$NR^{4a}$C(=O)—, *—ONHC(=O)—, *—$NR^{4b}CH_2$— or *—OC(=O)—, wherein the asterisk indicates the point of attachment of Z to the carbon bearing $R^3$;
$R^{4a}$ is H, (1-6C)alkyl, fluoro(1-6C)alkyl, difluoro(1-6C) alkyl, trifluoro(1-6C)alkyl, hydroxy(1-6C alkyl) or dihydroxy(2-6C alkyl);
$R^{4b}$ is H, (1-6C)alkyl, fluoro(1-6C)alkyl, difluoro(1-6C) alkyl, trifluoro(1-6C)alkyl, hydroxy(1-6C alkyl), dihydroxy (2-6C alkyl), (1-6C alkyl)C(O)—, (3-6C cycloalkyl)C (O)—, $Ar^1$C(O)—, $HOCH_2$C(O)—, (1-6C alkyl)sulfonyl, (3-6C cycloalkyl)sulfonyl, $Ar^2(SO_2)$—, $HO_2CCH_2$— or (1-6C alkyl)NH(CO)—;
$Ar^1$ is phenyl optionally substituted with one or more substituents independently selected from halogen, (1-6C) alkyl, and (1-6C)alkoxy;
$Ar^2$ is phenyl optionally substituted with one or more substituents independently selected from halogen, (1-6C) alkyl, and (1-6C)alkoxy; and
$R^5$ and $R^6$ are independently H, halogen, OH, (1-6C)alkyl or hydroxy(1-6C)alkyl.

One embodiment of this invention provides compounds of the general Formula IA

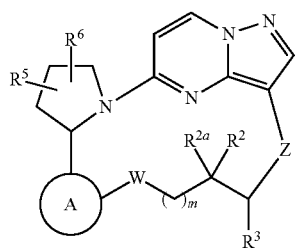

IA or pharmaceutically acceptable salts or solvates thereof, wherein:
ring A is selected from rings A-1, A-2 and A-3 having the structures:

wherein the wavy line labeled 1 indicates the point of attachment of ring A to the pyrrolidine ring of Formula I and the wavy line labeled 2 indicates the point of attachment of ring A to W;
X is N or CH;
Y is H or F;
$R^1$ is H, (1-3C)alkoxy or halogen;
W is O, NH or $CH_2$, wherein when ring A is A-2, then W is $CH_2$;
m is 0, 1 or 2;
$R^2$ and $R^{2a}$ are independently H, F, or OH, provided that $R^2$ and $R^{2a}$ are not both OH;
$R^3$ is H, (1-3 C)alkyl or hydroxy(1-3 C)alkyl;
Z is *—$NR^{4a}$C(=O)—, *—ONHC(=O)—, *—$NR^{4b}CH_2$— or *—OC(=O)—, wherein the asterisk indicates the point of attachment of Z to the carbon bearing $R^3$;
$R^{4a}$ is H, (1-6C)alkyl, fluoro(1-6C)alkyl, difluoro(1-6C) alkyl, trifluoro(1-6C)alkyl, hydroxy(1-6C alkyl) or dihydroxy(2-6C alkyl);
$R^{4b}$ is H, (1-6C)alkyl, fluoro(1-6C)alkyl, difluoro(1-6C) alkyl, trifluoro(1-6C)alkyl, hydroxy(1-6C alkyl), dihydroxy (2-6C alkyl), (1-6C alkyl)C(O)—, (3-6C cycloalkyl)C (O)—, $Ar^1$C(O)—, $HOCH_2$C(O)—, (1-6C alkyl)sulfonyl, (3-6C cycloalkyl)sulfonyl, $Ar^2(SO_2)$—, $HO_2CCH_2$— or (1-6C alkyl)NH(CO)—;
$Ar^1$ is phenyl optionally substituted with one or more substituents independently selected from halogen, (1-6C) alkyl, and (1-6C)alkoxy;
$Ar^2$ is phenyl optionally substituted with one or more substituents independently selected from halogen, (1-6C) alkyl, and (1-6C)alkoxy; and
$R^5$ and $R^6$ are independently H, halogen, OH, (1-6C)alkyl or hydroxy(1-6C)alkyl.

In one embodiment, Formula IA includes compounds wherein:
ring A is ring A-1 represented by the structure

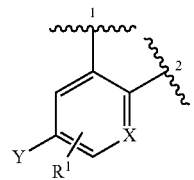

A-1 wherein the wavy line labeled 1 indicates the point of attachment of ring A to the pyrrolidine ring of Formula I and the wavy line labeled 2 indicates the point of attachment of ring A to W;
ring B is ring B-1 represented by the structure:

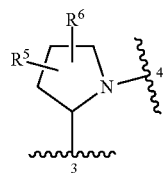

B-1 wherein the wavy line labeled 3 indicates the point of attachment to ring A and the wavy line labeled 4 indicates the point of attachment to the pyrazolo[1,5-a]pyrimidine ring of Formula I;
X is N or CH;
Y is H or F;
$R^1$ is H, (1-3C)alkyl, (1-3C)alkoxy or halogen;
W is O or NH;
m is 0, 1 or 2;
$R^2$ and $R^{2a}$ are independently H, F, or OH, provided that $R^2$ and $R^{2a}$ are not both OH;
$R^3$ is H, (1-3 C)alkyl or hydroxy(1-3 C)alkyl;
Z is *—$NR^{4a}C(=O)$—, *—$ONHC(=O)$—, or *—$OC(=O)$—, wherein the asterisk indicates the point of attachment to the carbon bearing $R^3$;
$R^{4a}$ is H, (1-6C)alkyl, fluoro(1-6C)alkyl, difluoro(1-6C)alkyl, trifluoro(1-6C)alkyl, hydroxy(1-6C alkyl) or dihydroxy(1-6C alkyl); and
$R^5$ and $R^6$ are independently H, halogen, OH, (1-6C)alkyl or hydroxy(1-6C)alkyl.
In one embodiment, X is N. In one embodiment, X is CH.
In one embodiment, Formula IA includes compounds wherein:
ring A is ring A-2 represented by the structure

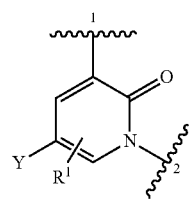

A-2 wherein the wavy line labeled 1 indicates the point of attachment of ring A to the pyrrolidine ring of Formula I and the wavy line labeled 2 indicates the point of attachment of ring A to W;
ring B is ring 1-1 represented by the structure:

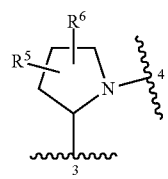

B-1 wherein the wavy line labeled 3 indicates the point of attachment to ring A and the wavy line labeled 4 indicates the point of attachment to the pyrazolo[1,5-a]pyrimidine ring of Formula I;
Y is H or F;
$R^1$ is H, (1-3C)alkyl, (1-3C)alkoxy or halogen;
m is 0, 1 or 2;
W is $CH_2$;
m is 0, 1 or 2;
$R^2$ and $R^{2a}$ are independently H, F, or OH, provided that $R^2$ and $R^{2a}$ are not both OH;
$R^3$ is H, (1-3 C)alkyl or hydroxy(1-3 C)alkyl;
Z is *—$NR^{4a}C(=O)$—, wherein the asterisk indicates the point of attachment to the carbon bearing $R^3$;
$R^{4a}$ is H, (1-6C)alkyl, fluoro(1-6C)alkyl, difluoro(1-6C)alkyl, trifluoro(1-6C)alkyl, hydroxy(1-6C alkyl) or dihydroxy(1-6C alkyl); and
$R^5$ and $R^6$ are independently H, halogen, OH, (1-6C)alkyl or hydroxy(1-6C)alkyl.
In one embodiment, Formula IA includes compounds wherein:
ring A is ring A-3 represented by the structure

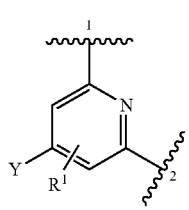

A-3 wherein the wavy line labeled 1 indicates the point of attachment of ring A to the pyrrolidine ring of Formula I and the wavy line labeled 2 indicates the point of attachment of ring A to W;
ring B is ring B-1 represented by the structure:

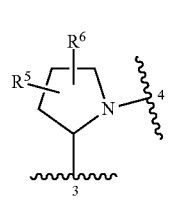

B-1 wherein the wavy line labeled 3 indicates the point of attachment to ring A and the wavy line labeled 4 indicates the point of attachment to the pyrazolo[1,5-a]pyrimidine ring of Formula I;

Y is H or F;
$R^1$ is H, (1-3C)alkyl, (1-3C)alkoxy or halogen;
W is O:
m is 0, 1 or 2;
$R^2$ and $R^{2a}$ are independently H, F, or OH, provided that $R^2$ and $R^{2a}$ are not both OH;
$R^3$ is H, (1-3 C)alkyl or hydroxy(1-3 C)alkyl;
Z is *—OC(=O)— or *—$NR^{4a}$C(=O)—, wherein the asterisk indicates the point of attachment to the carbon bearing $R^3$;
$R^{4a}$ is H, (1-6C)alkyl, fluoro(1-6C)alkyl, difluoro(1-6C)alkyl, trifluoro(1-6C)alkyl, hydroxy(1-6C alkyl) or dihydroxy(1-6C alkyl); and
$R^5$ and $R^6$ are independently H, halogen, OH, (1-6C)alkyl or hydroxy(1-6C)alkyl.

In one embodiment, Formula IA includes compounds wherein:
ring A is ring A-1 represented by the structure

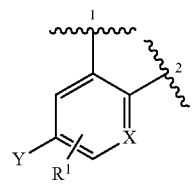

A-1 wherein the wavy line labeled 1 indicates the point of attachment of ring A to the pyrrolidine ring of Formula I and the wavy line labeled 2 indicates the point of attachment of ring A to W;
ring B is ring B-1 represented by the structure:

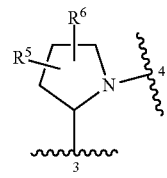

B-1 wherein the wavy line labeled 3 indicates the point of attachment to ring A and the wavy line labeled 4 indicates the point of attachment to the pyrazolo[1,5-a]pyrimidine ring of Formula I;
X is N or CH;
Y is H or F;
$R^1$ is H, (1-3C)alkyl, (1-3C)alkoxy or halogen;
W is O;
m is 0, 1 or 2;
$R^2$ and $R^{2a}$ are independently H, F, or OH, provided that $R^2$ and $R^{2a}$ are not both OH;
$R^3$ is H, (1-3 C)alkyl or hydroxy(1-3 C)alkyl;
Z is *—$NR^{4b}$$CH_2$—, wherein the asterisk indicates the point of attachment to the carbon bearing $R^3$;
$R^{4b}$ is H, (1-6C)alkyl, fluoro(1-6C)alkyl, difluoro(1-6C)alkyl, trifluoro(1-6C)alkyl (1-6C alkyl)C(O)—, (3-6C cycloalkyl)C(O)—, $Ar^1$C(O)—, $HOCH_2$C(O)—, (1-6C alkyl)sulfonyl, (3-6C cycloalkyl)sulfonyl, $Ar^2$($SO_2$)—, $HO_2CCH_2$— or (1-6C alkyl)NH(CO)—;
$Ar^1$ is phenyl optionally substituted with one or more substituents independently selected from halogen, (1-6C)alkyl, and (1-6C)alkoxy;
$Ar^2$ is phenyl optionally substituted with one or more substituents independently selected from halogen, (1-6C)alkyl, and (1-6C)alkoxy; and
$R^5$ and $R^6$ are independently H, halogen, OH, (1-6C)alkyl or hydroxy(1-6C)alkyl.

It will be appreciated that certain compounds according to the invention may contain one or more centers of asymmetry and may therefore be prepared and isolated as a mixture of isomers such as a racemic or diastereomeric mixture, or in an enantiomerically or diastereomerically pure form. It is intended that all stereoisomeric forms of the compounds of the invention, including but not limited to, diastereomers, enantiomers and atropisomers, as well as mixtures thereof such as racemic mixtures, form part of the present invention.

In one embodiment, compounds of the general Formula I wherein Ring B is ring B-1 have the absolute configuration of Fig. 1-a:

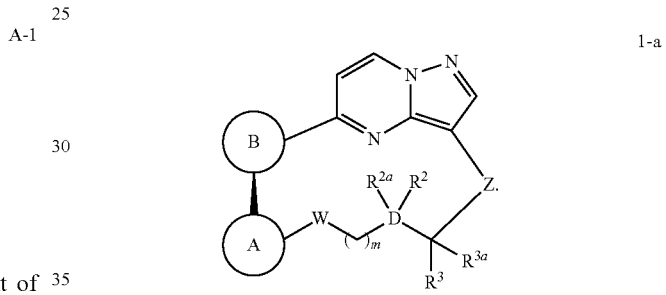

1-a

In one embodiment, compounds of the general Formula I wherein Ring B is ring B-1 have the absolute configuration of Fig. 1-b:

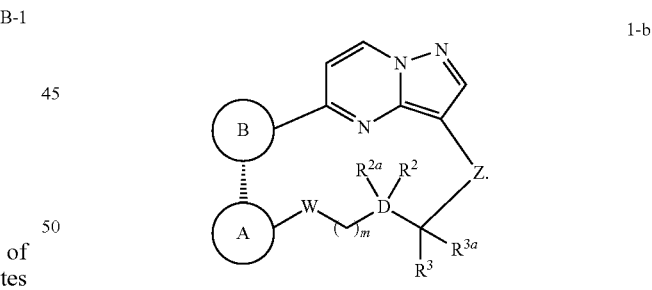

1-b

In the structures shown herein, where the stereochemistry of any particular chiral atom is not specified, then all stereoisomers are contemplated and included as the compounds of the invention. Where stereochemistry is specified by a solid wedge or dashed line representing a particular configuration, then that stereoisomer is so specified and defined.

The terms "(1-3C)alkyl" and "(1-6C)alkyl" as used herein refer to saturated linear or branched-chain monovalent hydrocarbon radicals of one to three carbon atoms and one to six carbon atoms, respectively. Examples include, but are not limited to, methyl, ethyl, 1-propyl, isopropyl, 1-butyl, isobutyl, sec-butyl, tert-butyl, 2-methyl-2-propyl, pentyl, and hexyl.

The term "fluoro(1-6C)alkyl" as used herein refers to saturated linear or branched-chain monovalent hydrocarbon radicals of one to six carbon atoms as defined herein, wherein one of the hydrogens is replaced by a fluorine atom.

The term "difluoro(1-6C)alkyl" as used herein refers to saturated linear or branched-chain monovalent hydrocarbon radicals of one to six carbon atoms as defined herein, wherein two of the hydrogens are replaced by fluorine atoms.

The term "trifluoro(1-6C)alkyl" as used herein refers to saturated linear or branched-chain monovalent hydrocarbon radicals of one to six carbon atoms as defined herein, wherein three of the hydrogens are replaced by fluorine atoms.

The term "hydroxy(1-6Calkyl) as used herein refers to saturated linear or branched-chain monovalent hydrocarbon radicals of one to six carbon atoms, wherein one of the hydrogens is replaced by a hydroxy (OH) group.

The term "dihydroxy(1-6Calkyl) as used herein refers to saturated linear or branched-chain monovalent hydrocarbon radicals of one to six carbon atoms as defined herein, wherein two of the hydrogens are replaced by hydroxy (OH) groups, provided the hydroxy groups are not on the same carbon atom.

The term "(1-6C alkyl)sulfonyl" as used herein refers to a (1-6C alkyl)$SO_2$— group, wherein the radical is on the sulfur atom and the (1-6C alkyl) portion is as defined above. Examples include methylsulfonyl ($CH_3SO_2$—) and ethylsulfonyl ($CH_3CH_2SO_2$—).

The term "(3-6C cycloalkyl)sulfonyl" as used herein refers to a (3-6C cycloalkyl)$SO_2$— group, wherein the radical is on the sulfur atom. An example is cyclopropylsulfonyl.

The terms "(1-4C)alkoxy" and "(1-6C)alkoxy", as used herein refer to saturated linear or branched-chain monovalent alkoxy radicals of one to four carbon atoms or one to six carbon atoms, respectively, wherein the radical is on the oxygen atom. Examples include methoxy, ethoxy, propoxy, isopropoxy, and butoxy.

The term "halogen" includes fluoro, chloro, bromo and iodo.

It will also be appreciated that certain compounds of Formula I may be used as intermediates for the preparation of further compounds of Formula I.

The compounds of Formula I include salts thereof. In certain embodiments, the salts are pharmaceutically acceptable salts. In addition, the compounds of Formula I include other salts of such compounds which are not necessarily pharmaceutically acceptable salts, and which may be useful as intermediates for preparing and/or purifying compounds of Formula I and/or for separating enantiomers of compounds of Formula I.

The term "pharmaceutically acceptable" indicates that the substance or composition is compatible chemically and/or toxicologically, with the other ingredients comprising a formulation, and/or the mammal being treated therewith.

It will further be appreciated that the compounds of Formula I and their salts may be isolated in the form of solvates, and accordingly that any such solvate is included within the scope of the present invention.

Compounds of the invention may also contain unnatural proportions of atomic isotopes at one or more of the atoms that constitute such compounds. That is, an atom, in particular when mentioned in relation to a compound according to Formula I, comprises all isotopes and isotopic mixtures of that atom, either naturally occurring or synthetically produced, either with natural abundance or in an isotopically enriched form. For example, when hydrogen is mentioned, it is understood to refer to $^1H$, $^2H$, $^3H$ or mixtures thereof; when carbon is mentioned, it is understood to refer to $^{11}C$, $^{12}C$, $^{13}C$, $^{14}C$ or mixtures thereof; when nitrogen is mentioned, it is understood to refer to $^{13}N$, $^{14}N$, $^{15}N$ or mixtures thereof; when oxygen is mentioned, it is understood to refer to $^{14}O$, $^{15}O$, $^{16}O$, $^{17}O$, $^{18}O$ or mixtures thereof; and when fluoro is mentioned, it is understood to refer to $^{18}F$, $^{19}F$ or mixtures thereof. The compounds according to the invention therefore also comprise compounds with one or more isotopes of one or more atom, and mixtures thereof, including radioactive compounds, wherein one or more non-radioactive atoms has been replaced by one of its radioactive enriched isotopes. Radiolabeled compounds are useful as therapeutic agents, e.g., cancer therapeutic agents, research reagents, e.g., assay reagents, and diagnostic agents. e.g., in vivo imaging agents. All isotopic variations of the compounds of the present invention, whether radioactive or not, are intended to be encompassed within the scope of the present invention.

The present invention further provides a process for the preparation of a compound of Formula I or a salt thereof as defined herein which comprises:

(a) for a compound of Formula I wherein Z is *—NHC(=O)—, and ring A, ring B, W, D, $R^2$, $R^{2a}$, $R^3$, $R^{3a}$ and m are as defined for Formula I, cyclizing a corresponding compound having the formula II

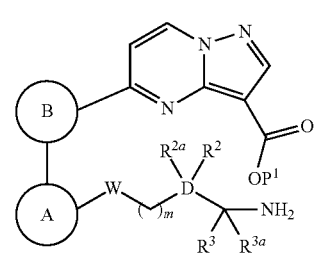

II where $P^1$ is H or a carboxyl protecting group, in the presence of a coupling reagent and a base; or (b) for a compound of Formula I wherein W is O, ring A is formula A-1:

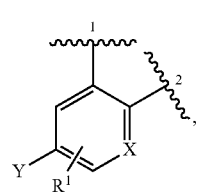

A-1

X is N, and ring B, D, Z, Y, $R^1$, $R^2$, $R^{2a}$, $R^3$, $R^{3a}$ and m are as defined for Formula I, cyclizing a corresponding compound having the formula III

III

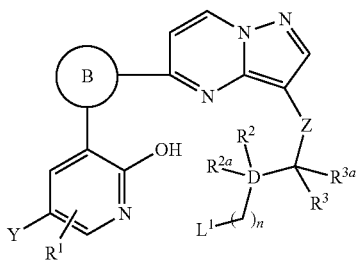

where n is 1, 2, 3 or 4 and $L^1$ is a leaving group or atom, in the presence of a base; or (c) for a compound of Formula I wherein W is CH$_2$, ring A is formula A-2:

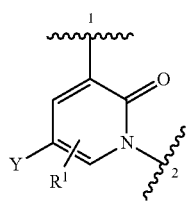

A-2 and ring B, Z, D, Y, $R^1$, $R^2$, $R^{2a}$, $R^3$, $R^{3a}$ and m are as defined for Formula I, cyclizing a corresponding compound having the formula IV

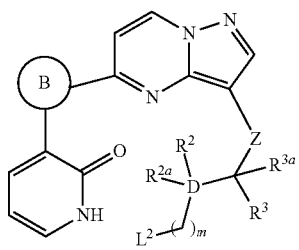

IV where $L^2$ is a leaving group or atom, in the presence of a base; or (d) for a compound of Formula I wherein Z is *—NHC(=O)—, and ring A, ring B, W, D, $R^2$, $R^{2a}$, $R^3$, $R^{3a}$ and m are as defined for Formula I, cyclizing a corresponding compound having the formula V

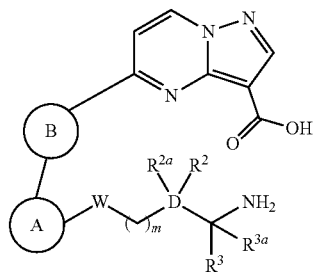

V in the presence of a base and a coupling reagent; or (c) for a compound of Formula I wherein Z is *—NHCH$_2$—, and ring A, ring B, W, D, $R^2$, $R^{2a}$, $R^3$, $R^{3a}$ and m are as defined for Formula I, cyclizing a corresponding compound having the formula VI

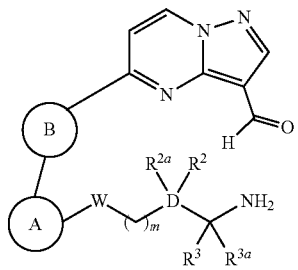

VI in the presence of a reducing agent; or (f) for a compound of Formula I wherein Z is *—NHCH$_2$—, and ring A, ring B, W, D, $R^2$, $R^{2a}$, $R^3$, $R^{3a}$ and m are as defined for Formula I, cyclizing a corresponding compound having the formula VII

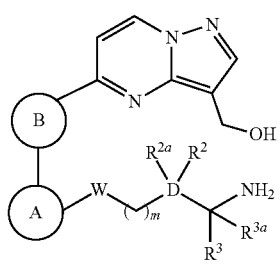

VII in the presence of triphenylphosphine; or (g) for a compound of Formula I wherein ring A, ring B, W, D, m, $R^2$, $R^{2a}$, $R^3$, and $R^{3a}$ are as defined for Formula I, Z is *—NR$^{4b}$CH$_2$—, and R$^{4b}$ is (1-6C alkyl)C(O)—, (3-6C cycloalkyl)C(O)—, Ar$^1$C(O)—, HOCH$_2$C(O)—, (1-6C alkyl)sulfonyl, (3-6C cycloalkyl)sulfonyl, (1-6C alkyl)sulfonyl, (3-6C cycloalkyl)sulfonyl, or Ar$^2$(SO$_2$)—, coupling a corresponding compound having the formula VIII

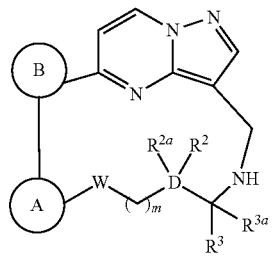

VIII with a reagent having the formula (1-6C alkyl)C(O)-L$^3$, (3-6C cycloalkyl)C(O)-L$^3$, Ar$^1$C(O)-L$^3$, HOCH$_2$C(O)-L$^3$, (1-6C alkyl)(SO$_2$)-L$^3$, (3-6C cycloalkyl)(SO$_2$)-L$^3$, or Ar$^2$(SO$_2$)-L$^3$, respectively, where L$^3$ is a leaving atom, in the presence of a base; or (h) for a compound of Formula I wherein ring A, ring B, W, D, $R^2$, $R^{2a}$, $R^3$, $R^{3a}$ and m are as defined for Formula I, Z is *—NR$^{4b}$CH$_2$—, and R$^{4b}$ is (1-6C alkyl)NH(CO)—, reacting a compound having the formula VIII

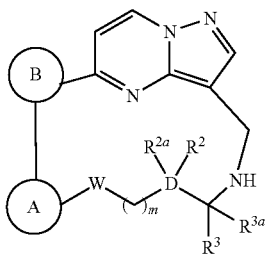

VIII with a reagent having the formula (1-6C alkyl)N=C=O in the presence of a base; or (i) for a compound of Formula I wherein $R^1$ is F, $R^{2a}$ is H, and ring A, ring B, Z, W, D, $R^3$, $R^{3a}$, and m are as defined for Formula I, reacting a corresponding compound having the formula IX

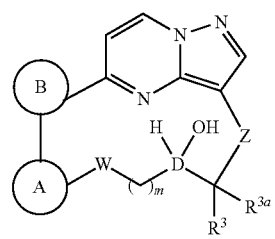

IX with a fluorination reagent;

(j) for a compound of Formula I wherein W is O, ring A is formula A-1,

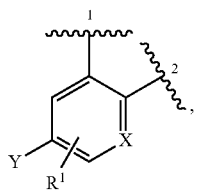

A-1

X is CH, and Y, $R^1$, D, ring B, Z, $R^2$, $R^{2a}$, $R^3$ and m are as defined for Formula I, cyclizing a corresponding compound having the formula X

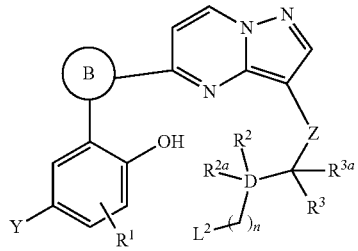

X where n is 1, 2, 3 or 4 and $L^1$ is a leaving group or atom, in the presence of a base; and optionally removing any protecting groups and optionally preparing a salt thereof.

In one embodiment of the above-described methods (a)-(j), ring B is ring B-1 having the structure:

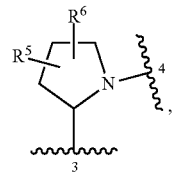

B-1

D is carbon, $R^2$ and $R^{2a}$ are independently H, F, (1-3 C)alkyl or OH (provided that $R^2$ and $R^{2a}$ are not both OH), $R^3$ is H, (1-3 C)alkyl or hydroxy(1-3 C)alkyl, and ring A, W, m, Z, $R^5$ and $R^6$ are as defined for Formula I.

Referring to method (a), the cyclization may be performed using conventional amide bond formation conditions, for example by treating the carboxylic acid with an activating agent, followed by addition of the amine in the presence of a base. Suitable activating agents include EDCI, oxalyl chloride, thionyl chloride, HATU, and HOBt. Suitable bases include amine bases, for example triethylamine, diisopropylethylamine, pyridine, or excess ammonia. Suitable solvents include DCM, DCE, THF and DMF.

Referring to methods (b) and (c), the leaving atoms $L^1$ and $L^2$ may be, for example a halogen atom such as Br, Cl or I. Alternatively, $L^1$ and $L^2$ can be a leaving group, for example an arylsulfonyloxy group or an alkylsulfonyloxy group, such as a mesylate or a tosylate group. Suitable bases include alkali metal carbonates, such as sodium carbonate, potassium carbonate or cesium carbonate. Convenient solvents include aprotic solvents such as ethers (for example tetrahydrofuran or p-dioxane), DMF, or acetone. The reaction can be conveniently performed at elevated temperatures, for example 50-150° C., for example at 85° C.

Referring to method (d), suitable coupling reagents include HATU, HBTU, TBTU, DCC, DIEC, and any other amide coupling reagents well known to persons skilled in the art. Suitable bases include tertiary amine bases such as DIEA and triethylamine. Convenient solvents include DMF, THF, DCM and DCE.

Referring to method (e), suitable reducing agents include $Me_4N(OAc)_3BH$, $Na(OAc)_3BH$ and $NaCNBH_3$. Suitable solvents include neutral solvents such as acetonitrile, THF and DCE. The reaction can be conveniently performed at ambient temperature.

Referring to method (f), in certain embodiments the triphenylphosphine reagent is used in the form of a polystyrene-bound $PPh_3$ resin (sold as PS-$PPh_3$ by Biotage Systems). The reaction is conveniently performed at ambient temperature. Suitable solvents include neutral solvents, for example DCM.

Referring to method (g), the leaving atom $L^3$ may be a halogen, for example Cl or Br. Suitable bases include tertiary amine bases such as diisopropylethylamine and triethylamine. The reaction is conveniently performed at ambient temperature.

Referring to method (h), suitable bases include tertiary amine bases such as DIEA and triethylamine. The reaction is conveniently performed at ambient temperature.

Referring to method (i), the fluorination reagent may be, for example, bis(2-methoxyethyl)amino-sulfur trifluoride (Deoxo-Fluor™) or diethylaminosulfur trifluoride (DAST). Suitable solvents include dichloromethane, chloroform, dichloroethane, and toluene. The reaction is conveniently performed at ambient temperature.

Referring to method (j), base may be, for example, an alkali metal carbonate, such as for example sodium carbonate, potassium carbonate or cesium carbonate. Convenient solvents include aprotic solvents such as ethers (for example tetrahydrofuran or p-dioxane) or toluene. The reaction can be conveniently performed at a temperature between ambient temperature and reflux, for example at 85° C.

Amine groups in compounds described in any of the above methods may be protected with any convenient amine protecting group, for example as described in Greene & Wuts, eds., "Protecting Groups in Organic Synthesis", $2^{nd}$ ed. New York; John Wiley & Sons, Inc., 1991. Examples of amine protecting groups include acyl and alkoxycarbonyl groups, such as t-butoxycarbonyl (BOC), and [2-(trimethylsilyl)ethoxy]methyl (SEM). Likewise, carboxyl groups may be protected with any convenient carboxyl protecting group, for example as described in Greene & Wuts, eds., "Protecting Groups in Organic Synthesis", $2^{nd}$ ed. New York; John Wiley & Sons, Inc., 1991. Examples of carboxyl protecting groups include (1-6C)alkyl groups, such as methyl, ethyl and t-butyl. Alcohol groups may be protected with any convenient alcohol protecting group, for example as described in Greene & Wuts, eds., "Protecting Groups in Organic Synthesis", $2^{nd}$ ed. New York; John Wiley & Sons, Inc., 1991. Examples of alcohol protecting groups include benzyl, trityl, silyl ethers, and the like.

The compounds of the formulas II, III, IV, V, VI, VII, VIII, IX and X are also believed to be novel and are provided as further aspects of the invention.

The ability of compounds of the invention to act as TrkA inhibitors may be demonstrated by the assays described in Examples A and B.

Certain compounds which are inhibitors of TrkA and/or TrkB may be useful in the treatment of multiple types of pain including inflammatory pain, neuropathic pain, and pain associated with cancer, surgery, and bone fracture.

In one embodiment, compounds of Formula I are useful for treating pain, including chronic and acute pain, in a mammal.

Acute pain, as defined by the International Association for the Study of Pain, results from disease, inflammation, or injury to tissues. This type of pain generally comes on suddenly, for example, after trauma or surgery, and may be accompanied by anxiety or stress. The cause can usually be diagnosed and treated, and the pain is confined to a given period of time and severity. In some rare instances, it can become chronic.

Chronic pain, as defined by the International Association for the Study of Pain, is widely believed to represent disease itself. It can be made much worse by environmental and psychological factors. Chronic pain persists over a longer period than acute pain and is resistant to most medical treatments, generally over 3 months or more. It can and often does cause severe problems for patients.

Compounds of Formula I are also useful for treating cancer in a mammal. Particular examples include neuroblastoma, ovarian, pancreatic, colorectal and prostate cancer.

Compounds of Formula I are also useful for treating inflammation in a mammal.

Compounds of Formula I are also useful for treating certain infectious diseases in a mammal, such as *Trypanosoma cruzi* infection.

Compounds of Formula I may also be used to treat neurodegenerative diseases in a mammal. Examples of neurodegenerative disease include demyelination and dysmyelination. Additional examples of neurodegenerative diseases include multiple sclerosis, Parkinson's disease and Alzheimer's disease.

In addition, compounds of Formula I may also be used to treat interstitial cystitis (IC), painful bladder syndrome (PBS), urinary incontinence, asthma, anorexia, atopic dermatitis, and psoriasis in a mammal.

Accordingly, another embodiment of this invention provides a method of treating or preventing pain in a mammal, comprising administering to said mammal one or more compounds of Formula I or a pharmaceutically acceptable salt thereof in an amount effective to treat or prevent said pain. In one embodiment, the pain is chronic pain. In one embodiment, the pain is acute pain. In one embodiment, the pain is inflammatory pain. In one embodiment, the pain is neuropathic pain. In one embodiment, the pain is pain associated with cancer. In one embodiment, the pain is pain associated with surgery. In one embodiment, the pain is pain associated with bone fracture. In one embodiment, the method comprises a method of treating said pain in a mammal. In one embodiment, the method comprises a method of preventing said pain in a mammal.

Another embodiment of this invention provides a method of treating or preventing inflammation in a mammal, comprising administering to said mammal one or more compounds of Formula I or a pharmaceutically acceptable salt thereof in an amount effective to treat or prevent said inflammation. In one embodiment, the method comprises a method of treating said inflammation in a mammal. In one embodiment, the method comprises a method of preventing said inflammation in a mammal.

Another embodiment of this invention provides a method of treating or preventing a neurodegenerative disease in a mammal, comprising administering to said mammal one or more compounds of Formula I or a pharmaceutically acceptable salt thereof in an amount effective to treat or prevent said neurodegenerative disease. In one embodiment, the neurodegenerative disease is demyelination. In one embodiment, the neurodegenerative disease is dysmyelination. In one embodiment, the neurodegenerative disease is multiple sclerosis. In one embodiment, the neurodegenerative disease is Parkinson's disease. In one embodiment, the neurodegenerative disease is Alzheimer's disease. Another embodiment of this invention provides a method of treating or preventing infectious diseases in a mammal, comprising administering to said mammal one or more compounds of Formula I or a pharmaceutically acceptable salt thereof in an amount effective to treat or prevent said infectious disease. In one embodiment, the infectious disease is *Trypanosoma cruzi* infection. In one embodiment, the method comprises a method of treating said neurodegenerative disease in a mammal. In one embodiment, the method comprises a method of preventing said neurodegenerative disease in a mammal.

Another embodiment of this invention provides a method of treating or preventing cancer in a mammal, comprising administering to said mammal one or more compounds of Formula I or a pharmaceutically acceptable salt thereof in an amount effective to treat or prevent said cancer. In one embodiment, the cancer is neuroblastoma. In one embodiment, the cancer is ovarian cancer. In one embodiment, the cancer is pancreatic cancer. In one embodiment, the cancer is colorectal cancer. In one embodiment, the cancer is prostate cancer. In one embodiment, the method comprises a method of treating said cancer in a mammal. In one embodiment, the method comprises a method of preventing said cancer in a mammal.

Compounds of Formula I may be administered alone as a sole therapy or can be administered in addition with one or more other substances and/or treatments that work by the same or a different mechanism of action. Examples include anti-inflammatory compounds, steroids (e.g., dexamethasone, cortisone and fluticasone), analgesics such as NSAIDs (e.g., aspirin, ibuprofen, indomethacin, and ketoprofen), and opioids (such as morphine), and chemotherapeutic agents. These agents may be administered with one or more compounds of Formula I as part of the same or separate dosage forms, via the same or different routes of administration, and on the same or different administration schedules according to standard pharmaceutical practice known to one skilled in the art.

In the field of medical oncology it is normal practice to use a combination of different forms of treatment to treat each patient with cancer. In medical oncology the other component(s) of such conjoint treatment in addition to compositions of the present invention may be, for example, surgery, radiotherapy, chemotherapy, signal transduction inhibitors and/or monoclonal antibodies.

Accordingly, the compounds of Formula I may be administered in combination with one or more agents selected from mitotic inhibitors, alkylating agents, anti-metabolites, antisense DNA or RNA, intercalating antibiotics, growth factor inhibitors, signal transduction inhibitors, cell cycle inhibitors, enzyme inhibitors, retinoid receptor modulators, proteasome inhibitors, topoisomerase inhibitors, biological response modifiers, anti-hormones, angiogenesis inhibitors, cytostatic agents anti-androgens, targeted antibodies, HMG-CoA reductase inhibitors, and prenyl-protein transferase inhibitors. These agents may be administered with one or more compounds of Formula I as part of the same or separate dosage forms, via the same or different routes of administration, and on the same or different administration schedules according to standard pharmaceutical practice known to one skilled in the art.

As used herein, terms "treat" or "treatment" refer to therapeutic, prophylactic, palliative or preventative measures. Beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder, as well as those prone to have the condition or disorder or those in which the condition or disorder is to be prevented.

In one embodiment, the terms "treatment" or "treating" as used herein, mean an alleviation, in whole or in part, of symptoms associated with a disorder or condition as described herein (e.g., multiple types of pain including inflammatory pain, neuropathic pain, and pain associated with cancer, surgery, and bone fracture), or slowing, or halting of further progression or worsening of those symptoms.

In one embodiment, the term "preventing" as used herein means the prevention of the onset, recurrence or spread, in whole or in part, of the disease or condition as described herein (e.g., multiple types of pain including inflammatory pain, neuropathic pain, and pain associated with cancer, surgery, and bone fracture), or a symptom thereof.

The terms "effective amount" and "therapeutically effective amount" refer to an amount of compound that, when administered to a mammal in need of such treatment, is sufficient to (i) treat or prevent a particular disease, condition, or disorder, (ii) attenuate, ameliorate, or eliminate one or more symptoms of the particular disease, condition, or disorder, or (iii) prevent or delay the onset of one or more symptoms of the particular disease, condition, or disorder described herein. The amount of a compound of Formula I that will correspond to such an amount will vary depending upon factors such as the particular compound, disease condition and its severity, the identity (e.g., weight) of the mammal in need of treatment, but can nevertheless be routinely determined by one skilled in the art.

As used herein, the term "mammal" refers to a warm-blooded animal that has or is at risk of developing a disease described herein and includes, but is not limited to, guinea pigs, dogs, cats, rats, mice, hamsters, and primates, including humans.

Compounds of the invention may be administered by any convenient route, e.g. into the gastrointestinal tract (e.g. rectally or orally), the nose, lungs, musculature or vasculature, or transdermally or dermally. Compounds may be administered in any convenient administrative form, e.g. tablets, powders, capsules, solutions, dispersions, suspensions, syrups, sprays, suppositories, gels, emulsions, patches etc. Such compositions may contain components conventional in pharmaceutical preparations, e.g. diluents, carriers, pH modifiers, sweeteners, bulking agents, and further active agents. If parenteral administration is desired, the compositions will be sterile and in a solution or suspension form suitable for injection or infusion. Such compositions form a further aspect of the invention.

The present invention further provides a pharmaceutical composition, which comprises a compound of Formula I or a pharmaceutically acceptable salt thereof, as defined hereinabove. In one embodiment, the pharmaceutical composition includes the compound of Formula I together with a pharmaceutically acceptable diluent or carrier.

The present invention further provides a compound of Formula I or a pharmaceutically acceptable salt thereof, for use in therapy.

In one embodiment, the invention provides a compound of Formula I or a pharmaceutically acceptable salt thereof, for use in the treatment of pain in a mammal. In one embodiment, the pain is chronic pain. In one embodiment, the pain is acute pain. In one embodiment, the pain is inflammatory pain. In one embodiment, the pain is neuropathic pain. In one embodiment, the pain is pain associated with cancer. In one embodiment, the pain is pain associated with surgery. In one embodiment, the pain is pain associated with bone fracture.

In one embodiment, the invention provides a compound of Formula I or a pharmaceutically acceptable salt thereof, for use in the treatment of inflammation in a mammal.

According to a further aspect, the present invention provides a compound of Formula I or a pharmaceutically acceptable salt thereof, for use in the treatment of a neurodegenerative disease in a mammal. In one embodiment, the neurodegenerative disease is demyelination. In one embodiment, the neurodegenerative disease is dysmyelination. In one embodiment, the neurodegenerative disease is multiple sclerosis. In one embodiment, the neurodegenerative disease is Parkinson's disease. In one embodiment, the neurodegenerative disease is Alzheimer's disease.

In one embodiment, the invention provides a compound of Formula I or a pharmaceutically acceptable salt thereof, for use in the treatment of infectious diseases in a mammal. In one embodiment, the infectious disease is *Trypanosoma cruzi* infection.

In one embodiment, the invention provides a compound of Formula I or a pharmaceutically acceptable salt thereof, for use in the treatment of cancer in a mammal. In one embodiment, the cancer is neuroblastoma. In one embodiment, the cancer is ovarian cancer. In one embodiment, the cancer is pancreatic cancer. In one embodiment, the cancer is colorectal cancer. In one embodiment, the cancer is prostate cancer.

Another embodiment of the present invention provides the use of a compound of Formula I, or a pharmaceutically acceptable salt thereof, in the manufacture of a medicament for the treatment of pain in a mammal.

Another embodiment of the present invention provides the use of a compound of Formula I, or a pharmaceutically acceptable salt thereof, in the manufacture of a medicament for the treatment of inflammation in a mammal.

Another embodiment of the present invention provides the use of a compound of Formula I, or a pharmaceutically acceptable salt thereof, in the manufacture of a medicament for the treatment of a neurodegenerative disease in a mammal.

Another embodiment of the present invention provides the use of a compound of Formula I, or a pharmaceutically acceptable salt thereof, in the manufacture of a medicament for the treatment of infectious diseases in a mammal.

Another embodiment of the present invention provides the use of a compound of Formula I, or a pharmaceutically acceptable salt thereof, in the manufacture of a medicament for the treatment of cancer in a mammal.

EXAMPLES

The following examples illustrate the invention. In the examples described below, unless otherwise indicated all temperatures are set forth in degrees Celsius. Reagents were purchased from commercial suppliers such as Aldrich Chemical Company, Lancaster, Alfa, Aesar, TCI, Maybridge, Asta Tech, or other suitable suppliers, and were used without further purification unless otherwise indicated. THF, DCM, toluene, DMF and dioxane were purchased from Aldrich in Sure/Seal™ bottles and used as received.

The reactions set forth below were done generally under a positive pressure of nitrogen or argon or with a drying tube (unless otherwise stated) in anhydrous solvents, and the reaction flasks were typically fitted with rubber septa for the introduction of substrates and reagents via syringe. Glassware was oven dried and/or heat dried or dried under a stream of dry nitrogen.

Column chromatography was done on a Biotage system (Manufacturer: Dyax Corporation) having a silica gel or C-18 reverse phase column, or on a silica SepPak cartridge (Waters), or using conventional flash column chromatography on silica gel, unless otherwise specified.

Abbreviations used herein have the following meanings:

| | |
|---|---|
| CAN | acetonitrile |
| APCI | Atmospheric Pressure Chemical Ionization |
| BINAP | 2,2'-bis(diphenylphosphino)-1,1'-binaphthyl |
| Boc | tert-butoxycarbonyl |
| Boc$_2$O | Di-tert-butyl dicarbonate |
| BOP | (Benzotriazol-1-yloxy)tris(dimethylamino)phosphonium hexafluorophosphate |
| CDI | carbonyl diimidazole |
| DCC | N,N'-dicyclohexylcarbodiimide |
| DCE | Dichloroethane |
| DCM | Dichloromethane |
| DIEA | Diisopropylethylamine |
| DIEC | 1-(3-dimethylaminopropyl)-3-ethylcarboiimide |
| DIPHOS | 1,2-Bis(Diphenylphosphino)ethane |
| DMF | N,N-Dimethylformamide |
| DMSO | dimethylsulfoxide |
| EDCI | 1-ethyl-3-(3-dimethylaminopropyl) carbodiimide) |
| HATU | (2-(7-Aza-1H-benzotriazole-1-yl)-1,1,3,3-tetramethyluronium hexafluorophosphate) |
| HOBt | Hydroxybenzotriazole |
| IPA | Isopropyl alcohol |
| MTBE | tert-butyl-methylether |
| Pd(PPh$_3$)$_4$ | Tetrakis(triphenylphosphine)palladium (0) |
| Pd$_2$dba$_3$ | Tris(dibenzylideneacetone)dipalladium (0) |
| PS-PPh$_3$ | polystyrene-bound PPh$_3$ resin |
| TEA | triethylamine |
| TFA | Trifluoroacetic acid |
| THF | Tetrahydrofuran |
| TLC | Thin layer chromatography |

Biological Assays

Example A

TrkA ELISA Assay

An enzyme-linked immunosorbant assay (ELISA) was used to assess TrkA kinase activity in the presence of inhibitors. Immulon 4HBX 384-well microtiter plates (Thermo part #8755) were coated with a 0.025 mg/mL solution of poly (Glu, Ala, Tyr; 6:3:1; Sigma P3899). Various concentrations of test compound, 2.5 nM TrkA (Invitrogen Corp., histidine-tagged recombinant human TrkA, cytoplasmic domain), and 500 μM ATP were incubated for 25 minutes at ambient temperature in the coated plates while shaking. The assay buffer consisted of 25 mM MOPS pH 7.5, 0.005% (v/v) Triton X-100 and 5 mM MgCl$_2$. The reaction mixture was removed from the plate by washing with PBS containing 0.1% (v/v) Tween 20. The phosphorylated reaction product was detected using 0.2 μg/mL of a phosphotyrosine specific monoclonal antibody (clone PY20) conjugated to horseradish peroxidase in conjunction with the TMB Peroxidase Substrate System (KPL). After the addition of 1M phosphoric acid, the chromogenic substrate color intensity was quantitated via absorbance at 450 nm. IC$_{50}$ values were calculated using either a 4 or 5-parameter logistic curve fit.

Table 1 provides averaged IC$_{50}$ values for compounds of the invention when tested in this assay. In Table 1, the letter "A" designates an IC$_{50}$ value between about 1 and 100 nM, and the letter "B" designates an IC$_{50}$ value >100 nM and <3000 nM.

Example B

TrkA Binding Assay

The ability of a compound to bind to TrkA was measured by Invitrogen's LanthaScreen™ Eu Kinase Binding Assay. In this assay, His-tagged recombinant human TrkA (cytoplasmic domain) from Invitrogen is incubated with Invitrogen's Alexa-Fluor® Tracer 236, biotinylated anti-His, and europium-labeled Streptavidin, compound (2% DMSO final) in buffer (25 mM MOPS, pH 7.5, 5 mM MgCl2, 0.005% Triton X-100). After a 60-minute incubation at 22°

C., the reaction was measured using the EnVision via TR-FRET dual wavelength detection, and the POC was calculated from the emission ratio. The compound dose response data was fit to a 4-parameter logistic model and $IC_{50}$ was defined as the concentration of compound at 50 POC.

Table 1 provides averaged $IC_{50}$ values for compounds of the invention when tested in this assay. In Table 1, the letter "A" designates an $IC_{50}$ value between about 1 and 100 nM, and the letter "B" designates an $IC_{50}$ value >100 nM and <3000 nM.

TABLE 1

| Example No. | TrkA Elisa Enzyme Assay $IC_{50}$ | TrkA Binding Assay $IC_{50}$ |
| --- | --- | --- |
| 1 | A | A |
| 2 | A | A |
| 3 | A | A |
| 4 | A | A |
| 5 | A | A |
| 6 | A | A |
| 7 | A | A |
| 8 | A | A |
| 9 | A | A |
| 10 | A | A |
| 11 | A | A |
| 12 | A | |
| 13 | A | |
| 14 | A | |
| 15 | B | |
| 16 | A | A |
| 17 | A | |
| 18 | A | A |
| 19 | A | A |
| 20 | A | A |
| 21 | B | |
| 22 | A | |
| 23 | A | A |
| 24 | B | |
| 25 | A | |
| 26 | B | B |
| 27 | A | |
| 28 | A | |
| 29 | A | |
| 30 | A | |
| 31 | B | B |
| 32 | A | |
| 33 | A | |
| 34 | A | |
| 35 | A | |
| 36 | A | |
| 37 | A | |
| 38 | A | |
| 39 | A | |
| 40 | A | |
| 41 | A | |
| 41-B | | B[1] |
| 42 | A | |
| 42-B | | B[1] |
| 43 | A | |
| 43-B | | B[1] |
| 44 | A | |
| 44-B | | A[1] |
| 45 Diastereomer 1 | | A[1] |
| 45 Diastereomer 2 | | A[1] |

[1]Compound may have been isolated along with the enantiomer and/or one or more diastereomers, which additional isomer(s) were believed to make up ≤1.5% of the total amount isolated.

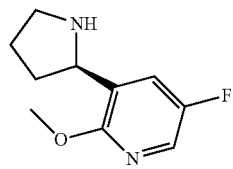

Preparation A (R)-5-fluoro-2-methoxy-3-(pyrrolidin-2-yl)pyridine

Step A: Preparation of (R)-tert-butyl 2-(5-fluoro-2-methoxypyridin-3-yl)pyrrolidine-1-carboxylate A solution of tert-butyl pyrrolidine-1-carboxylate (4.09 mL, 23.4 mmol) and (−)-sparteine (6.44 mL, 28.0 mmol) in MTBE (50 mL) was cooled to −78° C. and sec-BuLi (20 mL, 28.0 mmol, 1.4M in cyclohexane) was introduced drop-wise by cannula, keeping the internal temperature under −78° C. The resulting solution was stirred for 3 hours at −78° C., followed by addition of a solution of $ZnCl_2$ (21.0 mL, 21.0 mmol, 1M in $Et_2O$) drop-wise with rapid stirring, keeping the internal temperature below −65° C. The resulting light suspension was stirred at −78° C. for 10 minutes and then warmed to ambient temperature. The resulting mixture was sequentially charged with 3-bromo-5-fluoro-2-methoxy-pyridine (5.05 g, 24.5 mmol), $Pd(OAc)_2$ (0.262 g, 1.17 mmol) and $t-Bu_3P-HBF_4$ (0.407 g, 1.40 mmol) in one portion. After stirring overnight at ambient temperature, concentrated $NH_4OH$ (1 mL) was added and the reaction was stirred for 1 hour. The resulting slurry was filtered through Celite® and washed with $Et_2O$. The organic layer was filtered and concentrated, and the crude product was purified by silica column chromatography, eluting with 5% EtOAc/hexanes to give product (R)-tert-butyl 2-(5-fluoro-2-methoxypyridin-3-yl)pyrrolidine-1-carboxylate as yellow oil (4.34 g, 63% yield).

Step B: Preparation of (R)-5-fluoro-2-methoxy-3-(pyrrolidin-2-yl)pyridine

A DCM (12 mL) solution of TFA (11.3 mL, 146 mmol) was added to (R)-tert-butyl 2-(5-fluoro-2-methoxypyridin-3-yl)pyrrolidine-1-carboxylate (4.33 g, 14.6 mmol) and stirred at ambient temperature for 1 hour. The reaction was then concentrated, taken up in EtOAc, then washed with $NaHCO_3$ and brine. The organic phase was dried ($MgSO_4$), filtered, and concentrated, and the crude material was purified by silica column chromatography eluting with a 1-2% 7N $NH_3$-MeOH/DCM to afford (R)-5-fluoro-2-methoxy-3-(pyrrolidin-2-yl)pyridine as a liquid (1.40 g, 49% yield).

The enantiomeric excess (ee %) of (R)-5-fluoro-2-methoxy-3-(pyrrolidin-2-yl)pyridine was determined as follows: To a propan-2-ol solution of small amount of ((R)-5-fluoro-2-methoxy-3-(pyrrolidin-2-yl)pyridine was added excess N-(2,4-dinitro-5-fluorophenyl)-L-alanine amide (FDAA, Marfey's reagent). The mixture was heated to reflux for approximately two minutes. After cooling to ambient temperature, the reaction mixture was diluted with acetonitrile and analyzed by HPLC (YMC ODS-AQ 4.6×50 mm 3 µm 120 Å column; mobile phase: 5-95% solvent B in A; solvent A: $H_2O$/1% IPA/10 mM ammonium acetate, and solvent B: ACN/1% IPA/10 mM ammonium acetate; flow rate: 2 mL/min). The enantiomeric excess was determined from the peak areas of the two diastereomeric derivatives formed. The ee % of the product was determined to be >93%.

Preparation B

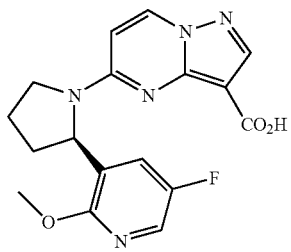 [SMILES: COc1ncc(F)cc1[C@H]1CCCN1c1ccn2ncc(C(=O)O)c2n1]

(R)-5-(2-(5-fluoro-2-methoxypyridin-3-yl)pyrrolidin-1-yl)pyrazolo[1,5-a]pyrimidine-3-carboxylic acid Step A: Preparation of ethyl 5-hydroxypyrazolo[1,5-a]pyrimidine-3-carboxylate To a mixture of ethyl 3-amino-1H-pyrazole-4-carboxylate (25.0 g, 161 mmol) and (E)-ethyl 3-ethoxyacrylate (35.8 ml, 242 mmol) in DMF (537 mL) was added cesium carbonate (78.7 g, 242 mmol), and the reaction was heated at 110° C. for 15 hours. After cooling to ambient temperature the reaction was acidified with acetic acid to pH 4. The resulting precipitate was filtered, washed with water and EtOAc, to provide the product as a white solid. To recover additional product, the filtrate was concentrated, diluted with EtOAc (500 mL) and washed with H₂O (5×200 mL). The resulting precipitate in the EtOAc layer was filtered and washed with water and EtOAc to obtain a second batch product. The two batches of product were combined and dried under reduced pressure to afford ethyl 5-hydroxypyrazolo[1,5-a]pyrimidine-3-carboxylate as a white solid (33.3 g, 100% yield). MS (apci) m/z=206.2 (M−H).

Step B: Preparation of ethyl 5-chloropyrazolo[1,5-a]pyrimidine-3-carboxylate

Ethyl 5-hydroxypyrazolo[1,5-a]pyrimidine-3-carboxylate (22.7 g, 110 mmol) was suspended in phosphoryl trichloride (100 mL) and heated to reflux. After heating for 2 hours, the reaction mixture was cooled and concentrated to remove excess POCl₃. The residue was diluted in DCM (100 mL) and slowly added to a flask containing ice water. The mixture was separated and the aqueous layer was extracted with DCM (2×200 mL). The combined organic layers were dried (MgSO₄), filtered and concentrated to afford ethyl 5-chloropyrazolo[1,5-a]pyrimidine-3-carboxylate as a pale-yellow solid (24.2 g, 97.6% yield). MS (apci) m/z=225.9 (M+H).

Step C: Preparation of (R)-ethyl 5-(2-(5-fluoro-2-methoxypyridin-3-yl)pyrrolidin-1-yl)pyrazolo[1,5-a]pyrimidine-3-carboxylate A mixture of ethyl 5-chloropyrazolo[1,5-a]pyrimidine-3-carboxylate (0.75 g, 3.32 mmol), (R)-5-fluoro-2-methoxy-3-(pyrrolidin-2-yl)pyridine (Preparation A, 0.984 g, 3.66 mmol), DIEA (2.32 mL, 13.3 mmol) and n-butanol (1.11 mL) was sealed in a pressure tube and heated at 90° C. for 48 hours. The reaction mixture was diluted with EtOAc and washed with water, brine and sat NaHCO₃. The organic layer was dried (MgSO₄), filtered and concentrated to afford a dark orange oil. The crude material was purified by silica column chromatography eluting with 50-80% EtOAc/hexanes to afford (R)-ethyl 5-(2-(5-fluoro-2-methoxypyridin-3-yl)pyrrolidin-1-yl)pyrazolo[1,5-a]pyrimidine-3-carboxylate (0.72 g, 56.2% yield) as a yellow foamy solid. MS (apci) m/z=386.0 (M+H).

Step D: Preparation of (R)-5-(2-(5-fluoro-2-methoxypyridin-3-yl)pyrrolidin-1-yl)pyrazolo[1,5-a]pyrimidine-3-carboxylic acid To a suspension of (R)-ethyl 5-(2-(5-fluoro-2-methoxypyridin-3-yl)pyrrolidin-1-yl)pyrazolo[1,5-a]pyrimidine-3-carboxylate (0.72 g, 1.868 mmol) in MeOH (9.34 mL) was added LiOH (1N, 3.74 mL, 3.74 mmol), and the reaction mixture was heated at 70° C. for 15 hours. After cooling, the reaction mixture was concentrated and the resulting residue diluted in water. After acidifying with citric acid, the aqueous layer was extracted with DCM. The combined organics were dried (MgSO₄), filtered and concentrated to afforded (R)-5-(2-(5-fluoro-2-methoxypyridin-3-yl)pyrrolidin-1-yl)pyrazolo[1,5-a]pyrimidine-3-carboxylic acid (0.67 g, 100% yield) as a yellow solid. MS (apci) m/z=357.9 (M+H).

Preparation C

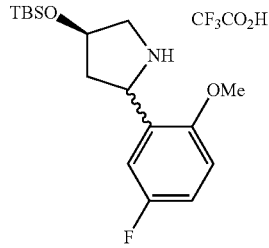 [SMILES: COc1ccc(F)cc1C1C[C@@H](O[Si](C)(C)C(C)(C)C)CN1 ; "CF3CO2H"]

(R)-4-((tert-butyldimethylsilyl)oxy)-2-(5-fluoro-2-methoxyphenyl)pyrrolidine 2,2,2-trifluoroacetate Steps A-D followed the procedure reported by H. Imamura, et al. in Tetrahedron, 2000, 56, 7705.

Step A: Preparation of (R)-4-(tert-butyldimethylsilyloxy)pyrrolidin-2-one

To a suspension of (R)-4-hydroxypyrrolidin-2-one (purchased from Asta Tech or Aldrich) (5.030 g, 48.26 mmol) in DMF (24 mL) at 0° C. was added TBDMS-Cl (7.637 g, 50.67 mmol) followed by imidazole (4.978 g, 72.39 mmol). The resulting mixture was warmed to ambient temperature and stirred for 1 hour, then poured into 100 mL of water with stirring. The resulting suspension was filtered and the solids were washed with water and dried under reduced pressure to afford (R)-4-(tert-butyldimethylsilyloxy)pyrrolidin-2-one (10.14 g, 97.56% yield) that was used directly without further purification.

Step B: Preparation of (R)-tert-butyl 4-(tert-butyldimethylsilyloxy)-2-oxopyrrolidine-1-carboxylate To a solution of (R)-4-(tert-butyldimethylsilyloxy)pyrrolidin-2-one (10.14 g, 47.08 mmol) in MeCN (16 mL) at 0° C. was added sequentially DMAP (3.221 g, 26.37 mmol), TEA (3.957 mL, 28.25 mmol), and Boc$_2$O (11.49 g, 52.65 mmol). The resulting mixture was warmed to ambient temperature and stirred for 48 hours. The reaction mixture was poured into water and extracted with EtOAc (100 mL). The organic layer was successively washed with 1N aqueous HCl (2×50 mL), 1N aqueous NaOH (50 mL), and brine. The organic layer was dried over MgSO$_4$, filtered, and concentrated in vacuo to afford (R)-tert-butyl 4-(tert-butyldimethylsilyloxy)-2-oxopyrrolidine-1-carboxylate (13.62 g, 91.69% yield). $^1$H NMR (CDCl$_3$) δ 4.39 (m, 1H), 3.87 (m, 1H), 3.62 (m, 1H), 2.71 (m, 1H), 2.46 (m, 1H), 1.53 (s, 9H), 0.88 (s, 9H), 0.08 (d, 6H).

Step C: Preparation of (R)-tert-butyl 2-(tert-butyldimethylsilyloxy)-4-(5-fluoro-2-methoxyphenyl)-4-hydroxybutylcarbamate To a solution of (R)-tert-butyl 4-(tert-butyldimethylsilyloxy)-2-oxopyrrolidine-1-carboxylate (6.00 g, 19.0 mmol) in THF (36 mL) at 0° C. was added a 0.5M solution of (5-fluoro-2-methoxyphenyl)magnesium bromide in THF (50.0 mL, 25.0 mmol). The resulting mixture was stirred at 0° C. for 30 minutes, then treated with MeOH (60 mL) and NaBH$_4$ (0.966 g, 25.2 mmol). After stirring at 0° C. for an additional 30 minutes, the reaction mixture was poured into saturated aqueous NH$_4$Cl (40 mL) and extracted with EtOAc (2×50 mL). The combined organic layers were washed with brine, dried over MgSO$_4$, filtered, and concentrated under reduced pressure to give the crude material which was purified by silica column chromatography, eluting with 0-2% MeOH/DCM to afford (R)-tert-butyl 2-(tert-butyldimethylsilyloxy)-4-(5-fluoro-2-methoxyphenyl)-4-hydroxybutylcarbamate (which was assumed to be a mixture of the syn and anti isomers), (4.81 g, 57.0% yield). $^1$H NMR (CDCl$_3$) δ 7.20 (m, 1H), 6.90 (m, 1H), 6.77 (m, 1H), 5.12 (m, 1H), 4.10 (m, 1H), 3.82 (m, 3H), 3.29 (m, 2H), 1.71-1.93 (m, 2H), 1.45 (s, 9H), 0.93 (d, 9H), 0.11-0.14 (m, 6H).

Step D: Preparation of (R)-tert-butyl 4-(tert-butyldimethylsilyloxy)-2-(5-fluoro-2-methoxyphenyl)pyrrolidine-1-carboxylate To a solution of (R)-tert-butyl 2-(tert-butyldimethylsilyloxy)-4-(5-fluoro-2-methoxyphenyl)-4-hydroxybutylcarbamate (4.810 g, 10.84 mmol) in CH$_2$Cl$_2$ (108 mL) at −60° C. was added TEA (4.534 mL, 32.53 mmol) followed by methanesulfonyl chloride (0.9231 mL, 11.93 mmol). The resulting mixture was slowly warmed to −5° C. and poured into a mixture of ice and saturated aqueous NaHCO$_3$ (50 mL). The organic layer was separated and the aqueous layer was extracted with CH$_2$Cl$_2$ (2×50 mL). The combined organic layers were dried over MgSO$_4$, filtered, and concentrated under reduced pressure to give the crude material that was purified by silica column chromatography, eluting with 2-10% MeOH/DCM to afford (R)-tert-butyl 4-(tert-butyldimethylsilyloxy)-2-(5-fluoro-2-methoxyphenyl)pyrrolidine-1-carboxylate (assumed to be a mixture of cis and trans isomers; 2.648 g, 57.38% yield). LC/MS (ES+APCI) m/z=326.1 (M+H−Boc).

Step E: Preparation of (R)-4-(tert-butyldimethylsilyloxy)-2-(5-fluoro-2-methoxyphenyl)pyrrolidine 2,2,2-trifluoroacetate To a solution of (R)-tert-butyl 4-(tert-butyldimethylsilyloxy)-2-(5-fluoro-2-methoxyphenyl)pyrrolidine-1-carboxylate (2.648 g, 6.222 mmol) in CH$_2$Cl$_2$ (26 mL) at 0° C. was added TFA (9.3 mL). The resulting mixture was warmed to ambient temperature and stirred for 2 hours. The reaction mixture was concentrated under reduced pressure to give the crude material that was azeotroped with toluene-CH$_2$Cl$_2$ (2×) and dried under reduced pressure to provide (R)-4-(tert-butyldimethylsilyloxy)-2-(5-fluoro-2-methoxyphenyl)pyrrolidine 2,2,2-trifluoroacetate (assumed to be a mixture of cis and trans isomers; 2.92 g, 106.8% yield), which was used directly without further purification. LC/MS (ES+APCI) m/z=326.3 (M+H).

Preparation D

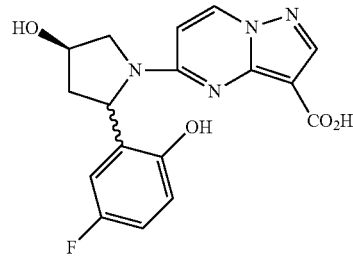 [SMILES: O=C(O)c1cnn2ccc(N3C[C@H](O)CC3c3cc(F)ccc3O)nc12]

(R)-5-(2-(5-fluoro-2-hydroxyphenyl)-4-hydroxypyrrolidin-1-yl)pyrazolo[1,5-a]pyrimidine-3-carboxylic acid

Step A: Preparation of (R)-ethyl 5-(4-(tert-butyldimethylsilyloxy)-2-(5-fluoro-2-methoxyphenyl)pyrrolidin-1-yl)pyrazolo[1,5-a]pyrimidine-3-carboxylate To a suspension of ethyl 5-hydroxypyrazolo[1,5-a]pyrimidine-3-carboxylate (0.100 g, 0.483 mmol) and BOP reagent (0.320 g, 0.724 mmol) in DMF (1 mL) at 0° C. was added a solution of (R)-4-(tert-butyldimethylsilyloxy)-2-(5-fluoro-2-methoxyphenyl)pyrrolidine 2,2,2-trifluoroacetate (Preparation C; 0.167 g, 0.483 mmol) in CH$_2$Cl$_2$ (1 mL) and N,N-diisopropylethylamine (0.420 mL, 2.41 mmol) sequentially. The resulting mixture was warmed to ambient temperature and stirred for 18 hours. The reaction mixture was diluted with EtOAc (10 mL), and washed with saturated aqueous NaHCO$_3$ and brine. The brine phase was back-extracted with EtOAc (3×). The combined organic layers were dried over MgSO$_4$, filtered, and concentrated under reduced pressure to give the crude material that was purified by silica column chromatography, eluting with 0-50% EtOAc/Hexanes to afford (R)-ethyl 5-(4-(tert-butyldimethylsilyloxy)-2-(5-fluoro-2-methoxyphenyl)pyrrolidin-1-yl)pyrazolo[1,5-a]pyrimidine-3-carboxylate (as a mixture of cis and trans isomers) (0.0487 g, 19.6% yield). LC/MS (ES+APCI) m/z=515.2 (M+H).

Step B: Preparation of (R)-ethyl 5-(2-(5-fluoro-2-methoxyphenyl)-4-hydroxypyrrolidin-1-yl)pyrazolo[1,5-a]pyrimidine-3-carboxylate To a solution of (R)-ethyl 5-(4-(tert-butyldimethylsilyloxy)-2-(5-fluoro-2-methoxyphenyl)pyrrolidin-1-yl)pyrazolo[1,5-a]pyrimidine-3-carboxylate (as a mixture of the cis and trans isomers) (0.0487 g, 0.0946 mmol) in THF (1 mL) at 0° C. was added 1M TBAF in THF (0.104 mL, 0.104 mmol). The reaction mixture was warmed to ambient temperature and stirred for 2.5 hours. The reaction mixture was diluted with EtOAc (10 mL), washed with brine, dried over MgSO$_4$, filtered, and concentrated under reduced pressure to afford the crude (R)-ethyl 5-(2-(5-fluoro-2-methoxyphenyl)-4-hydroxypyrrolidin-1-yl)pyrazolo[1,5-a]pyrimidine-3-carboxylate (as a mixture of cis and trans isomers; 37.9 mg, 100% yield). LC/MS (ES+APCI) m/z=401.1 (M+H).

Step C: Preparation of (R)-ethyl 5-(2-(5-fluoro-2-hydroxyphenyl)-4-hydroxypyrrolidin-1-yl)pyrazolo[1,5-a]pyrimidine-3-carboxylate To a solution of (R)-ethyl 5-(2-(5-fluoro-2-methoxyphenyl)-4-hydroxypyrrolidin-1-yl)pyrazolo[1,5-a]pyrimidine-3-carboxylate (as a mixture of cis and trans isomers; 0.0379 g, 0.0947 mmol) in CH$_2$Cl$_2$ (1 mL) at 0° C. was added 1M BBr$_3$ in CH$_2$Cl$_2$ (0.473 ml, 0.473 mmol). The resulting mixture was warmed to ambient temperature for 25 hours, then diluted with CH$_2$Cl$_2$ (10 mL) and poured into a mixture of ice and saturated aqueous NaHCO$_3$ (15 mL). The organic layer was separated and the aqueous layer acidified with 1N aqueous HCl until pH=5-6. The aqueous layer was extracted with CH$_2$Cl$_2$ (3×) and the combined organic layers were dried over MgSO$_4$, filtered, and concentrated under reduced pressure to give a mixture of (R)-5-(2-(5-fluoro-2-hydroxyphenyl)-4-hydroxypyrrolidin-1-yl)pyrazolo[1,5-a]pyrimidine-3-carboxylic acid (as a mixture of cis and trans isomers) and (R)-ethyl 5-(2-(5-fluoro-2-hydroxyphenyl)-4-hydroxypyrrolidin-1-yl)pyrazolo[1,5-a]pyrimidine-3-carboxylate (as a mixture of cis and trans isomers). The mixture was dissolved in MeOH-THF (0.25 mL/0.75 mL) and treated with 1N aqueous LiOH (0.474 mL, 0.474 mmol). The resulting mixture was heated at 50° C. for 1 hour, then cooled to ambient temperature and acidified to pH 3 to 4 with 1N aqueous HCl. The mixture was extracted with EtOAc (3×15 mL) and the combined organic layers were dried over MgSO$_4$, filtered, and concentrated under reduced pressure to give crude (R)-5-(2-(5-fluoro-2-hydroxyphenyl)-4-hydroxypyrrolidin-1-yl)pyrazolo[1,5-a]pyrimidine-3-carboxylic acid (as a mixture of cis and trans isomers; 33.9 mg, 100% yield). LC/MS (ES+APCI) m/z=357.1 (M−H).

Example 1

(6R)-9-fluoro-2,11,15,19,20,23-hexaazapentacyclo[15.5.2.1$^{7,11}$.0$^{2,6}$.0$^{20,24}$]pentacosa-1(23),7,9,17(24),18,21-hexaene-16,25-dione Step A: Preparation of (R)-ethyl 5-(2-(5-fluoro-2-oxo-1,2-dihydropyridin-3-1yl)pyrrolidin-1-yl)pyrazolo[1,5-a]pyrimidine-3-carboxylate To a mixture of (R)-ethyl 5-(2-(5-fluoro-2-methoxypyridin-3-yl)pyrrolidin-1-yl)pyrazolo[1,5-a]pyrimidine-3-carboxylate (Preparation B, Step C; 0.92 g, 2.39 mmol) and Acetic acid (5.73 g, 95.5 mmol) was added HBr (4.4 mL, 23.9 mmol, 33% in acetic acid). The reaction mixture was heated at 90° C. for 2 hours. After cooling, the reaction mixture was treated with EtOAc, washed with water, saturated NaHCO$_3$ and brine, then dried (MgSO$_4$), filtered, and concentrated. The crude material was purified by silica column chromatography, eluting with 3% MeOH/DCM to yield the desired product (0.605 g, 68% yield). MS (apci) m/z=372.0 (M+H).

Step B: Preparation of (R)-ethyl 5-(2-(1-(3-(1,3-dioxoisoindolin-2-yl)propyl)-5-fluoro-2-oxo-1,2-dihydropyridin-3-yl)pyrrolidin-1-yl)pyrazolo[1,5-a]pyrimidine-3-carboxylate To a DMF (5 mL) suspension of (R)-ethyl 5-(2-(5-fluoro-2-oxo-1,2-dihydropyridin-3-yl)pyrrolidin-1-yl)pyrazolo[1,5-a]pyrimidine-3-carboxylate (0.20 g, 0.54 mmol) was added LiH (6.8 mg, 0.81 mmol) at 0° C., followed first by 20-minute stirring, then addition of a DMF (1 mL) solution of 2-(3-bromopropyl)isoindoline-1,3-dione (0.29 g, 1.1 mmol). The reaction was warmed to ambient temperature and stirred for 17 hours. After cooling to 0° C. the reaction was quenched with ice-water (30 mL) and the aqueous was extracted with EtOAc (3×50 mL). The combined organic layers were backwashed with water and brine, dried (MgSO$_4$), filtered, and concentrated. The crude material was purified by silica column chromatography, eluting with 2% MeOH/DCM to yield the desired product (0.2 g, 66% yield). MS (apci) m/z=559.0 (M+H).

Step C: Preparation of (R)-ethyl 5-(2-(1-(3-aminopropyl)-5-fluoro-2-oxo-1,2-dihydropyridin-3-yl)pyrrolidin-1-yl)pyrazolo[1,5-a]pyrimidine-3-carboxylate To a solution of (R)-ethyl 5-(2-(1-(3-(1,3-dioxoisoindolin-2-yl)propyl)-5-fluoro-2-oxo-1,2-dihydropyridin-3-yl)pyrrolidin-1-yl)pyrazolo[1,5-a]pyrimidine-3-carboxylate (0.20 g, 0.36 mmol) in 1:1 MeOH/THF (12 mL) was added hydrazine-H$_2$O (0.18 g, 3.6 mmol). The reaction mixture was heated at 50° C. for 24 hours. After cooling, the reaction mixture was poured into water and extracted with DCM (3×20 mL). The combined organics were dried (MgSO$_4$), filtered, and concentrated to afford the desired product (0.11 g, 72% yield). MS (apci) m/z=429.0 (M+H).

Step D: Preparation of (R)-5-(2-(1-(3-aminopropyl-5-fluoro-2-oxo-1,2-dihydropyridin-3-yl)pyrrolidin-1-yl)pyrazolo[1,5-a]pyrimidine-3-carboxylic acid To a solution of (R)-ethyl 5-(2-(1-(3-aminopropyl)-5-fluoro-2-oxo-1,2-dihydropyridin-3-yl)pyrrolidin-1-yl)pyrazolo[1,5-a]pyrimidine-3-carboxylate (0.11 g, 0.26 mmol) in 3:1 THF/MeOH (8 mL) was added LiOH (1N, 1.5 mL, 1.5 mmol), and the reaction mixture was heated at 70° C. for 20

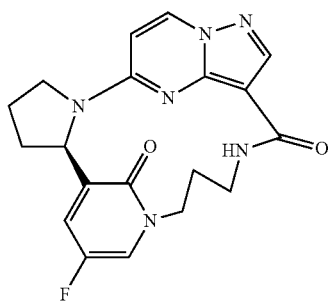 [SMILES: O=C1NCCCn2cc(F)cc(c2=O)[C@H]2CCCN2c2ccn3ncc1c3n2]

hours. After cooling, the reaction mixture was treated with MeOH, acidified with 1N HCl (1.5 mL), and concentrated to afford the desired product (0.1 g, 100% yield). MS (apci) m/z=401.1 (M+H).

Step E: Preparation of (6R)-9-fluoro-2,11,15,19,20,23-hexaazapentacyclo[15.5.2.1$^{7,11}$.0$^{2,6}$.0$^{20,24}$]pentacosa-1(23),7,9,17(24),18,21-hexaene-16,25-dione To a solution of (R)-5-(2-(1-(3-aminopropyl)-5-fluoro-2-oxo-1,2-dihydropyridin-3-yl)pyrrolidin-1-yl)pyrazolo[1,5-a]pyrimidine-3-carboxylic acid (95 mg, 0.24 mmol) in 1:2 DMF/DCM (9 mL) was added EDCI (0.14 g, 0.71 mmol) followed by HOBT (96 mg, 0.71 mmol) at ambient temperature. After stirring for 10 minutes, TEA (0.099 mL, 0.71 mmol) was added to the reaction mixture and stirred for 6 hours. The reaction mixture was treated with EtOAc, washed with saturated NH$_4$Cl, saturated NaHCO$_3$, and brine, then dried (MgSO$_4$), filtered, concentrated. The crude material was purified by silica column chromatography, eluting with 4% MeOH/DCM to yield the title product (35 mg, 39% yield). MS (apci) m/z=383.2 (M+H).

Example 2

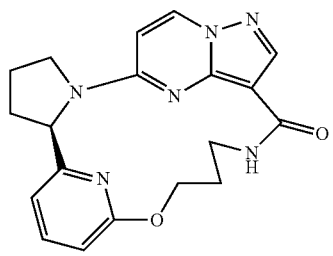 [SMILES: O=C1NCCCOc2cccc(n2)[C@H]2CCCN2c2ccn3ncc1c3n2]

(6R)-12-oxa-2,16,20,21,24,26-hexaazapentacyclo [16.5.2.1$^{7,11}$.0$^{2,6}$.0$^{21,25}$]hexacosa-1(24),7(26),8,10,18(25),19,22-heptaen-17-one Step A: Preparation of (R)-2-methoxy-6-(pyrrolidin-2-yl)pyridine Prepared according to the method described in Preparation A, substituting 3-bromo-5-fluoro-2-methoxypyridine with 2-bromo-6-methoxypyridine in Step A. MS (apci) m/z=179.1 (M+H).

Step B: Preparation of (R)-ethyl 5-(2-(6-methoxypyridin-2-yl)pyrrolidin-1-yl)pyrazolo[1,5-a]pyrimidine-3-carboxylate Prepared by to the same method as described in Preparation B, Step C, substituting (R)-5-fluoro-2-methoxy-3-(pyrrolidin-2-yl)pyridine with (R)-2-methoxy-6-(pyrrolidin-2-yl)pyridine. MS (apci) m/z=368.0 (M+H).

Step C: Preparation of (R)-ethyl 5-(2-(6-oxo-1,6-dihydropyridin-2-yl)pyrrolidin-1-yl)pyrazolo[1,5-a]pyrimidine-3-carboxylate To a mixture of (R)-ethyl 5-(2-(6-methoxypyridin-2-yl)pyrrolidin-1-yl)pyrazolo[1,5-a]pyrimidine-3-carboxylate (0.46 g, 1.25 mmol) and acetic acid (3.0 g, 50 mmol) was added HBr (3.1 g, 12.5 mmol, 33% in acetic acid). The reaction mixture was heated at 90° C. for 2 hours. After cooling, the reaction was diluted with EtOAc, washed with water, saturated NaHCO$_3$, and brine, then dried (MgSO$_4$), filtered, and concentrated. The crude material was purified by silica column chromatography, eluting with 4% MeOH/DCM to yield the desired product (0.3 g, 67% yield). MS (apci) m/z=354.1 (M+H).

Step D: Preparation of (R)-ethyl 5-(2-(6-(3-(1,3-dioxoisoindolin-2-yl)propoxy)pyridin-2-yl)pyrrolidin-1-yl)pyrazolo[1,5-a]pyrimidine-3-carboxylate To a suspension of (R)-ethyl 5-(2-(6-oxo-1,6-dihydropyridin-2-yl)pyrrolidin-1-yl)pyrazolo[1,5-a]pyrimidine-3-carboxylate (0.091 g, 0.26 mmol) in DMF (2 mL) was added LiH (3.2 mg, 0.39 mmol) at 0° C. After stirring for 20 minutes, a solution of 2-(3-bromopropyl)isoindoline-1,3-dione (0.14 g, 0.52 mmol) in DMF (1 mL) was added, and the reaction was warmed up to ambient temperature and stirred for 17 hours. After cooling to 0° C., the reaction was quenched with ice-water (30 mL) and extracted with EtOAc (3×50 mL). The combined organic layers were washed with water and brine, dried (MgSO$_4$), filtered, and concentrated. The crude material was purified by silica column chromatography, eluting with 1.5% MeOH/DCM to yield the desired product (0.117 g, 84% yield). MS (apci) m/z=541.1 (M+H).

Step E: Preparation of (R)-ethyl 5-(2-(6-(3-aminopropoxy)pyridin-2-yl)pyrrolidin-1-yl)pyrazolo[1,5-a]pyrimidine-3-carboxylate To a solution of (R)-ethyl 5-(2-(6-(3-(1,3-dioxoisoindolin-2-yl)propoxy)pyridin-2-yl)pyrrolidin-1-yl)pyrazolo[1,5-a]pyrimidine-3-carboxylate (0.11 g, 0.20 mmol) in 1:1 MeOH/THF (12 mL) was added hydrazine-H$_2$O (0.10 g, 2.0 mmol). The reaction mixture was heated at 50° C. for 24 hours. After cooling, the reaction mixture was poured into water then extracted with DCM (3×20 mL). The combined organics were dried (MgSO$_4$), filtered, and concentrated to afford the desired product (70 mg, 84% yield). MS (apci) m/z=441.1 (M+H).

Step F: Preparation of (R)-5-(2-(6-(3-aminopropoxy)pyridin-2-yl)pyrrolidin-1-yl)pyrazolo[1,5-a]pyrimidine-3-carboxylic acid To a solution of (R)-ethyl 5-(2-(6-(3-aminopropoxy)pyridin-2-yl)pyrrolidin-1-yl)pyrazolo[1,5-a]pyrimidine-3-carboxylate (70 mg, 0.17 mmol) in 3:1 THF/MeOH (8 mL) was added LiOH (1N, 1.5 mL, 1.5 mmol) and the reaction mixture was heated at 70° C. for 20 hours. After cooling, the reaction mixture was diluted with MeOH, acidified with 1N HCl (1.5 mL), and concentrated to afford the desired product (65 mg, 100% yield). MS (apci) m/z=383.1 (M+H).

Step G: Preparation of (6R)-12-oxa-2,16,20,21,24,26-hexaazapentacyclo-[16.5.2.1$^{7,11}$.0$^{2,6}$.0$^{21,25}$]hexacosa-1(24),7(26),8,10,18(25),19,22-heptaen-17-one To a solution of (R)-5-(2-(6-(3-aminopropoxy)pyridin-2-yl)pyrrolidin-1-yl)pyrazolo[1,5-a]pyrimidine-3-carboxylic acid (70 mg, 0.18 mmol) in 1:2 DMF/DCM (9 mL) was added EDCI (110 mg, 0.55 mmol) followed by HOBT (74 mg, 0.55 mmol) at ambient temperature. After stirring for 10 minutes. TEA (0.077 mL, 0.55 mmol) was added to the reaction mixture and stirred for 6 hours. The reaction mixture was diluted with EtOAc, washed with saturated NH₄Cl, saturated NaHCO₃, and brine, then dried (MgSO₄), filtered, and concentrated. The crude material was purified by silica column chromatography, eluting with 2% MeOH/DCM to yield the title product (30 mg, 45% yield). MS (apci) m/z=365.2 (M+H).

Example 3

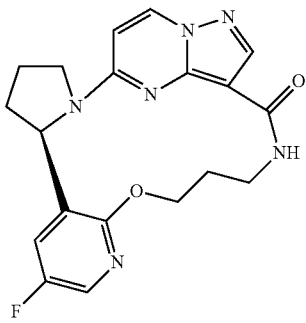 [SMILES: O=C1NCCCOc2ncc(F)cc2[C@H]2CCCN2c2ccn3ncc1c3n2]

(6R)-9-fluoro-13-oxa-2,11,17,21,22,25-hexaazapentacyclo[17.5.2.0$^{2,6}$.0$^{7,12}$.0$^{22,26}$]hexacosa-1(25),7,9,11,19(26),20,23-heptaen-18-one Step A: Preparation of (R)-5-(2-(5-fluoro-2-methoxypyridin-3-yl)pyrrolidin-1-yl)-N-(3-hydroxypropyl)pyrazolo[1,5-a]pyrimidine-3-carboxamide To a DMF (2 mL) suspension of (R)-5-(2-(5-fluoro-2-methoxypyridin-3-yl)pyrrolidin-1-yl)pyrazolo[1,5-a]pyrimidine-3-carboxylic acid (Preparation B, 250 mg, 0.700 mmol) and HATU (319 mg, 0.840 mmol) cooled to 0° C. was added 3-aminopropan-1-ol (0.0642 mL, 0.840 mmol) drop-wise, resulting in a clear yellowish solution. After dropwise addition of DIEA (0.366 mL, 2.10 mmol), ice bath was removed and reaction was stirred at ambient temperature for 1 hour. The reaction was directly purified on reverse phase column chromatography (Biotage SP4 system, C-18 25+M column, 0 to 54% Acetonitrile/water), to provide the product as white solid (200 mg, 69% yield). MS (apci) m/z=415.1 (M+H).

Step B: Preparation of (R)—N-(3-chloropropyl)-5-(2-(5-fluoro-2-hydroxypyridin-3-yl)pyrrolidin-1-yl)pyrazolo[1,5-a]pyrimidine-3-carboxamide A mixture of (R)-5-(2-(5-fluoro-2-methoxypyridin-3-yl)pyrrolidin-1-yl)-N-(3-hydroxypropyl)pyrazolo[1,5-a]pyrimidine-3-carboxamide (20 mg, 0.0483 mmol) in HCl (4N dioxane, 1.2 mL, 4.83 mmol) was heated at 85° C. overnight. The reaction mixture was concentrated, triturated with ether, and filtered, to provide the crude product as a beige solid, which was directly used in the next step without further purification (22 mg, 106% yield). MS (apci) m/z=419.1 (M+H).

Step C: Preparation of (6R)-9-fluoro-13-oxa-2,11,17,21,22,25-hexaazapentacyclo[17.5.2.0$^{2,6}$.0$^{7,12}$.0$^{22,26}$]hexacosa-1(25),7,9,11,19(26),20,23-heptaen-18-one A DMF (1 mL) suspension of (R)—N-(3-chloropropyl)-5-(2-(5-fluoro-2-hydroxypyridin-3-yl)pyrrolidin-1-yl)pyrazolo[1,5-a]pyrimidine-3-carboxamide (5 mg, 0.012 mmol) and Cs₂CO₃ (4 mg, 0.06 mmol) was heated at 85° C. overnight. The reaction mixture was filtered through a GF/F paper and directly purified on reverse phase column chromatography (Biotage SP4 system C-18 12+M column, 5 to 60% acetonitrile/water), to provide the title product as white solid (2 mg, 44% yield). MS (apci) m/z=383.3 (M+H).

Example 4

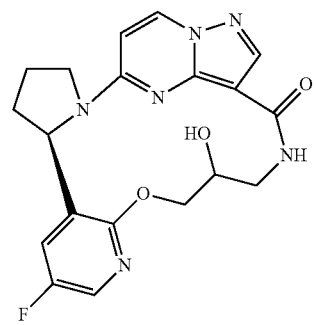 [SMILES: O=C1NCC(O)COc2ncc(F)cc2[C@H]2CCCN2c2ccn3ncc1c3n2]

(6R)-9-fluoro-15-hydroxy-13-oxa-2,11,17,21,22,25-hexaazapentacyclo[17.5.2.0$^{2,6}$.0$^{7,12}$.0$^{22,26}$]hexacosa-1(25),7,9,11,19(26),20,23-heptaen-18-one Step A: Preparation of N-(2,3-dihydroxypropyl)-5-((R)-2-(5-fluoro-2-methoxypyridin-3-yl)pyrrolidin-1-yl)pyrazolo[1,5-a]pyrimidine-3-carboxamide A mixture of (R)-5-(2-(5-fluoro-2-methoxypyridin-3-yl)pyrrolidin-1-yl)pyrazolo[1,5-a]pyrimidine-3-carboxylic acid (Preparation B, 250 mg, 0.700 mmol) and HATU (319 mg, 0.840 mmol) in 1:1 DMF/DMSO (2 mL) was cooled to 0° C., followed first by drop-wise addition of 3-aminopropane-1,2-diol (76.5 mg, 0.840 mmol) and then addition of DIEA (366 μL, 2.10 mmol). The reaction was warmed up to ambient temperature, stirred for 20 minutes, and then directly purified on reverse phase column chromatography (Biotage SP4 system C-18 25+M cartridge, 5 to 50% acetonitrile/water), to provide the product as a white solid (295 mg, 98% yield). MS (apci) m/z=431.1 (M+H).

Step B: Preparation of N-(3-chloro-2-hydroxypropyl)-5-((R)-2-(5-fluoro-2-oxo-1,2-dihydropyridin-3-yl)pyrrolidin-1-yl)pyrazolo[1,5-a]pyrimidine-3-carboxamide A mixture of N-(2,3-dihydroxypropyl)-5-((R)-2-(5-fluoro-2-methoxypyridin-3-yl)pyrrolidin-1-yl)pyrazolo[1,5-a]pyrimidine-3-carboxamide (100 mg, 0.232 mmol) and HCl (4N, dioxane, 5.8 mL) was sealed in a pressure tube and heated at 85° C. overnight. After the clear solution was decanted, the crude product was obtained as a brownish oily residue, which was vacuum-dried and used directly in the next step without further purification. MS (apci) m/z=435.0 (M+H).

Step C: Preparation of (6R)-9-fluoro-15-hydroxy-13-oxa-2,11,17,21,22,25-hexaazapentacyclo[17.5.2.0$^{2,6}$.0$^{7,12}$.0$^{22,26}$]hexacosa-1 (25),7,9,11,19(26),20,23-heptaen-18-one A suspension of N-(3-chloro-2-hydroxypropyl)-5-((R)-2-(5-fluoro-2-oxo-1,2-dihydropyridin-3-yl)pyrrolidin-1-yl)pyrazolo[1,5-a]pyrimidine-3-carboxamide (100 mg, 0.23 mmol) and Cs$_2$CO$_3$ (375 mg, 1.15 mmol) in DMF (3 mL) was heated at 85° C. for 2 hours. The reaction mixture was filtered through a GF/F paper and directly purified on reverse phase column chromatography (Biotage SP4 system C-18 25+M column, 5 to 50% acetonitrile/water), to provide the title product as a white solid. MS (apci) m/z=399.2 (M+H).

Example 5

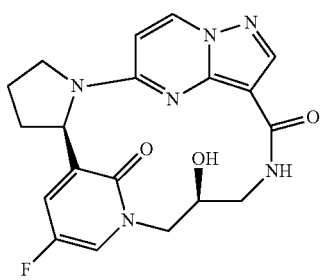 [SMILES: O=C1NC[C@H](O)Cn2cc(F)cc(c2=O)[C@H]2CCCN2c2ccn3ncc1c3n2]

(6R,13S)-9-fluoro-13-hydroxy-2,11,15,19,20,23-hexaazapentacyclo-[15.5.2.1$^{7,11}$.0$^{2,6}$.0$^{20,24}$]pentacosa-1(23),7,9,17(24),18,21-hexaene-16,25-dione Step A: Preparation of N—((S)-3-chloro-2-hydroxypropyl)-5-((R)-2-(5-fluoro-2-oxo-1,2-dihydropyridin-3-yl)pyrrolidin-1-yl)pyrazolo[1,5-a]pyrimidine-3-carboxamide hydrochloride Prepared according to the method described in Example 3. Steps A-B, substituting 3-aminopropan-1-ol in Step A with (S)-3-aminopropane-1,2-diol. MS (apci) m/z=435.0 (M+H).

Step B: Preparation of (6R,13S)-9-fluoro-13-hydroxy-2,11,15,19,20,23-hexaazapentacyclo[15.5.2.1$^{7,11}$.0$^{2,6}$.0$^{20,24}$]pentacosa-1(23),7,9,17(24),18,21-hexaene-16,25-dione A suspension of N—((S)-3-chloro-2-hydroxypropyl)-5-((R)-2-(5-fluoro-2-oxo-1,2-dihydropyridin-3-yl)pyrrolidin-1-yl)pyrazolo[1,5-a]pyrimidine-3-carboxamide hydrochloride (40 mg, 0.085 mmol) and Cs$_2$CO$_3$ (138 mg, 0.42 mmol) in DMF (0.8 mL) was heated at 85° C. for 2 hours. The reaction mixture was filtered through GF/F paper and directly purified on reverse phase column chromatography (Biotage SP4 system C-18 12+M column, 0 to 40% acetonitrile/water), to provide the title product as a white solid (4 mg, 12% yield). MS (apci) m/z=399.2 (M+H).

Example 6

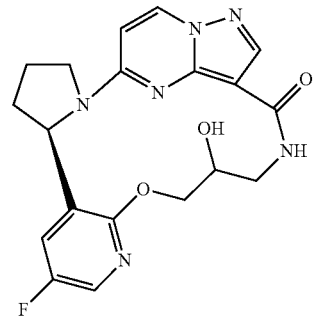 [SMILES: O=C1NCC(O)COc2ncc(F)cc2[C@H]2CCCN2c2ccn3ncc1c3n2]

(6R)-9-fluoro-15-hydroxy-13-oxa-2,11,17,21,22,25-hexaazapentacyclo-[17.5.2.0$^{2,6}$.0$^{7,12}$.0$^{22,26}$]hexacosa-(25),7,9,11,19(26),20,23-heptaen-18-one Prepared according to the method described in Example 5 and isolated as a by-produce in Step B. The enantiomeric integrity of the chiral center where the HO group resides was found to have unexpectedly eroded (R/S ratio was about 10:7) in the isolated final product (6R)-9-fluoro-15-hydroxy-13-oxa-2,11,17,21,22,25-hexaazapentacyclo-[17.5.2.0$^{2,6}$.0$^{7,12}$.0$^{22,26}$]hexacosa-1 (25),7,9,11,19(26),20,23-heptaen-18-one, which was obtained as a white solid (5 mg, 15% yield) by reverse phase column chromatography (Biotage SP4 system C-18 12+M column, 0 to 50% acetonitrile/water). MS (apci) m/z=399.2 (M+H).

Example 7

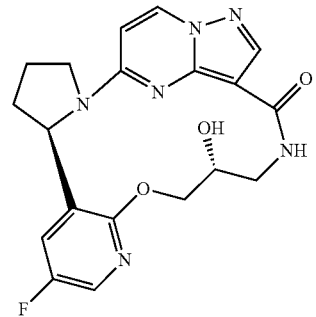 [SMILES: O=C1NC[C@@H](O)COc2ncc(F)cc2[C@H]2CCCN2c2ccn3ncc1c3n2]

(6R,15R)-9-fluoro-15-hydroxy-13-oxa-2,11,17,21,22,25-hexaazapentacyclo-[17.5.2.0$^{2,6}$.0$^{7,12}$.0$^{22,26}$]hexacosa-1 (25),7,9,11,19(26),20,23-heptaen-18-one Step A: Preparation of N—((R)-3-chloro-2-hydroxypropyl)-5-((R)-2-(5-fluoro-2-oxo-1,2-dihydropyridin-3-yl)pyrrolidin-1-yl)pyrazolo[1,5-a]pyrimidine-3-carboxamide Prepared according to the method described in Example 3, Steps A-B, substituting 3-aminopropan-1-ol in Step A with (R)-3-aminopropane-1,2-diol. MS (apci) m/z=435.0 (M+H).

Step B: Preparation of (6R,15R)-9-fluoro-15-hydroxy-13-oxa-2,11,17,21,22,25-hexaazapentacyclo[17.5.2.0$^{2,6}$.0$^{7,12}$.0$^{22,26}$]hexacosa-1(25),7,9,11,19(26),20,23-heptaen-18-one A suspension of N—((R)-3-chloro-2-hydroxypropyl)-5-((R)-2-(5-fluoro-2-oxo-1,2-dihydropyridin-3-yl)pyrrolidin-1-yl)pyrazolo[1,5-a]pyrimidine-3-carboxamide (30 mg, 0.069 mmol) and Cs$_2$CO$_3$ (112 mg, 0.34 mmol) in DMF (0.7 mL) was heated at 85° C. for 1 hour. The reaction mixture was filtered through a GF/F paper and directly purified on reverse phase column chromatography (Biotage SP4 system C-18 12+M column, 0 to 50% acetonitrile/water), to provide the title product as a white solid (10 mg, 36% yield). Unlike Example 6, no erosion of the enantiomeric integrity of the chiral center where HO group resides was observed for this final product. MS (apci) m/z=399.2 (M+H).

Example 8

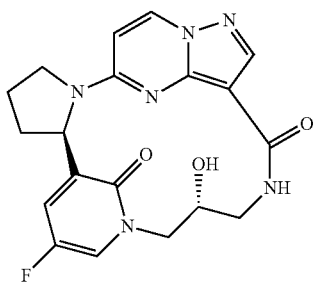 [SMILES: O=C1NC[C@@H](O)Cn2cc(F)cc(c2=O)[C@H]2CCCN2c2ccn3ncc1c3n2]

(6R,13R)-9-fluoro-13-hydroxy-2,11,15,19,20,23-hexaazapentacyclo-[15.5.2.1$^{7,11}$.0$^{2,6}$.0$^{20,24}$]pentacosa-1(23),7,9,17(24),18,21-hexaene-16,25-dione Obtained as a by-product of Example 7, Step B and isolated as a white solid (1.2 mg, 4% yield) by reverse phase column chromatography (Biotage SP4 system C-18 12+M column, 0 to 44% acetonitrile/water) of the crude material of Example 7, Step B. MS (apci) m/z=399.2 (M+H).

Example 9

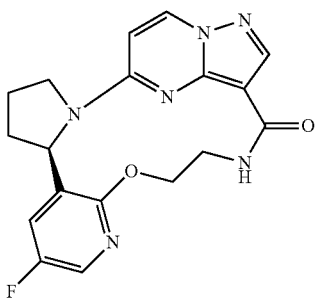 [SMILES: O=C1NCCOc2ncc(F)cc2[C@H]2CCCN2c2ccn3ncc1c3n2]

(6R)-9-fluoro-13-oxa-2,11,16,20,21,24-hexaazapentacyclo[16.5.2.0$^{2,6}$.0$^{7,12}$.0$^{21,25}$]pentacosa-1(24),7,9,11,18(25),19,22-heptaen-17-one

Step A: Preparation of (R)-5-(2-(5-fluoro-2-methoxypyridin-3-yl)pyrrolidin-1-yl)-N-(2-hydroxyethyl)pyrazolo[1,5-a]pyrimidine-3-carboxamide To a DMF (1 mL) suspension of (R)-5-(2-(5-fluoro-2-methoxypyridin-3-yl)pyrrolidin-1-yl)pyrazolo[1,5-a]pyrimidine-3-carboxylic acid (Preparation B, 100 mg, 0.28 mmol) and HATU (128 mg, 0.336 mmol) was added DIEA (0.146 mL, 0.840 mmol) at ambient temperature, followed by a solution of 2-aminoethanol (20.5 mg, 0.336 mmol) in minimal amount of DMF dropwise at 0° C. The reaction was warmed up to ambient temperature and stirred for 30 minutes, then directly purified by reverse-phase column chromatography (0 to 70% acetonitrile/water) to yield the product as white solid (95 mg, 85% yield). MS (apci pos) m/z=401.1 (M+H).

Step B: Preparation of (R)—N-(2-chloroethyl)-5-(2-(5-fluoro-2-oxo-1,2-dihydropyridin-3-yl)pyrrolidin-1-yl)pyrazolo[1,5-a]pyrimidine-3-carboxamide To (R)-5-(2-(5-fluoro-2-methoxypyridin-3-yl)pyrrolidin-1-yl)-N-(2-hydroxyethyl)pyrazolo[1,5-a]pyrimidine-3-carboxamide (77 mg, 0.192 mmol) in a pressure reaction tube was charged hydrogen chloride (4N dioxane, 4.8 mL, 19.2 mmol) and the resulting white suspension was heated at 85° C. overnight. After cooling to ambient temperature, the reaction mixture was decanted to yield the crude product as brownish oily residue, which was dried in vacuo and directly used in the next step without further purification. MS (apci) m/z=405.0 (M+H).

Step C: Preparation of (6R)-9-fluoro-13-oxa-2,11,16,20,21,24-hexaazapentacyclo[16.5.2.0$^{2,6}$.0$^{7,12}$.0$^{21,25}$]pentacosa-1(24),7,9,11,18(25),19,22-heptaen-17-one A suspension of (R)—N-(2-chloroethyl)-5-(2-(5-fluoro-2-oxo-1,2-dihydropyridin-3-yl)pyrrolidin-1-yl)pyrazolo[1,5-a]pyrimidine-3-carboxamide (78 mg, 0.19 mmol) and Cs$_2$CO$_3$ (314 mg, 0.96 mmol) in DMF (5 mL) was heated at 85° C. for 30 minutes. After filtering through a GF/F paper the reaction was diluted with water (40 mL) and NH$_4$Cl (saturated, 5 mL), then extracted with EtOAc (3×40 mL). The combined organic extracts were dried (Na$_2$SO$_4$), filtered, and concentrated. The crude material was purified by reverse phase column chromatography (Biotage SP4 system C-18 12+M column, 0 to 73% acetonitrile/water), to provide the title product as a white solid (17 mg, 24% yield). MS (apci) m/z=369.2 (M+H).

Example 10

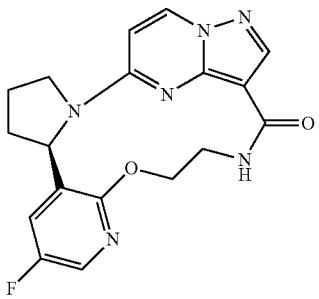 [SMILES: O=C1NCCOc2ncc(F)cc2[C@H]2CCCN2c2ccn3ncc1c3n2]

(6R)-9-fluoro-13-oxa-2,11,18,22,23,26-hexaazapentacyclo[18.5.2.0$^{2,6}$.0$^{7,12}$.0$^{23,27}$]heptacosa-1(26),7,9,11,20(27),21,24-heptaen-19-one Step A: Preparation of (R)—N-(4-chlorobutyl)-5-(2-(5-fluoro-2-oxo-1,2-dihydropyridin-3-yl)pyrrolidin-1-yl)pyrazolo[1,5-a]pyrimidine-3-carboxamide Prepared according to the method described in Example 3, Steps A-B, substituting 3-aminopropan-1-ol in Step A with 4-aminobutan-1-ol. MS (apci) m/z=433.0 (M+H).

Step B: Preparation of (6R)-9-fluoro-13-oxa-2,11,18,22,23,26-hexaazapentacyclo-[18.5.2.0$^{2,6}$.0$^{7,12}$.0$^{23,27}$]heptacosa-1(26),7,9,11,20(27),21,24-heptaen-19-one Prepared according to the method described in Example 3, substituting (R)—N-(3-chloropropyl)-5-(2-(5-fluoro-2-hydroxypyridin-3-yl)pyrrolidin-1-yl)pyrazolo[1,5-a]pyrimidine-3-carboxamide with (R)—N-(4-chlorobutyl)-5-(2-(5-fluoro-2-oxo-1,2-dihydropyridin-3-yl)pyrrolidin-1-yl)pyrazolo[1,5-a]pyrimidine-3-carboxamide in Step C. The crude product was purified on reverse phase column chromatography (Biotage SP4 system C-18 25+M column, 0 to 80% acetonitrile/water), to provide the title product as a white solid (32 mg, 44%). MS (apci pos) m/z=397.2 (M+H).

Example 11

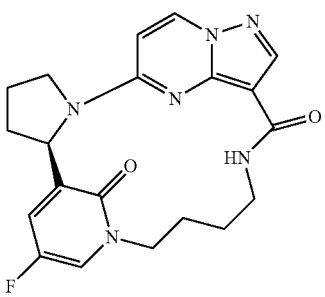 [SMILES: O=C1NCCCCn2cc(F)cc(c2=O)[C@H]2CCCN2c2ccn3ncc1c3n2]

(6R)-9-fluoro-2,11,16,20,21,24-hexaazapentacyclo[16.5.2.1$^{7,11}$.0$^{2,6}$.0$^{21,25}$]hexacosa-1(24),7,9,18(25),19,22-hexaene-17,26-dione Obtained as a by-product in Example 10, Step B and isolated a white solid (4 mg, 6%) upon purification of the crude material of Example 10, Step B by reverse phase column chromatography (Biotage SP4 system C-18 25+M column, 0 to 50% acetonitrile/water). MS (apci) m/z=397.2 (M+H).

Example 12

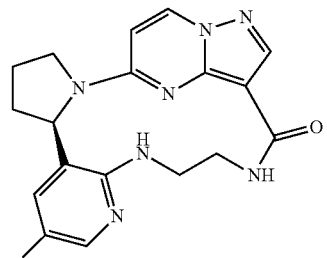

(6R)-9-fluoro-2,11,13,16,20,21,24-heptaazapentacyclo[16.5.2.0$^{2,6}$.0$^{7,12}$.0$^{21,25}$]pentacosa-1(24),7,9,11,18(25),19,22-heptaen-17-one Step A: Preparation of (R)-tert-butyl 2-(2-chloro-5-fluoropyridin-3-yl)pyrrolidine-1-carboxylate A solution of tert-butyl pyrrolidine-1-carboxylate (1 mL 5.70 mmol) and (−)-sparteine (1.31 mL, 5.70 mmol) in anhydrous MTBE (30 mL) was first cooled to −78° C. under nitrogen, followed by addition of sec-butyl lithium (4.07 mL, 1.4M, 5.70 mmol) drop-wise over 15 minutes with a syringe, maintaining the temperature below −75° C. The pale yellowish solution was stirred at −78° C. for 3 hours before being treated with zinc chloride (3.80 mL, 1.0M, 3.80 mmol) drop-wise over 15 minutes, maintaining the temperature below −73° C. The mixture was stirred at −78° C. for 30 minutes, then placed into an ambient temperature water bath and stirred for another hour. At this point a large amount of white precipitate was present. The mixture was treated with 3-bromo-2-chloro-5-fluoropyridine (1.00 g, 4.75 mmol) in MTBE (5 mL), followed by addition of palladium acetate (53 mg, 0.24 mmol) and tri-t-butylphosphine tetrafluoroborate (83 mg, 0.28 mmol). The mixture was allowed to stir at ambient temperature overnight to reach completion. The mixture was treated with NH$_4$OH (1 mL), stirred for 30 minutes and filtered through GF/F paper, washing with MTBE. The filtrate was washed with 10% citric acid (30 mL) and the aqueous layer was back-washed with MTBE (2×30 mL). The combined organic phases were washed with brine (20 mL), dried (MgSO$_4$), and concentrated to afford the crude product as dark yellowish oil. This crude material was purified on a silica 50 g Biotage SNAP cartridge eluting with 10% EtOAc in hexanes to afford the desired product as colorless oil (0.5 g, 35% yield). MS (apci) m/z=201.1 (M+H−Boc).

Step B: Preparation of (R)-2-chloro-5-fluoro-3-(pyrrolidin-2-yl)pyridine dihydrochloride To a dioxane (5 mL) solution of (R)-tert-butyl 2-(2-chloro-5-fluoropyridin-3-yl)pyrrolidine-1-carboxylate (500 mg, 1.66 mmol) was added HCl (4N dioxane, 20 mL), followed by stirring at ambient temperature overnight. The mixture was concentrated and treated with Et$_2$O, then vacuum-dried, to provide the product as a white solid (0.36 g, 80% yield). MS (apci) m/z=201.1 (M+H). The enantiomeric excess (ee %) of the product was determined to be >92% according to the method described in Preparation A.

Step C: Preparation of (R)-ethyl 5-(2-(2-chloro-5-fluoropyridin-3-yl)pyrrolidin-1-yl)pyrazolo[1,5-a]pyrimidine-3-carboxylate To a solution of ethyl 5-hydroxypyrazolo[1,5-a]pyrimidine-3-carboxylate (Preparation B, Step A, 275 mg, 1.33 mmol) in anhydrous DMF (5 mL) was added (Benzotriazol-1-yloxy)tris(dimethylamino)phosphonium hexafluorophosphate (BOP) (646 mg, 1.46 mmol). The heterogeneous mixture was stirred for 10 minutes before adding DIEA (1.16 mL, 6.6 mmol), followed by addition of (R)-2-chloro-5-fluoro-3-(pyrrolidin-2-yl)pyridine dihydrochloride (363 mg, 1.33 mmol). The reaction was stirred at ambient temperature overnight to reach completion. The mixture was partitioned between 10% citric acid (30 mL) and EtOAc (30 mL), and the aqueous layer was extracted with EtOAc (2×20 mL). The combined organic phases were washed successively with water (20 mL), saturated NaHCO$_3$ (20 mL), water (20 mL) and brine (3×20 mL), then dried (Na$_2$SO$_4$) and concentrated to afford the crude product as an orange foam. The crude material was purified on a 25 g Biotage SNAP silica cartridge eluting with 1% MeOH/DCM to afford the desired product as cream-colored foam (0.35 g, 68% yield). MS (apci) m/z=390.0 (M+H).

Step D: Preparation of (R)-ethyl 5-(2-(2-(2-(tert-butoxycarbonylamino)ethylamino)-5-fluoropyridin-3-yl)pyrrolidin-1-yl)pyrazolo[1,5-a]pyrimidine-3-carboxylate A mixture of Pd$_2$dba$_3$ (7.05 mg, 0.00770 mmol), Cs$_2$CO$_3$ (125 mg, 0.385 mmol), rac-Binap (19.2 mg, 0.0308 mmol), (R)-ethyl 5-(2-(2-chloro-5-fluoropyridin-3-yl)pyrrolidin-1-yl)pyrazolo[1,5-a]pyrimidine-3-carboxylate (50 mg, 0.128 mmol), and tert-butyl 2-aminoethylcarbamate (24.7 mg, 0.154 mmol) in degassed toluene (1 mL) was first purged with nitrogen, then sealed and subjected to microwave irradiation (120° C.) for 16 hours. After cooled to ambient temperature, the reaction mixture was diluted with EtOAc (10 mL) and washed with water (2×5 mL). The organic was dried (Na$_2$SO$_4$) and concentrated. The crude material was purified by reverse phase column chromatography (Biotage SP4 system C18 12+M cartridge, 5 to 70% acetonitrile/water) to yield the desired product as white foamy solid (38 mg, 58% yield). MS (apci) m/z=514.1 (M−H).

Step E: Preparation of (R)-5-(2-(2-(2-(tert-butoxycarbonylamino)ethylamino)-5-fluoropyridin-3-yl)pyrrolidin-1-yl)pyrazolo[1,5-a]pyrimidine-3-carboxylic acid To a solution of (R)-ethyl 5-(2-(2-(2-(tert-butoxycarbonylamino)ethylamino)-5-fluoropyridin-3-yl)pyrrolidin-1-yl)pyrazolo[1,5-a]pyrimidine-3-carboxylate (38 mg, 0.074 mmol) in THF/MeOH/water (2:2:1, 0.7 mL) was added LiOH—H$_2$O (9.3 mg, 0.22 mmol), followed by stirring at 50° C. for 18 hours. After removal of solvent, the reaction residue was taken up in water (0.5 mL), and acidified with 1N HCl (0.22 mL) to pH 3. The reaction mixture was extracted with EtOAc (3×2 mL), dried (Na$_2$SO$_4$), filtered and concentrated to give the desired product, which was used in the next step directly without further purification, assuming quantitative conversion. MS (apci) m/z=486.0 (M+H).

Step F: Preparation of (R)-5-(2-(2-(2-aminoethylamino)-5-fluoropyridin-3-yl)pyrrolidin-1-yl)pyrazolo[1,5-a]pyrimidine-3-carboxylic acid hydrochloride A solution of (R)-5-(2-(2-(2-(tert-butoxycarbonylamino)ethylamino)-5-fluoropyridin-3-yl)pyrrolidin-1-yl)pyrazolo[1,5-a]pyrimidine-3-carboxylic acid (31 mg, 0.064 mmol) in HCl (4N dioxane, 798 μL) and TFA (50% DCM, 2 mL) was stirred at ambient temperature for 1 hour before it was concentrated and dried under high vacuum to yield to give the desired product as off-white solid, which was used in the next step directly without further purification, assuming quantitative conversion. MS (apci) m/z=386.1 (M+H).

Step G: Preparation of (6R)-9-fluoro-2,11,13,16,20,21,24-heptaazapentacyclo-[16.5.2.0$^{2,6}$.0$^{7,12}$.0$^{21,25}$]pentacosa-1(24),7,9,11,18(25),19,22-heptaen-17-one To a DMF (3 mL) solution of (R)-5-(2-(2-(2-aminoethylamino)-5-fluoropyridin-3-yl)pyrrolidin-1-yl)pyrazolo[1,5-a]pyrimidine-3-carboxylic acid (25 mg, 0.065 mmol) was first added HATU (29 mg, 0.077 mmol), followed by five-minute stirring and then drop-wise addition of DIEA (56 μL, 0.32 mmol). After stirring at ambient temperature overnight, the reaction was directly purified by reverse phase column chromatography (Biotage SP4 system C18 25+M cartridge, acetonitrile/water 5 to 45%), to yield the title product as off-white solid (7 mg, 30% yield). MS (apci) m/z=368.2 (M+H).

Example 13

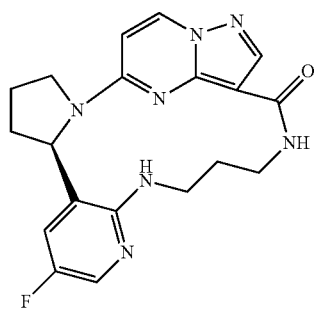 [SMILES: O=C1NCCCNc2ncc(F)cc2[C@H]2CCCN2c2ccn3ncc1c3n2]

(6R)-9-fluoro-2,11,13,17,21,22,25-heptaazapentacyclo[17.5.2.0$^{2,6}$.0$^{7,12}$.0$^{22,26}$]hexacosa-1(25),7,9,11,19(26),20,23-heptaen-18-one Step A: Preparation of (R)-ethyl 5-(2-(2-(3-(tert-butoxycarbonylamino) propylamino-5-fluoropyridin-3-yl)pyrrolidin-1-yl)pyrazolo[1,5-a]pyrimidine-3-carboxylate Prepared according to the method described in Example 12, Steps D, substituting tert-butyl 2-aminoethylcarbamate with tert-butyl 3-aminopropylcarbamate. MS (apci) m/z=528.1 (M+H).

Step B: Preparation of (6R)-9-fluoro-2,11,13,17,21, 22,25-heptaazapentacyclo-[17.5.2.0$^{2,6}$.0$^{7,12}$.0$^{22,26}$] hexacosa-1(25),7,9,11,19(26),20,23-heptaen-18-one Prepared according to the method described in Example 12, Steps E-G, in three steps, from (R)-ethyl 5-(2-(2-(3-(tert-butoxycarbonylamino)propylamino)-5-fluoropyridin-3-yl) pyrrolidin-1-yl)pyrazolo[1,5-a]pyrimidine-3-carboxylate obtained above. The crude product was purified by reverse phase column chromatography (Biotage SP4 system C-18 25+M cartridge, 5 to 50% acetonitrile/water), to provide the title product as white solid (6 mg, 44% yield). MS (apci pos) m/z=382.2 (M+H).

Example 14

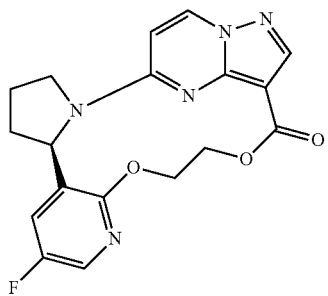 [SMILES: O=C1OCCOc2ncc(F)cc2[C@H]2CCCN2c2ccn3ncc1c3n2]

(6R)-9-fluoro-13,16-dioxa-2,11,20,21,24-pentaaza-pentacyclo[16.5.2.0$^{2,6}$.0$^{7,12}$.0$^{21,25}$]-pentacosa-1(24), 7,9,11,18(25),9,22-heptaen-17-one Step A: Preparation of (R)-2-chloroethyl 5-(2-(5-fluoro-2-methoxypyridin-3-yl)pyrrolidin-1-yl)pyrazolo[1,5-a]pyrimidine-3-carboxylate To a DMF (1 mL) suspension of (R)-5-(2-(5-fluoro-2-methoxypyridin-3-yl)pyrrolidin-1-yl)pyrazolo[1,5-a]pyrimidine-3-carboxylic acid (Preparation B, 0.1 g, 0.28 mmol) and HATU (0.128 g, 0.336 mmol) was added DIEA (0.146 ml, 0.840 mmol), followed by 2-chloroethanol (0.0270 g, 0.336 mmol). After stirring at ambient temperature for 30 minutes, the reaction was directly purified by reverse phase column chromatography (Biotage SP4 system C18 25+M, 5 to 65% acetonitrile/water) to obtain the intermediate (R)-3H-[1,2,3]triazolo[4,5-b]pyridin-3-yl 5-(2-(5-fluoro-2-methoxypyridin-3-yl)pyrrolidin-1-yl)pyrazolo [1,5-a]pyrimidine-3-carboxylate as white solid (94.7 mg, 71% yield). This isolated intermediate was dissolved in excess chloroethanol (1 mL), followed by addition of drops of DIEA at ambient temperature and stirred overnight to reach completion. The reaction was directly purified by reverse phase column chromatography (Biotage SP4 system C18 25+M, acetonitrile/water 5 to 73) to obtain the titled product as white foamy solid (56 mg, 48% yield). MS (apci) m/z=419.9 (M+H).

Step B: Preparation of (R)-2-chloroethyl 5-(2-(5-fluoro-2-oxo-1,2-dihydropyridin-3-yl)pyrrolidin-1-yl)pyrazolo[1,5-a]pyrimidine-3-carboxylate A mixture of (R)-2-chloroethyl 5-(2-(5-fluoro-2-methoxypyridin-3-yl)pyrrolidin-1-yl)pyrazolo[1,5-a]pyrimidine-3-carboxylate (56 mg, 0.13 mmol) in HCl (4N dioxane, 2.5 mL, 10 mmol) was sealed in a pressure reaction tube and heated at 100° C. for 45 minutes. The reaction mixture was cooled and concentrated to yield the product as yellowish oil, which was used directly in the next step without further purification, assuming quantitative yield. MS (apci) m/z=406.0 (M+H).

Step C: Preparation of (6R)-9-fluoro-13,16-dioxa-2, 11,20,21,24-pentaazapentacyclo[16.5.2.0$^{2,6}$.0$^{7,12}$. 0$^{21,25}$]-pentacosa-1(24),7,9,11,18(25),19,22-heptaen-17-one A mixture of (R)-2-chloroethyl 5-(2-(5-fluoro-2-oxo-12-dihydropyridin-3-yl)pyrrolidin-1-yl)pyrazolo[1,5-a]pyrimidine-3-carboxylate (54 mg, 0.133 mmol) and Cs$_2$CO$_3$ (217 mg, 0.665 mmol) in DMF (6 mL) was heated at 90° C. overnight. The reaction was filtered (GF/F paper) and directly purified by reverse phase column chromatography (Biotage SP4 system C18 25+M, 5 to 60% acetonitrile/water) to yield a mixture of desired product and impurities. This mixture was treated with a second column chromatography on Biotage SNAP KP-Sil 10 g, eluting with 10% hexanes/EtOAc to give the pure title product as a white solid (11 mg, 22% yield). MS (apci pos) m/z=370.2 (M+H).

Example 15

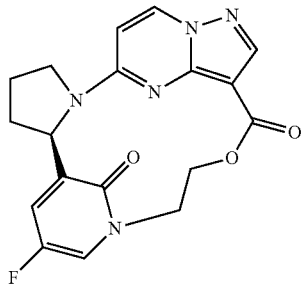 [SMILES: O=C1OCCn2cc(F)cc(c2=O)[C@H]2CCCN2c2ccn3ncc1c3n2]

(6R)-9-fluoro-14-oxa-2,11,18,19,22-pentaazapenta-cyclo[14.5.2.1$^{7,11}$.0$^{2,6}$.0$^{19,23}$]tetracosa-1(22),7,9,16 (23),17,20-hexaene-15,24-dione Obtained as a by-product of Example 14, Step C, and isolated as a white solid (5 mg, 9% yield) by reverse phase column chromatography (Biotage SP4 system C-18 25+M column, 5 to 60% acetonitrile/water) of the crude material of Example 14, Step C. MS (apci) m/z=370.2 (M+H).

Example 16

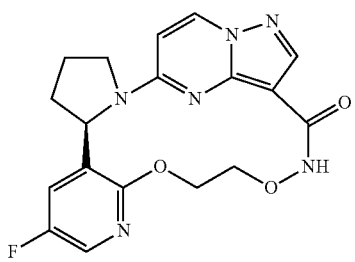 [SMILES: O=C1NOCCOc2ncc(F)cc2[C@H]2CCCN2c2ccn3ncc1c3n2]

(6R)-9-fluoro-13,16-dioxa-2,11,17,21,22,25-hexaazapentacyclo[17.5.2.0²,⁶.0⁷,¹².0²²,²⁶]hexacosa-1 (25),7,9,11,19(26),20,23-heptaen-18-one Step A: Preparation of (R)—N-(2-bromoethoxy)-5-(2-(5-fluoro-2-methoxypyridin-3-yl)pyrrolidin-1-yl)pyrazolo[1,5-a]pyrimidine-3-carboxamide To a mixture of (R)-5-(2-(5-fluoro-2-methoxypyridin-3-yl)pyrrolidin-1-yl)pyrazolo[1,5-a]pyrimidine-3-carboxylic acid (Preparation B, 100 mg, 0.280 mmol) and HATU (128 mg, 0.336 mmol) in DMF (1 mL) was added DIEA (0.146 mL, 0.840 mmol), followed by O-(2-bromoethyl)hydroxylamine hydrobromide (74.2 mg, 0.336 mmol) in one portion. After stirring at ambient temperature overnight, the reaction mixture was directly purified by reverse phase column chromatography (Biotage SP4 system C-18 25+M, 5 to 67% acetonitrile/water) to yield the desired product as off-white solid (91 mg, 68% yield). MS (apci) m/z=479.0 (M+H).

Step B: Preparation of (R)—N-(2-chloroethoxy)-5-(2-(5-fluoro-2-oxo-1,2-dihydropyridin-3-yl)pyrrolidin-1-yl)pyrazolo[1,5-a]pyrimidine-3-carboxamide A mixture of (R)—N-(2-bromoethoxy)-5-(2-(5-fluoro-2-methoxypyridin-3-yl)pyrrolidin-1-yl)pyrazolo[1,5-a]pyrimidine-3-carboxamide (70 mg, 0.146 mmol) and HCl (4N dioxane, 3.65 mL, 14.6 mmol) was sealed in a pressure tube and heated at 90° C. for 3 hours. The reaction mixture was then cooled, diluted with MeOH, concentrated, and dried on high vacuum to obtain the desired product which was used in the next step directly without further purification, assuming quantitative conversion.

Step C: Preparation of (6R)-9-fluoro-13,16-dioxa-2,11,17,21,22,25-hexaazapentacyclo[17.5.2.0²,⁶.0⁷,¹².0²²,²⁶]hexacosa-1(25),7,9,11,19(26),20,23-heptaen-18-one A mixture of (R)—N-(2-chloroethoxy)-5-(2-(5-fluoro-2-oxo-1,2-dihydropyridin-3-yl)pyrrolidin-1-yl)pyrazolo[1,5-a]pyrimidine-3-carboxamide (60 mg, 0.14 mmol) and Cs₂CO₃ (232 mg, 0.71 mmol) in DMF (1.4 mL) was heated at 90° C. for 20 minutes to reach completion. The reaction mixture was filtered (GF/F paper) and diluted with water (10 mL), then extracted with EtOAc (3×10 mL). The organic layers were combined, washed with brine and dried (Na₂SO₄). The crude material was purified on reverse phase column chromatography (Biotage SP4 system C18 12+M, acetonitrile/water 5 to 55%) to yield a mixture of the desired final product and impurities. This mixture was again purified by preparative TLC (10% MeOH/DCM) to yield the pure title product as white solid (1 mg, 1% yield). MS (apci) m/z=385.1 (M+H).

Example 17

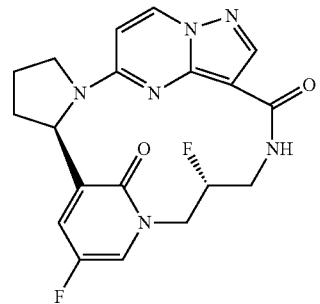 [SMILES: O=C1NC[C@@H](F)Cn2cc(F)cc(c2=O)[C@H]2CCCN2c2ccn3ncc1c3n2]

(6R,13R)-9,13-difluoro-2,11,15,19,20,23-hexaazapentacyclo[15.5.2.1⁷,¹¹.0²,⁶.0²⁰,²⁴]pentacosa-1(23),7,9,17(24),18,21-hexaene-16,25-dione A solution of (6R,13 S)-9-fluoro-13-hydroxy-2,11,15,19,20,23-hexaazapentacyclo-[15.5.2.1⁷,¹¹.0²,⁶.0²⁰,²⁴]pentacosa-1(23),7,9,17(24), 18,21-hexaene-16,25-dione (Example 5; 10 mg, 0.0251 mmol) in a mixture solvent of DCM (0.3 mL) and 3 drops of DMSO was treated with bis(2-methoxyethyl)amino-sulfur trifluoride (7.87 μL, 0.0427 mmol) at 0° C., followed by addition of a DCM (0.1 mL) solution of ethanol (0.231 mg, 0.00502 mmol), and the mixture was stirred at ambient temperature overnight. The reaction mixture was poured into saturated NaHCO₃ and extracted with DCM, then dried (Na₂SO₄), filtered, and concentrated. The crude material was purified by reverse phase column chromatography (Biotage SP4 system C18 12+M cartridge, acetonitrile/water 5 to 50%) to give the title product as beige solid (1.3 mg, 12% yield). MS (apci) m/z=401.2 (M+H).

Example 18

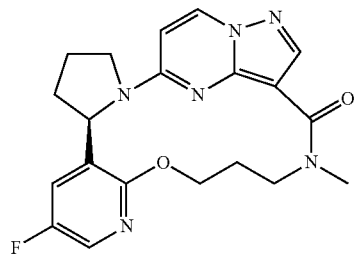 [SMILES: CN1CCCOc2ncc(F)cc2[C@H]2CCCN2c2ccn3ncc(c3n2)C1=O]

(6R)-9-fluoro-17-methyl-13-oxa-2,11,17,21,22,25-hexaazapentacyclo[17.5.2.0²,⁶.0⁷,¹².0²²,²⁶]hexacosa-1(25),7,9,11,19(26),20,23-heptaen-18-one Step A: Preparation of (R)—N-(3-chloropropyl)-5-(2-(5-fluoro-2-methoxypyridin-3-yl)pyrrolidin-1-yl)-N-methylpyrazolo[1,5-a]pyrimidine-3-carboxamide To a suspension of (R)-5-(2-(5-fluoro-2-methoxypyridin-3-yl)pyrrolidin-1-yl)pyrazolo[1,5-a]pyrimidine-3-carboxylic acid (Preparation B, 200 mg, 0.56 mmol) and 3-chloro-N-methylpropan-1-amine hydrochloride (177 mg, 1.23 mmol) in DMF (4 mL) was added N-methylmorpholine (0.25 mL, 2.30 mmol), followed by HATU (234 mg, 0.616 mmol). The reaction was stirred at ambient temperature for 18 hours, then diluted with H₂O (10 mL), and extracted EtOAc (2×20 mL). The combined organic extracts were washed with brine (20 mL), dried (MgSO₄), filtered, and concentrated. The crude product was purified by reverse-phase column chromatography, eluting with 5 to 60% acetonitrile/water to yield the desired product as a white foamy solid (129 mg, 52% yield). MS (apci) m/z=447.0 (M+H).

Step B: Preparation of (R)—N-(3-chloropropyl)-5-(2-(5-fluoro-2-oxo-1,2-dihydropyridin-3-yl)pyrrolidin-1-yl)-N-methylpyrazolo[1,5-a]pyrimidine-3-carboxamide A mixture of HCl (4N dioxane, 4 mL, 16.0 mmol) and (R)—N-(3-chloropropyl)-5-(2-(5-fluoro-2-methoxypyridin-3-yl)pyrrolidin-1-yl)-N-methylpyrazolo[1,5-a]pyrimidine-3-carboxamide (100 mg, 0.224 mmol) was sealed in a pressure tube and heated at 90° C. for 90 minutes. The reaction mixture was then diluted with acetonitrile and concentrated to yield the crude product, which was carried to the next step without further purification (145 mg, 150% yield). MS (apci) m/z=433.0 (M+H).

Step C: Preparation of (6R)-9-fluoro-17-methyl-13-oxa-2,11,17,21,22,25-hexaazapentacyclo[17.5.2.0²,⁶.0⁷,¹².0²²,²⁶]hexacosa-1(25),7,9,11,19(26),20,23-heptaen-18-one A mixture of (R)—N-(3-chloropropyl)-5-(2-(5-fluoro-2-oxo-1,2-dihydropyridin-3-yl)pyrrolidin-1-yl)-N-methylpyrazolo[1,5-a]pyrimidine-3-carboxamide (50 mg, 0.12 mmol) and Cs₂CO₃ (188 mg, 0.58 mmol) in DMF (12 mL) was heated at 90° C. for 15 minutes to reach completion. The reaction mixture was filtered, rinsed with DMF, and concentrated. The crude material was purified directly by reverse-phase column chromatography, eluting with 5 to 60% acetonitrile/water to yield the title product as pale yellow powder (17 mg, 36% yield). MS (apci) m/z=397.3 (M+H).

Example 19

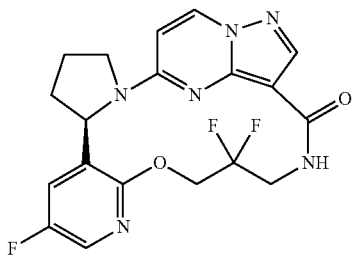 [SMILES: O=C1NCC(F)(F)COc2ncc(F)cc2[C@H]2CCCN2c2ccn3ncc1c3n2]

(6R)-9,15,15-trifluoro-13-oxa-2,11,17,21,22,25-hexaazapentacyclo[17.5.2.0²,⁶.0⁷,¹².0²²,²⁶]hexacosa-1(25),7,9,11,19(26),20,23-heptaen-18-one Step A: Preparation of (S)-1-amino-3-chloropropan-2-ol hydrochloride To a solution of benzaldehyde (4.50 g, 42.4 mmol) in EtOH (12 mL) was added aqueous ammonia (4.01 g, 65.9 mmol) in several portions. After stirring for 10 minutes, (S)-2-(chloromethyl)oxirane (3.81 g, 41.2 mmol) was added and the reaction mixture was stirred for 2 hours at ambient temperature. The reaction mixture was then heated at 35-40° C. with a heating mantle for 6 hours, followed by stirring at ambient temperature for 18 hours. The reaction was concentrated to 5 mL and toluene (5 mL) was added. The mixture was heated to 36° C. and a solution of concentrated HCl (6.09 g, 61.8 mmol) and water (5.9 mL) were added slowly over 5 minutes to maintain an internal reaction temperature range of 36-41° C. The biphasic mixture was heated at 42-45° C. for 3 hours. The organic phase was separated and washed with water (10 mL). The aqueous phases were combined and ethanol (10 mL) was added. The mixture was concentrated to 10 mL, and ethanol (6×10 mL) was added, concentrating after each addition. After the last concentration step, the slurry was warmed to reflux, cooled to ambient temperature, and then placed at −20° C. for 18 hours. The product was collected by vacuum filtration, washed with cold ethanol, and vacuum-dried, to provide the product as white crystalline solid (3.58 g, 60% yield). ¹H NMR (d⁶-DMSO) δ 8.14 (s, 3H), 5.91 (s, 1H), 3.93 (m, 1H), 3.59 (m, 2H), 2.89 (m, 1H), 2.69 (m, 1H).

Step B: Preparation of N—((S)-3-chloro-2-hydroxypropyl)-5-((R)-2-(5-fluoro-2-methoxypyridin-3-yl)pyrrolidin-1-yl)pyrazolo[1,5-a]pyrimidine-3-carboxamide Prepared according to the method described in Example 18, substituting (S)-1-amino-3-chloropropan-2-ol hydrochloride (98.1 mg, 0.672 mmol) for 3-chloro-N-methylpropan-1-amine hydrochloride in Step A. MS (apci) m/z=448.9 (M+H).

Step C: Preparation of (R)—N-(3-chloro-2-oxopropyl)-5-(2-(5-fluoro-2-methoxypyridin-3-yl)pyrrolidin-1-yl)pyrazolo[1,5-a]pyrimidine-3-carboxamide To a solution of N—((S)-3-chloro-2-hydroxypropyl)-5-((R)-2-(5-fluoro-2-methoxypyridin-3-yl)pyrrolidin-1-yl)pyrazolo[1,5-a]pyrimidine-3-carboxamide (180 mg, 0.401 mmol) in DCM (3 mL) was added Dess-Martin periodinane (204 mg, 0.481 mmol). The reaction was stirred at ambient temperature for 3 hours, then purified directly by reverse-phase column chromatography, eluting with 5 to 60% acetonitrile/water to yield the desired product as a white foamy solid (114 mg, 64% yield). MS (apci) m/z=447.0 (M+H).

Step D: Preparation of (R)—N-(3-chloro-2,2-difluoropropyl)-5-(2-(5-fluoro-2-methoxypyridin-3-yl)pyrrolidin-1-yl)pyrazolo[1,5-a]pyrimidine-3-carboxamide To a solution of (R)—N-(3-chloro-2-oxopropyl)-5-(2-(5-fluoro-2-methoxypyridin-3-yl)pyrrolidin-1-yl)pyrazolo[1,5-a]pyrimidine-3-carboxamide (114 mg, 0.255 mmol) in DCM (3 mL) was added Deoxofluor (0.103 mL, 0.561 mmol), and the reaction mixture was stirred at ambient temperature for 23 hours. The reaction was quenched with saturated NaHCO₃ (5 mL), diluted with DCM (5 mL), and stirred for 30 minutes. After phase separation, the aqueous phase was extracted with DCM (10 mL). The combined organic phases were concentrated and purified by reverse-phase column chromatography, eluting with 5 to 60% acetonitrile/water to yield the desired product as white solid (59 mg, 49% yield). MS (apci) m/z=469.0 (M+H).

Step E: Preparation of (R)—N-(3-chloro-2,2-difluoropropyl)-5-(2-(5-fluoro-2-oxo-1,2-dihydropyridin-3-yl)pyrrolidin-1-yl)pyrazolo[1,5-a]pyrimidine-3-carboxamide Prepared according to the method described in Example 18, substituting (R)—N-(3-chloro-2,2-difluoropropyl)-5-(2-(5-fluoro-2-methoxypyridin-3-yl)pyrrolidin-1-yl)pyrazolo[1,5-a]pyrimidine-3-carboxamide for (R)—N-(3-chloropropyl)-5-(2-(5-fluoro-2-methoxypyridin-3-yl)pyrrolidin-1-yl)-N-methylpyrazolo[1,5-a]pyrimidine-3-carboxamide in Step B. MS (apci) m/z=455.0 (M+H).

Step F: Preparation of (6R)-9,15,15-trifluoro-13-oxa-2,11,17,21,22,25-hexaazapentacyclo[17.5.2.0$^{2,6}$.0$^{7,12}$.0$^{22,26}$]hexacosa-1(25),7,9,11,19(26),20,23-heptaen-18-one Prepared according to the same method as described in Example 18, substituting (R)—N-(3-chloro-2,2-difluoropropyl)-5-(2-(5-fluoro-2-oxo-1,2-dihydropyridin-3-yl)pyrrolidin-1-yl)pyrazolo[1,5-a]pyrimidine-3-carboxamide for (R)—N-(3-chloropropyl)-5-(2-(5-fluoro-2-oxo-1,2-dihydropyridin-3-yl)pyrrolidin-1-yl)-N-methylpyrazolo[1,5-a]pyrimidine-3-carboxamide in Step C, and heating at 110° C. for 5 hours, to provide the title product as a pale pink solid (6 mg, 11% yield). MS (apci) m/z=419.3 (M+H).

Example 20

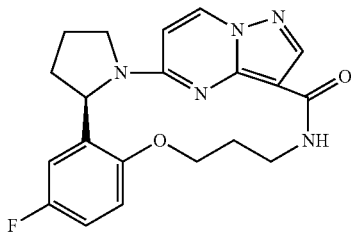 [SMILES: O=C1NCCCOc2ccc(F)cc2[C@H]2CCCN2c2ccn3ncc1c3n2]

(6R)-9-fluoro-13-oxa-2,17,21,22,25-pentaazapentacyclo[17.5.2.0$^{2,6}$.0$^{7,12}$.0$^{22,26}$]hexacosa-1(25),7,9,11,19(26),20,23-heptaen-18-one Step A: Preparation of (R)-tert-butyl 2-(5-fluoro-2-hydroxyphenyl)pyrrolidine-1-carboxylate This compound was prepared according to the method described in Preparation A, substituting 3-bromo-5-fluoro-2-methoxypyridine with 2-bromo-4-fluorophenyl acetate in Step A (3.2 g, 40% yield). MS (apci) m/z=182.1 (M+H–Boc).

Step B: Preparation of (R)-4-fluoro-2-(pyrrolidin-2-yl)phenol hydrochloride

To a solution of (R)-tert-butyl 2-(5-fluoro-2-hydroxyphenyl)pyrrolidine-1-carboxylate (3.2 g, 11.4 mmol) in DCM (20 mL) was added HCl (4N dioxane, 5.69 mL, 22.7 mmol), and the mixture was stirred at ambient temperature for 15 hours. The reaction was concentrated, and the resulting precipitate was taken up in DCM (15 mL) and filtered to afford (R)-4-fluoro-2-(pyrrolidin-2-yl)phenol hydrochloride (1.85 g, 90% yield) as a beige solid. MS (apci) m/z=182.1 (M+H).

Step C: Preparation of (R)-ethyl 5-(2-(5-fluoro-2-hydroxyphenyl)pyrrolidin-1-yl)pyrazolo[1,5-a]pyrimidine-3-carboxylate Prepared according to the method described in Preparation B, substituting (R)-4-fluoro-2-(pyrrolidin-2-yl)phenol hydrochloride for (R)-5-fluoro-2-methoxy-3-(pyrrolidin-2-yl)pyridine in Step C. The crude material was purified by reverse-phase column chromatography (0-65% acetonitrile/H$_2$O) to yield the pure product (686 mg, 80% yield). MS (apci) m/z=371.0 (M+H).

Step D: Preparation of (R)-ethyl 5-(2-(2-(3-(1,3-dioxoisoindolin-2-yl)propoxy)-5-fluorophenyl)pyrrolidin-1-yl)pyrazolo[1,5-a]pyrimidine-3-carboxylate A suspension of (R)-ethyl 5-(2-(5-fluoro-2-hydroxyphenyl)pyrrolidin-1-yl)pyrazolo[1,5-a]pyrimidine-3-carboxylate (280 mg, 0.756 mmol), 2-(3-bromopropyl)isoindoline-1,3-dione (263 mg, 0.983 mmol) and K$_2$CO$_3$ (104 mg, 0.756 mmol) in DMF (0.4 mL) was stirred at ambient temperature for 15 hours. The reaction was directly purified by reverse-phase column chromatography (5-80% acetonitrile/H$_2$O) to afford (R)-ethyl 5-(2-(2-(3-(1,3-dioxoisoindolin-2-yl)propoxy)-5-fluorophenyl)pyrrolidin-1-yl)pyrazolo[1,5-a]pyrimidine-3-carboxylate (202 mg, 48% yield) as clear oil. MS (apci) m/z=558.0 (M+H).

Step E: Preparation of (R)-ethyl 5-(2-(2-(3-aminopropoxy)-5-fluorophenyl)pyrrolidin-1-yl)pyrazolo[1,5-a]pyrimidine-3-carboxylate (R)-ethyl 5-(2-(2-(3-(1,3-dioxoisoindolin-2-yl)propoxy)-5-fluorophenyl)pyrrolidin-1-yl)pyrazolo[1,5-a]pyrimidine-3-carboxylate (200 mg, 0.359 mmol) and hydrazine monohydrate (115 mg, 3.59 mmol) were combined in MeOH (1 mL) and THF (1 mL) in a sealed vessel and heated at 60° C. for 20 minutes. After cooling to ambient temperature, the reaction was concentrated, followed by addition of NaOH (1N, 2 mL). The mixture was extracted with DCM, and the combined organic extracts were dried (Na$_2$SO$_4$), filtered and concentrated to afford (R)-ethyl 5-(2-(2-(3-aminopropoxy)-5-fluorophenyl)pyrrolidin-1-yl)pyrazolo[1,5-a]pyrimidine-3-carboxylate (110 mg, 72% yield). MS (apci) m/z=428.2 (M+H).

Step F: Preparation of (6R)-9-fluoro-13-oxa-2,17,21,22,25-pentaazapentacyclo[17.5.2.0$^{2,6}$.0$^{7,12}$.0$^{22,26}$]hexacosa-1(25),7,9,11,19(26),20,23-heptaen-18-one (R)-ethyl 5-(2-(2-(3-aminopropoxy)-5-fluorophenyl)pyrrolidin-1-yl)pyrazolo[1,5-a]pyrimidine-3-carboxylate (10 mg, 0.023 mmol) and DIEA (8.1 µL, 0.047 mmol) were combined in dry EtOH (0.1 mL) in a sealed vessel and heated at 200° C. overnight. The reaction was concentrated and purified by reverse-phase column chromatography (0-70% acetonitrile/H$_2$O) to afford the title compound (4.5 mg, 50% yield). MS (apci) m/z=382.2 (M+H).

Example 21

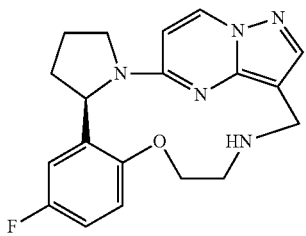 [SMILES: Fc1ccc2c(c1)[C@H]1CCCN1c1ccn3ncc(c3n1)CNCCO2]

(6R)-9-fluoro-13-oxa-2,16,20,21,24-pentaazapentacyclo[16.5.2.0$^{2,6}$.0$^{7,12}$.0$^{21,25}$]pentacosa-1(24),7,9,11,18(25),19,22-heptaene

Step A: Preparation of (R)-4-fluoro-2-(1-(pyrazolo[1,5-a]pyrimidin-5-yl)pyrrolidin-2-yl)phenol A mixture of (R)-4-fluoro-2-(pyrrolidin-2-yl)phenol hydrochloride (Example 20, Step B, 1.50 g, 6.89 mmol), DIEA (2.67 g, 20.7 mmol), 5-chloropyrazolo[1,5-a]pyrimidine (1.11 g, 7.24 mmol) and isopropanol (1 mL) was heated at 120° C. overnight. The reaction was poured into ether (50 mL) and extracted with NaOH (1N aqueous, 3×25 mL). The combined aqueous extracts were brought to pH 4 with concentrated HCl and extracted with DCM. The combined DCM extracts were filtered through phase separator paper and concentrated to provide (R)-4-fluoro-2-(1-(pyrazolo[1,5-a]pyrimidin-5-yl)pyrrolidin-2-yl)phenol (1.82 g, 89% yield) as beige solid. MS (apci) m/z=299.4 (M+H).

Step B: Preparation of (R)-5-(2-(5-fluoro-2-hydroxyphenyl)pyrrolidin-1-yl)pyrazolo[1,5-a]pyrimidine-3-carbaldehyde After POCl$_3$ (221 µL, 2.41 mmol) was added drop-wise to a DMF (4 mL) solution of (R)-4-fluoro-2-(1-(pyrazolo[1,5-a]pyrimidin-5-yl)pyrrolidin-2-yl)phenol (600 mg, 2.01 mmol) at ambient temperature, the reaction was stirred for 5 minutes before NaOH (804 mg, 10.1 mmol) was introduced. The reaction was stirred for another 10 minutes before HCl (4N dioxane, 3 mL) was added, followed by DCM (50 mL). After filtering through Celite®, the reaction was concentrated and purified by reverse-phase column chromatography, eluting with 0-70% acetonitrile/H$_2$O to provide (R)-5-(2-(5-fluoro-2-hydroxyphenyl)pyrrolidin-1-yl)pyrazolo[1,5-a]pyrimidine-3-carbaldehyde (524 mg, 80% yield) as beige solid. MS (apci) m/z=327.2 (M+H).

Step C: Preparation of (R)-tert-butyl 2-(4-fluoro-2-(1-(3-formylpyrazolo[1,5-a]pyrimidin-5-yl)pyrrolidin-2-yl)phenoxy)ethylcarbamate A mixture of (R)-5-(2-(5-fluoro-2-hydroxyphenyl)pyrrolidin-1-yl)pyrazolo[1,5-a]pyrimidine-3-carbaldehyde (159 mg, 0.487 mmol), tert-butyl 2-bromoethylcarbamate (131 mg, 0.585 mmol), potassium carbonate (202 mg, 1.46 mmol) and DMF (1 mL) was combined in a sealed vessel and stirred at ambient temperature overnight and then at 60° C. for 3 hours. After diluting with DCM (20 mL), the reaction was filtered through Celite®, concentrated and purified by reverse-phase column chromatography, eluting with 0-70% acetonitrile/H$_2$O to provide (R)-tert-butyl 2-(4-fluoro-2-(1-(3-formylpyrazolo[1,5-a]pyrimidin-5-yl)pyrrolidin-2-yl)phenoxy)ethylcarbamate (198 mg, 86.6% yield) as yellowish solid. MS (apci) m/z=370.4 (M+H–Boc).

Step D: Preparation of (R)-5-(2-(2-(2-aminoethoxy)-5-fluorophenyl)pyrrolidin-1-yl)pyrazolo[1,5-a]pyrimidine-3-carbaldehyde An HCl (4N dioxane, 80 µl, 0.32 mmol) was added to a DCM (2 mL) solution of (R)-tert-butyl 2-(4-fluoro-2-(1-(3-formylpyrazolo[1,5-a]pyrimidin-5-yl)pyrrolidin-2-yl)phenoxy)ethylcarbamate (198 mg, 0.422 mmol), and the reaction was purged with N$_2$ and stirred at ambient temperature overnight. After removal of solvent, NaOH (5 mL×1N) was introduced and the reaction mixture was extracted with several portions of DCM in a phase separator tube. The combined organic extracts were concentrated to provide (R)-5-(2-(2-(2-aminoethoxy)-5-fluorophenyl)pyrrolidin-1-yl)pyrazolo[1,5-a]pyrimidine-3-carbaldehyde (155 mg, 99.5% yield), which was used immediately in the next step. MS (apci) m/z=352.3 (M+H–H$_2$O).

Step E: Preparation of (6R)-9-fluoro-13-oxa-2,16,20,21,24-pentaazapentacyclo[16.5.2.0$^{2,6}$.0$^{7,12}$.0$^{21,25}$]pentacosa-1(24),7,9,11,18(25),19,22-heptaene Tetramethylammonium triacetoxyborohydride (46.7 mg, 0.629 mmol) was added to a DCM (50 mL) solution of (R)-5-(2-(2-(2-aminoethoxy)-5-fluorophenyl)pyrrolidin-1-yl)pyrazolo[1,5-a]pyrimidine-3-carbaldehyde (155 mg, 0.420 mmol), and the reaction was stirred at ambient temperature overnight. The reaction mixture was then diluted with brine and extracted with several portions of DCM in a phase separator tube, and the combined organic extracts were concentrated and purified by reverse-phase column chromatography, eluting with 0-90% acetonitrile-H$_2$O, to obtain the title product (32 mg, 21.6% yield). MS (apci) m/z=354.2 (M+H).

Example 22

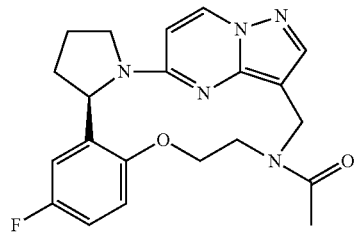 [SMILES: CC(=O)N1CCOc2ccc(F)cc2[C@H]2CCCN2c2ccn3ncc(c3n2)C1]

1-[(6R)-9-fluoro-13-oxa-2,16,20,21,24-pentaazapentacyclo[16.5.2.0$^{2,6}$.0$^{7,12}$.0$^{21,25}$]pentacosa-1(24),7,9,11,18(25),19,22-heptaen-16-yl]ethan-1-one Acetyl chloride (1.7 mg, 0.021 mmol) was added to a DCM (0.5 mL) solution of (6R)-9-fluoro-13-oxa-2,16,20,21,24-pentaazapentacyclo-[16.5.2.0$^{2,6}$.0$^{7,12}$.0$^{21,25}$]pentacosa-1(24),7,9,11,18(25),19,22-heptaene (Example 21, 5.0 mg, 0.014 mmol), followed by DIEA (7.4 µL, 0.042 mmol). After stirring at ambient temperature overnight, the reaction was concentrated and purified by reverse-phase column chromatography eluting with 0-80% acetonitrile/H₂O to provide the title product (3.9 mg, 70% yield). MS (apci) m/z=396.2 (M+H).

Example 23

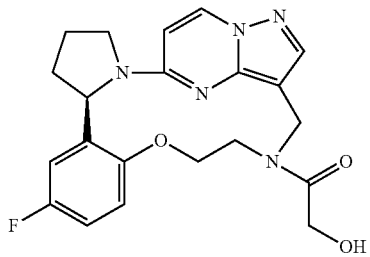 [SMILES: O=C(CO)N1CCOc2ccc(F)cc2[C@H]2CCCN2c2ccn3ncc(c3n2)C1]

1-[(6R)-9-fluoro-13-oxa-2,16,20,21,24-pentaazapentacyclo[16.5.2.0²,⁶.0⁷,¹².0²¹,²⁵]pentacosa-1(24),7,9,11,18(25),19,22-heptaen-16-yl]-2-hydroxyethan-1-one To a DCM (0.5 mL) solution of (6R)-9-fluoro-13-oxa-2,16,20,21,24-pentaazapentacyclo-[16.5.2.0²,⁶.0⁷,¹².0²¹,²⁵]pentacosa-1(24),7,9,11,18(25),19,22-heptaene (Example 21, 6 mg, 0.017 mmol) was added 2-chloro-2-oxoethyl acetate (3.5 mg, 0.025 mmol), followed by DIEA (8.9 µL, 0.051 mmol). The reaction was stirred at ambient temperature overnight, then concentrated, and MeOH (0.2 mL) was added followed by sodium hydroxide (6.8 mg, 0.085 mmol). After stirring at ambient temperature for 5 hours, the reaction was diluted with brine and extracted with several portions of DCM in a phase separator tube. The combined organic extracts were concentrated and purified by reverse-phase column chromatography, eluting with 0-70% acetonitrile/H₂O, to provide the title product (3.6 mg, 52%/0 yield). MS (apci) m/z=412.5 (M+H).

Example 24

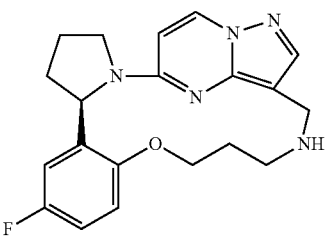 [SMILES: Fc1ccc2c(c1)[C@H]1CCCN1c1ccn3ncc(c3n1)CNCCCO2]

(6R)-9-fluoro-13-oxa-2,17,21,22,25-pentaazapentacyclo[17.5.2.0²,⁶.0⁷,¹².0²²,²⁶]hexacosa-1(25),7,9,11,19(26),20,23-heptaene Step A: Preparation of (R)-tert-butyl 3-(4-fluoro-2-(1-(3-formylpyrazolo[1,5-a]pyrimidin-5-yl)pyrrolidin-2-yl)phenoxy)propylcarbamate Prepared according to the method described in Example 21, substituting tert-butyl 2-bromoethylcarbamate with tert-butyl 3-bromopropylcarbamate in Step C to afford the desired product (119 mg, 84.5% yield). MS (apci) m/z=384.2 (M+H–Boc).

Step B: Preparation of (R)-tert-butyl 3-(4-fluoro-2-(1-(3-(hydroxymethyl)pyrazolo[1,5-a]pyrimidin-5-yl)pyrrolidin-2-yl)phenoxy)propylcarbamate A solution of (R)-tert-butyl 3-(4-fluoro-2-(1-(3-formylpyrazolo[1,5-a]pyrimidin-5-yl)pyrrolidin-2-yl)phenoxy)propylcarbamate (85.0 mg, 0.176 mmol) in MeOH (2 mL) was first cooled to 0° C., then NaBH₄ (4.04 mg, 0.176 mmol) was introduced, and the reaction was stirred at 0° C. for 1 hour. The reaction was diluted with brine and extracted with DCM in a phase separator cartridge. The combined organic extracts were concentrated to provide (R)-tert-butyl 3-(4-fluoro-2-(1-(3-(hydroxymethyl)pyrazolo[1,5-a]pyrimidin-5-yl)pyrrolidin-2-yl)phenoxy)propylcarbamate (86 mg, 101% yield) as beige solid. MS (apci) m/z=468.1 (M+H–H₂O).

Step C: Preparation of (R-(5-(2-(2-(3-aminopropoxy)-5-fluorophenyl)pyrrolidin-yl)pyrazolo[1,5-a]pyrimidin-3-yl)methanol hydrochloride (R)-tert-butyl 3-(4-fluoro-2-(1-(3-(hydroxymethyl)pyrazolo[1,5-a]pyrimidin-5-yl)pyrrolidine-2-yl)phenoxy)propylcarbamate (80 mg, 0.16 mmol) was dissolved in 2 mL of DCM and treated with HCl (4N in dioxane, 6.0 mg, 0.16 mmol). The reaction was purged with N₂, capped, and stirred at ambient temperature for 18 hours, then concentrated to provide (R)-(5-(2-(2-(3-aminopropoxy)-5-fluorophenyl) pyrrolidine-1-yl)pyrazole[1,5-a]pyrimidin-3-yl)methanol hydrochloride (70 mg, 101% yield) as a beige solid. MS (apci) m/z=368.5 (M+H–H₂O).

Step D: Preparation of (6R)-9-fluoro-13-oxa-2,17,21,22,25-pentaazapentacyclo-[17.5.2.0²,⁶.0⁷,¹².0²²,²⁶]hexacosa-1(25),7,9,11,19(26),20,23-heptaene A mixture of (R)-(5-(2-(2-(3-aminopropoxy)-5-fluorophenyl)pyrrolidin-1-yl)pyrazolo[1,5-a]pyrimidin-3-yl) methanol (50 mg, 0.130 mmol), PS-PPh₃ (0.259 mmol) and perchloromethane (200 mg, 1.30 mmol) in DCM (5 mL) was shaken at ambient temperature overnight. The reaction was filtered, concentrated and purified by reverse-phase column chromatography eluting with 0-60% acetonitrile/H₂O to yield the title product (27.4 mg, 57.5% yield). MS (apci) m/z=368.1 (M+H).

Example 25

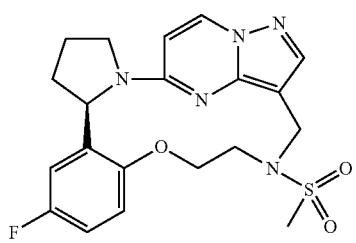 [SMILES: CS(=O)(=O)N1CCOc2ccc(F)cc2[C@H]2CCCN2c2ccn3ncc(c3n2)C1]

(6R)-9-fluoro-16-methanesulfonyl-13-oxa-2,16,20,
21,24-pentaazapentacyclo[16.5.2.0$^{2,6}$.0$^{7,12}$.0$^{21,25}$]
pentacosa-1(24),7,9,11,18(25),19,22-heptaene To a DCM (0.5 mL) solution of (6R)-9-fluoro-13-oxa-2,
16,20,21,24-pentaazapentacyclo-[16.5.2.0$^{2,6}$.0$^{7,12}$.0$^{21,25}$]
pentacosa-(24),7,9,11,18(25),19,22-heptaene (Example 21,
5 mg, 0.0141 mmol) was added DIEA (2.46 µL, 0.0141
mmol), followed by methanesulfonyl chloride (1.10 µL,
0.0141 mmol). The reaction was stirred at ambient temperature for 1 hour before MeOH (0.1 mL) was added. The reaction was concentrated and purified by reverse-phase column chromatography eluting with 0-80% acetonitrile/H$_2$O to provide the title product (3.1 mg, 50.8% yield). MS (apci) m/z=432.3 (M+H).

Example 26

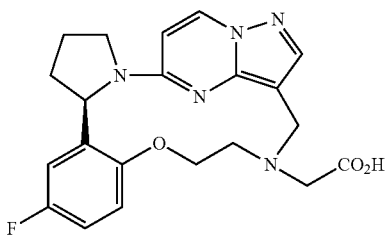 [SMILES: O=C(O)CN1CCOc2ccc(F)cc2[C@H]2CCCN2c2ccn3ncc(c3n2)C1]

2-[(6R)-9-fluoro-13-oxa-2,16,20,21,24-pentaazapentacyclo[16.5.2.0$^{2,6}$.0$^{7,12}$.0$^{21,25}$]pentacosa-1(24),7,9,
11,18(25),19,22-heptaen-16-yl]acetic acid An IPA (0.1 mL) solution of (6R)-9-fluoro-13-oxa-2,16,
20,21,24-pentaazapentacyclo-[16.5.2.0$^{2,6}$.0$^{7,12}$.0$^{21,25}$]pentacosa-1 (24),7,9,11,18(25), 19,22-heptaene (Example 21, 5 mg, 0.014 mmol), 2-bromoacetic acid (2.9 mg, 0.021 mmol) and NaOH (1N, 42 µL, 0.042 mmol) was heated at 60° C. in a sealed vessel overnight, then at 120° C. for 24 hours. After cooling, the reaction mixture was directly purified by reverse-phase column chromatography eluting with 0-50% acetonitrile/H$_2$O to afford the title product (3.1 mg, 53% yield). MS (apci) m/z=412.2 (M+H).

Example 27

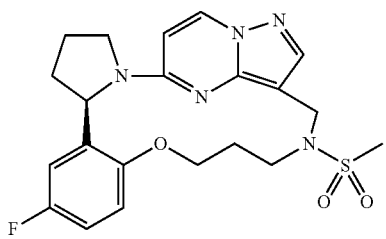 [SMILES: CS(=O)(=O)N1CCCOc2ccc(F)cc2[C@H]2CCCN2c2ccn3ncc(c3n2)C1]

(6R)-9-fluoro-17-methanesulfonyl-13-oxa-2,17,21,
22,25-pentaazapentacyclo[17.5.2.0$^{2,6}$.0$^{7,12}$.0$^{22,26}$]
hexacosa-1(25),7,9,11,19(26),20,23-heptaene Methanesulfonyl chloride (1.69 µL, 0.0218 mmol) was added to a DCM (0.5 mL) solution of (6R)-9-fluoro-13-oxa-2,17,21,22,25-pentaazapentacyclo[17.5.2.0$^{2,6}$.0$^{7,12}$.0$^{22,26}$]
hexacosa-1(25),7,9,11,19(26),20,23-heptaene (Example 24, 4.0 mg, 0.0109 mmol), followed by DIEA (9.48 µL, 0.0544 mmol). The reaction was stirred at ambient temperature overnight, concentrated and purified by reverse-phase column chromatography eluting with 0-80% acetonitrile/H$_2$O to afford the title compound (2.9 mg, 59.8% yield). MS (apci) m/z=446.3 (M+H).

Example 28

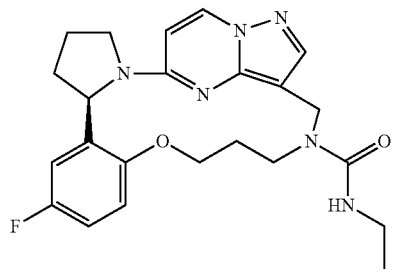 [SMILES: CCNC(=O)N1CCCOc2ccc(F)cc2[C@H]2CCCN2c2ccn3ncc(c3n2)C1]

(6R)—N-ethyl-9-fluoro-3-oxa-2,17,21,22,25-pentaazapentacyclo[17.5.2.0$^{2,6}$.0$^{7,12}$.0$^{22,26}$]hexacosa-1
(25),7,9,11,19(26),20,23-heptaene-17-carboxamide To a DCM (0.5 mL) solution of (6R)-9-fluoro-13-oxa-2,
17,21,22,25-pentaazapentacyclo[17.5.2.0$^{2,6}$.0$^{7,12}$.0$^{22,26}$]
hexacosa-1(25),7,9,11,19(26),20,23-heptaene (Example 24, 4 mg, 0.011 mmol) was added isocyanatoethane (1.5 mg, 0.022 mmol) followed by DIEA (1.9 µL, 0.011 mmol). The reaction was stirred at ambient temperature overnight, then concentrated and purified by reverse-phase column chromatography, eluting with 0-80% acetonitrile/H$_2$O, to afford the title compound (3.5 mg, 73% yield). MS (apci) m/z=439.1 (M+H).

Example 29

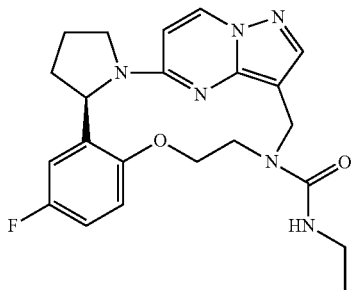 [SMILES: CCNC(=O)N1CCOc2ccc(F)cc2[C@H]2CCCN2c2ccn3ncc(c3n2)C1]

(6R)—N-ethyl-9-fluoro-13-oxa-2,16,20,21,24-pentaazapentacyclo-[16.5.2.0$^{2,6}$.0$^{7,12}$.0$^{21,25}$]pentacosa-1
(24),7,9,11,18(25),19,22-heptaene-16-carboxamide To a DCM (0.5 mL) solution of (6R)-9-fluoro-13-oxa-2,
16,20,21,24-pentaazapentacyclo[16.5.2.0$^{2,6}$.0$^{7,12}$.0$^{21,25}$]
pentacosa-1(24),7,9,11,18(25), 19,22-heptaene (Example 21, 5.5 mg, 0.016 mmol) was added isocyanatoethane (1.5 mg, 0.022 mmol), followed by DIEA (1.9 µL, 0.011 mmol).

After stirring at ambient temperature overnight the reaction was concentrated and purified by reverse-phase column chromatography, eluting with 0-80% acetonitrile/H₂O to afford the title compound (3.3 mg, 50% yield). MS (apci) m/z=425.4 (M+H).

Example 30

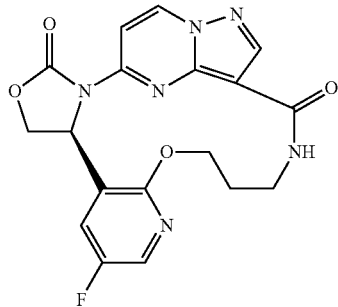 [SMILES: O=C1NCCCOc2ncc(F)cc2[C@H]2COC(=O)N2c2ccn3ncc1c3n2]

(6S)-9-fluoro-4,13-dioxa-2,11,17,21,22,25-hexaazapentacyclo[17.5.2.0$^{2,6}$.0$^{7,12}$.0$^{22,26}$]hexacosa-1(25),7(12),8,10,19(26),20,23-heptaene-3,18-dione Step A: Preparation of (S,E)-N-(2-(tert-butyldimethylsilyloxy)ethylidene)-2-methylpropane-2-sulfinamide To a solution of (S)-2-methylpropane-2-sulfinamide (3.3 g, 27.2 mmol) in DCM (50 mL) was added 2-(tert-butyldimethylsilyloxy)acetaldehyde (4.98 g, 28.6 mmol) followed by anhydrous copper sulfate (8.69 g, 54.5 mmol). The heterogeneous mixture was stirred at ambient temperature for 3 days and then filtered through Celite®. The filtrate concentrated and the residue was purified by flash column chromatography, eluting with 10% EtOAc/hexanes, to afford (S,E)-N-(2-(tert-butyldimethylsilyloxy)ethylidene)-2-methylpropane-2-sulfinamide (5.54 g, 73% yield) as a colorless oil. $^1$H NMR (CDCl₃) δ 7.96 (m, 1H), 4.44 (d, 1H, J=2.7 Hz), 1.11 (s, 9H), 0.82 (s, 9H), 0.00 (s, 6H).

Step B: Preparation of (S)—N—((S)-2-(tert-butyldimethylsilyloxy)-1-(5-fluoro-2-methoxypyridin-3-yl)ethyl)-2-methylpropane-2-sulfinamide To a solution of n-butyl lithium (10.8 mL, 17.3 mmol, 1.6M in hexanes) in toluene (100 mL) at −78° C. was added a solution of 3-bromo-5-fluoro-2-methoxypyridine (3.27 g, 15.9 mmol) in toluene (5 mL) dropwise, maintaining the internal temperature below −70° C. The mixture was stirred at −78° C. for 1 hour, then treated with a solution of (S,E)-N-(2-(tert-butyldimethylsilyloxy)ethylidene)-2-methylpropane-2-sulfinamide (4.0 g, 14.4 mmol) in toluene (10 mL) dropwise, maintaining the internal temperature below −65° C. After stirring at −78° C. for 3 hours the mixture was treated with brine (100 mL) and EtOAc (100 mL) and stirred at ambient temperature for 20 minutes. Saturated NaHCO₃ solution (50 mL) was added and the layers were separated. The aqueous layer was extracted with EtOAc (2×50 mL) and the combined organic phases were washed with brine (50 mL), dried over Na₂SO₄, filtered and concentrated. The residue was purified by flash column chromatography, eluting with 10% EtOAc/hexanes to 20% EtOAc/hexanes, to afford (S)—N—((S)-2-(tert-butyldimethylsilyloxy)-1-(5-fluoro-2-methoxypyridin-3-yl)ethyl)-2-methylpropane-2-sulfinamide (1.40 g, 24% yield) mixed with a less polar impurity as a colorless oil. MS (apci) m/z=405.0 (M+H).

Step C: Preparation of (S)-2-amino-2-(5-fluoro-2-methoxypyridin-3-yl)ethanol dihydrochloride To a solution of (S)—N—((S)-2-(tert-butyldimethylsilyloxy)-1-(5-fluoro-2-methoxypyridin-3-yl)ethyl)-2-methylpropane-2-sulfinamide (1.40 g, 3.46 mmol) in methanol (20 mL) was added 4N HCl/dioxane (8.65 mL, 34.6 mmol). The solution was stirred at ambient temperature for 16 hours, then concentrated and dried under vacuum to afford (S)-2-amino-2-(5-fluoro-2-methoxypyridin-3-yl)ethanol dihydrochloride as a yellow oil which was used without purification, assuming 100% yield. MS (apci) m/z=186.9 (M+H).

Step D: Preparation of (S)-4-(5-fluoro-2-methoxypyridin-3-yl)oxazolidin-2-one

To a solution of (S)-2-amino-2-(5-fluoro-2-methoxypyridin-3-yl)ethanol dihydrochloride (897 mg, 3.46 mmol) in KOH (10 mL, 24.2 mmol, 2.42M in water) was added THF (10 mL). The mixture was cooled to 0° C. and treated with triphosgene (1.03 g, 3.46 mmol). The mixture was allowed to warm to ambient temperature with stirring over 16 hours then partitioned between EtOAc (50 mL) and water (50 mL), and the layers were separated. The aqueous layer was extracted with EtOAc (2×30 mL) and the combined organic phases were washed with brine (20 mL), dried over Na₂SO₄, filtered and concentrated. The residue was triturated with Et₂O, filtered and dried under reduced pressure to afford (S)-4-(5-fluoro-2-methoxypyridin-3-yl)oxazolidin-2-one (254 mg, 35% yield) as a white powder. $^1$H NMR (CDCl₃) δ 7.98 (m, 1H), 7.44 (m, 1H), 5.61 (Br S, 1H), 5.13 (m, 1H), 4.83 (m, 1H), 4.16 (m, 1H), 3.96 (s, 3H).

Step E: Preparation of (S)-ethyl 5-(4-(5-fluoro-2-methoxypyridin-3-yl)-2-oxooxazolidin-3-yl)pyrazolo[1,5-a]pyrimidine-3-carboxylate To a solution of (S)-4-(5-fluoro-2-methoxypyridin-3-yl)oxazolidin-2-one (254 mg, 1.20 mmol) in DMF (10 mL) was added sodium hydride (58 mg, 1.44 mmol, 60% in mineral oil). The mixture was stirred at ambient temperature for 20 minutes then treated with ethyl 5-chloropyrazolo[1,5-a]pyrimidine-3-carboxylate (270 mg, 1.20 mmol) in one portion. The mixture was stirred for 48 hours then treated with saturated NH₄Cl solution (30 mL) and extracted with EtOAc (3×10 mL). The combined organic phases were washed with water (5×10 mL) and brine (10 mL) then dried over Na₂SO₄, filtered and concentrated. The residue was purified by flash column chromatography, eluting with 20% EtOAc/hexanes to 66% EtOAc/hexanes, to afford (S)-ethyl 5-(4-(5-fluoro-2-methoxypyridin-3-yl)-2-oxooxazolidin-3-yl)pyrazolo[1,5-a]pyrimidine-3-carboxylate (311 mg, 65% yield) as a white foam. MS (apci) m/z=401.9 (M+H).

Step F: Preparation of (S)-5-(1-(5-fluoro-2-methoxypyridin-3-yl)-2-hydroxyethylamino)pyrazolo[1,5-a]pyrimidine-3-carboxylic acid To a solution of (S)-ethyl 5-(4-(5-fluoro-2-methoxypyridin-3-yl)-2-oxooxazolidin-3-yl)pyrazolo[1,5-a]pyrimidine-3-carboxylate (311 mg, 0.77 mmol) in a 1:1:1 mixture of MeOH:THF:H₂O (15 mL) was added lithium hydroxide monohydrate (97.6 mg, 2.32 mmol). The mixture was stirred at ambient temperature for 16 hours and then at 50° C. for 19 hours, then concentrated to ⅓ volume, diluted with water (30 mL) and acidified to pH 4-5 with 1N HCl. The resulting precipitate was collected by filtration, washed with water and Et$_2$O, then dried under reduced pressure to afford (S)-5-(1-(5-fluoro-2-methoxypyridin-3-yl)-2-hydroxyethylamino)pyrazolo[1,5-a]pyrimidine-3-carboxylic acid (121 mg, 45% yield) as a white powder. MS (apci) m/z=347.9 (M+H).

Step G: Preparation of (S)—N-(3-chloropropyl)-5-(1-(5-fluoro-2-methoxypyridin-3-yl)-2-hydroxyethylamino)pyrazolo[1,5-a]pyrimidine-3-carboxamide To a suspension of (S)-5-(1-(5-fluoro-2-methoxypyridin-3-yl)-2-hydroxyethylamino)pyrazolo[1,5-a]pyrimidine-3-carboxylic acid (50 mg, 0.14 mmol) in DCM (2 mL) was added HOBt (44 mg, 0.29 mmol) followed by EDCI (83 mg, 0.43 mmol). The heterogeneous mixture was stirred at ambient temperature for 10 minutes then treated with triethylamine (100 µL, 0.72 mmol) followed by 3-chloropropylamine hydrochloride (56 mg, 0.43 mmol). The mixture was stirred for 2 hours, then DMF (2 mL) was added and stirring was continued for 48 hours. The mixture was partitioned between saturated NH$_4$Cl solution (20 mL) and EtOAc (20 mL) and the layers were separated. The aqueous layer was extracted with EtOAc (2×10 mL) and the combined organic phases were washed with water (5×10 mL) and brine (10 mL), then dried over Na$_2$SO$_4$, filtered and concentrated to afford (S)—N-(3-chloropropyl)-5-(1-(5-fluoro-2-methoxypyridin-3-yl)-2-hydroxyethylamino)pyrazolo[1,5-a]pyrimidine-3-carboxamide (60 mg, 99% yield) as a pale yellow foam which was used without further purification. MS (apci) m/z=423.0 (M+H).

Step H: Preparation of (S)—N-(3-chloropropyl)-5-(4-(5-fluoro-2-methoxypyridin-3-yl)-2-oxooxazolidin-3-yl)pyrazolo[1,5-a]pyrimidine-3-carboxamide To a solution of (S)—N-(3-chloropropyl)-5-(1-(5-fluoro-2-methoxypyridin-3-yl)-2-hydroxyethylamino)pyrazolo[1,5-a]pyrimidine-3-carboxamide (60 mg, 0.14 mmol) in ACN (2 mL) was added CDI (35 mg, 0.21 mmol). The solution was stirred at ambient temperature for 16 hours then partitioned between saturated NH$_4$Cl solution (20 mL) and EtOAc (10 mL) and the layers separated. The aqueous layer was extracted with EtOAc (2×10 mL) and the combined organic phases were washed with brine (10 mL), dried over Na$_2$SO$_4$, filtered and concentrated. The residue was purified by flash column chromatography eluting with 1% MeOH-DCM to afford (S)—N-(3-chloropropyl)-5-(4-(5-fluoro-2-methoxypyridin-3-yl)-2-oxooxazolidin-3-yl)pyrazolo[1,5-a]pyrimidine-3-carboxamide (37 mg, 58% yield) as a white solid. MS (apci) m/z=449.0 (M+H).

Step I: Preparation of (S)—N-(3-chloropropyl)-5-(4-(5-fluoro-2-oxo-1,2-dihydropyridin-3-yl)-2-oxooxazolidin-3-yl)pyrazolo[1,5-a]pyrimidine-3-carboxamide A suspension of (S)—N-(3-chloropropyl)-5-(4-(5-fluoro-2-methoxypyridin-3-yl)-2-oxooxazolidin-3-yl)pyrazolo[1,5-a]pyrimidine-3-carboxamide (37 mg, 0.08 mmol) in 4N HCl/dioxane (4 mL) was stirred at 85° C. for 17 hours and then at ambient temperature for 48 hours. The resulting solution was concentrated to ½ volume, transferred to a sealed tube, treated with 4N HCl/dioxane (2 mL) and stirred at 100° C. for 2 hours. The heterogeneous mixture was concentrated, dried under reduced pressure and used directly in the next step, assuming 100% yield. MS (apci) m/z=435.1 (M+H).

Step J: Preparation of (6S)-9-fluoro-4,13-dioxa-2,11,17,21,22,25-hexaazapentacyclo[17.5.2.0$^{2,6}$.0$^{7,12}$.0$^{22,26}$]hexacosa-(25),7(12),8,10,19(26),20,23-heptaene-3,18-dione To a solution of (S)—N-(3-chloropropyl)-5-(4-(5-fluoro-2-oxo-1,2-dihydropyridin-3-yl)-2-oxooxazolidin-3-yl)pyrazolo[1,5-a]pyrimidine-3-carboxamide (35 mg, 0.08 mmol) in DMF (3 mL) was added cesium carbonate (79 mg, 0.24 mmol). The mixture was stirred at 65° C. for 30 minutes then at ambient temperature for 48 hours. The mixture was treated with water (30 mL) and extracted with EtOAc (3×10 mL). The combined organic phases were washed with water (5×10 mL) and brine (10 mL), then dried over Na$_2$SO$_4$, filtered and concentrated. The residue was purified via flash column chromatography eluting with 2% MeOH/DCM to afford the title compound (13 mg, 41% yield) as an amorphous white solid. MS (apci) m/z=399.2 (M+H).

Example 31

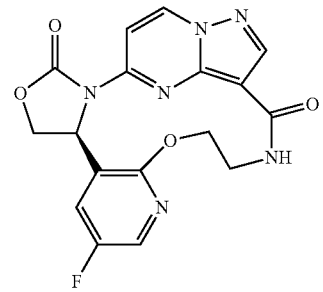 [SMILES: O=C1NCCOc2ncc(F)cc2[C@H]2COC(=O)N2c2ccn3ncc1c3n2]

(6S)-9-fluoro-4,13-dioxa-2,11,16,20,21,24-hexaazapentacyclo[16.5.2.0$^{2,6}$.0$^{7,12}$.0$^{21,25}$]pentacosa-1(24),7(12),8,10,18(25),19,22-heptaene-3,17-dione Step A: Preparation of 5-hydroxypyrazolo[1,5-a]pyrimidine-3-carboxylic acid To a solution of ethyl 5-hydroxypyrazolo[1,5-a]pyrimidine-3-carboxylate (Preparation B, Step A; 2.0 g, 9.65 mmol) in a 2:1 mixture of THF:MeOH, (40 mL) was added lithium hydroxide monohydrate (29 mL, 29.0 mmol, 1.0M in water). The solution was stirred at reflux for 16 hours then cooled and concentrated. The residue was dissolved in water (100 mL) and acidified with 6M HCl. The resulting white precipitate was collected by filtration and washed with water and Et$_2$O, then dried under reduced pressure to afford 5-hydroxypyrazolo[1,5-a]pyrimidine-3-carboxylic acid (1.18 g, 68% yield) as a white solid. $^1$H NMR (d$_6$-DMSO) δ 8.50 (d, 2H, J 7.7 Hz), 8.02 (s, 2H), 6.07 (d, 2H, J=8.2 Hz).

Step B: Preparation of 5-chloropyrazolo[1,5-a]pyrimidine-3-carbonyl chloride

To a suspension of 5-hydroxypyrazolo[1,5-a]pyrimidine-3-carboxylic acid (1.18 g, 6.59 mmol) in DMF (10 mL) at 0° C. was added thionyl chloride (10 mL) dropwise over 5 minutes. The mixture was warmed to ambient temperature, then stirred at 60° C. for 16 hours. The cooled solution was purged with N₂ for 20 minutes then diluted with 50% EtOAc/hexanes (100 mL) and stirred vigorously for 30 minutes. The organic phase was decanted, treated with Na₂CO₃ and activated carbon, stirred for 5 minutes then filtered through Celite® and concentrated. The residue was dissolved in toluene (100 mL), treated with activated carbon and filtered through Celite® again. The filtrate was concentrated and dried under reduced pressure to afford 5-chloropyrazolo[1,5-a]pyrimidine-3-carbonyl chloride (800 mg, 56% yield) as a cream-colored solid. ¹H NMR (CDCl₃) δ 8.70 (m, 1H), 8.66 (s, 1H), 7.16 (m, 1H).

Step C: Preparation of 5-chloro-N-(2-chloroethyl) pyrazolo[1,5-a]pyrimidine-3-carboxamide To a suspension of 5-chloropyrazolo[1,5-a]pyrimidine-3-carbonyl chloride (284 mg, 1.31 mmol) in DCM (10 mL) was added DIEA (1.14 mL, 6.57 mmol). The solution was cooled to 0° C., then treated with 2-chloroethylamine hydrochloride (183 mg, 1.58 mmol) and stirred for 1 hour. The mixture was partitioned between water (30 mL) and DCM (30 mL) and the layers were separated. The aqueous layer was extracted with DCM (2×20 mL) and the combined organic phases were washed with brine (20 mL), dried over Na₂SO₄, filtered and concentrated to afford 5-chloro-N-(2-chloroethyl)pyrazolo[1,5-a]pyrimidine-3-carboxamide (290 mg, 85% yield) as a beige solid. MS (apci) m/z=258.9 (M+H).

Step D: Preparation of (S)—N-(2-chloroethyl)-5-(4-(5-fluoro-2-methoxypyridin-3-yl)-2-oxoxazolidin-3-yl)pyrazolo[1,5-a]pyrimidine-3-carboxamide To a solution of (S)-4-(5-fluoro-2-methoxypyridin-3-yl)oxazolidin-2-one (prepared according to Example 30; 50 mg, 0.236 mmol) in DMF (1 mL) was added sodium hydride (11 mg, 0.28 mmol, 60% in mineral oil). The mixture was stirred at ambient temperature for 20 minutes, then treated with 5-chloro-N-(2-chloroethyl)pyrazolo[1,5-a]pyrimidine-3-carboxamide (61 mg, 0.236 mmol). The mixture was stirred at 16 hours, and then treated with saturated NH₄Cl solution (10 mL) and water (20 mL). The resulting precipitate was collected by filtration, washed with water and Et₂O, then dried under reduced pressure to afford (S)—N-(2-chloroethyl)-5-(4-(5-fluoro-2-methoxypyridin-3-yl)-2-oxoxazolidin-3-yl)pyrazolo[1,5-a]pyrimidine-3-carboxamide (83 mg, 81% yield) as a beige solid. MS (apci) m/z=434.9 (M+H).

Step E: Preparation of (S)—N-(2-chloroethyl)-5-(4-(5-fluoro-2-oxo-1,2-dihydropyridin-3-yl)-2-oxoxazolidin-3-yl)pyrazolo[1,5-a]pyrimidine-3-carboxamide A suspension of (S)—N-(2-chloroethyl)-5-(4-(5-fluoro-2-methoxypyridin-3-yl)-2-oxoxazolidin-3-yl)pyrazolo[1,5-a]pyrimidine-3-carboxamide (80 mg, 0.18 mmol) in 5-6N HCl/IPA (2.5 mL) was warmed to 90° C. in a sealed tube for 1.5 hours. The cooled mixture was filtered and the filtrate was concentrated. The residue was concentrated twice from Et₂O and dried under reduced pressure to afford (S)—N-(2-chloroethyl)-5-(4-(5-fluoro-2-oxo-1,2-dihydropyridin-3-yl)-2-oxoxazolidin-3-yl)pyrazolo[1,5-a]pyrimidine-3-carboxamide (63 mg, 82% yield) as a beige solid. MS (apci) m/z=421.0 (M+H).

Step F: Preparation of (6S)-9-fluoro-4,13-dioxa-2,11,16,20,21,24-hexaazapentacyclo[16.5.2.0²,⁶.0⁷,¹².0²¹,²⁵]pentacosa-(24),7(12),8,10,18(25),19,22-heptaene-3,17-dione Prepared according to the method of Example 30, Step J, using (S)—N-(2-chloroethyl)-5-(4-(5-fluoro-2-oxo-1,2-dihydropyridin-3-yl)-2-oxoxazolidin-3-yl)pyrazolo[1,5-a]pyrimidine-3-carboxamide in place of (S)—N-(3-chloropropyl)-5-(4-(5-fluoro-2-oxo-1,2-dihydropyridin-3-yl)-2-oxoxazolidin-3-yl)pyrazolo[1,5-a]pyrimidine-3-carboxamide to afford the title compound (14 mg, 24% yield) as a white solid. MS (apci) m/z=385.1 (M+H).

Example 32

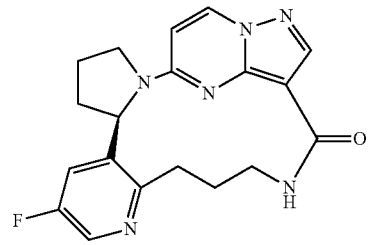 [SMILES: CN1CCCc2ncc(F)cc2[C@H]2CCCN2c2ccn3ncc(c3n2)C1=O]

(6R)-9-fluoro-2,11,16,20,21,24-hexaazapentacyclo[16.5.2.0²,⁶.0⁷,¹².0²¹,²⁵]pentacosa-1(24),7,9,11,18(25),19,22-heptaen-17-one Step A: Preparation of (R)-ethyl 5-(2-(2-(3-((tert-butoxycarbonyl)amino)prop-1-yn-1-yl)-5-fluoropyridin-3-yl)pyrrolidin-1-yl)pyrazolo[1,5-a]pyrimidine-3-carboxylate (R)-ethyl 5-(2-(2-chloro-5-fluoropyridin-3-yl)pyrrolidin-1-yl)pyrazolo[1,5-a]pyrimidine-3-carboxylate (Example 12, Step C; 153 mg, 0.392 mmol) in DMF (2 mL) was added tert-butyl prop-2-ynylcarbamate (122 mg, 0.785 mmol), copper(I) iodide (11 mg, 0.0578 mmol), triphenylphosphine (82.4 mg, 0.314 mmol), di-triphenylphosphine palladium(II) chloride (116 mg, 0.165 mmol), and diisopropylamine (99.3 mg, 0.981 mmol). The reaction mixture was sealed and heated to 95° C. for 8 hours, then cooled to ambient temperature and concentrated under reduced pressure The residue was purified by silica column chromatography, eluting with 33% EtOAc/Hexanes to afford the final product mixed with Ph₃P (160 mg, 80.2% yield). MS (apci) m/z=508.9 (M+H).

Step B: Preparation of (R)-ethyl 5-(2-(2-(3-aminopropyl)-5-fluoropyridin-3-yl)pyrrolidin-1-yl)pyrazolo[1,5-a]pyrimidine-3-carboxylate To (R)-ethyl 5-(2-(2-(3-(tert-butoxycarbonylamino)prop-1-ynyl)-5-fluoropyridin-3-yl)pyrrolidin-1-yl)pyrazolo[1,5-a]pyrimidine-3-carboxylate (160 mg, 0.315 mmol) in MeOH (10 mL) was added dihydroxypalladium (101 mg, 0.144 mmol). The reaction mixture was stirred under a hydrogen balloon for 6 hours, then filtered through a pad of Celite® and washed with MeOH (30 mL). The filtrate was concentrated and the resultant residue was treated with 4M HCl in dioxane (3 mL). After stirring for 30 minutes, the solution was concentrated to afford the product as an HCl salt (140 mg, 108% yield). MS (apci) m/z=413.0 (M+H).

Step C: Preparation of (R)-5-(2-(2-(3-aminopropyl)-5-fluoropyridin-3-yl)pyrrolidin-1-yl)pyrazolo[1,5-a]pyrimidine-3-carboxylic acid To (R)-ethyl 5-(2-(2-(3-aminopropyl)-5-fluoropyridin-3-yl)pyrrolidin-1-yl)pyrazolo[1,5-a]pyrimidine-3-carboxylate hydrochloride (160 mg, 0.356 mmol) in THF/MeOH (2 mL/1 mL) was added lithium hydroxide (1.1 mL, 2.20 mmol). The reaction mixture was heated to 70° C. for 5 hours, then concentrated under reduced pressure. Water (10 mL) was added and the mixture washed with Et$_2$O (2×5 mL), then neutralized with HCl (1M) to pH=4. The aqueous solution was extracted with DCM (2×10 mL). The organic extract was dried with Na$_2$SO$_4$, filtered and concentrated under reduced pressure to give the crude desired product (16.0 mg, 11.7% yield). MS (apci) m/z=385.0 (M+H).

Step D: Preparation of (6R)-9-fluoro-2,11,16,20,21,24-hexaazapentacyclo[16.5.2.0$^{2,6}$.0$^{7,12}$.0$^{21,25}$]pentacosa-1(24),7,9,11,18(25),19,22-heptaen-17-one To (R)-5-(2-(2-(3-aminopropyl)-5-fluoropyridin-3-yl)pyrrolidin-1-yl)pyrazolo[1,5-a]pyrimidine-3-carboxylic acid (16 mg, 0.042 mmol) in DMF (5 mL) was added HATU (63 mg, 0.17 mmol) and N-ethyl-N-isopropylpropan-2-amine (22 mg, 0.17 mmol). The reaction mixture was stirred for 3 hours and concentrated under reduced pressure. The crude residue was purified by silica column chromatography using 100% EtOAc to afford the title compound (6.0 mg, 39% yield). MS (apci) m/z=367.3 (M+H).

Example 33

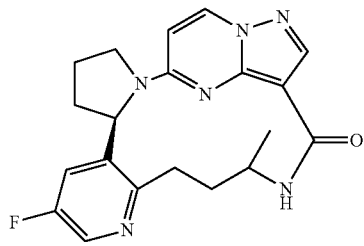 [SMILES: CC1CCc2ncc(F)cc2[C@H]2CCCN2c2ccn3ncc(c3n2)C(=O)N1C]

(6R)-9-fluoro-15-methyl-2,11,16,20,21,24-hexaazapentacyclo[16.5.2.0$^{2,6}$.0$^{7,12}$.0$^{21,25}$]pentacosa-1(24),7,9,11,18(25), 19,22-heptaen-17-one Prepared according to the method of Example 37, substituting tert-butyl 2-methylbut-3-yn-2-ylcarbamate with tert-butyl but-3-yn-2-ylcarbamate in Step B to afford the title compound as a 1:1 mixture of diastereomers. MS (apci) m/z=381.2 (M+H).

Example 34

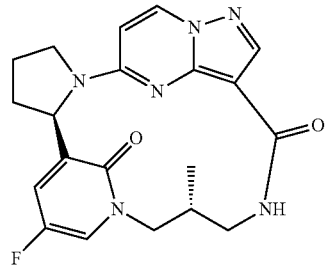 [SMILES: C[C@@H]1CNC(=O)c2cnn3ccc(nc23)N2CCC[C@@H]2c2cc(F)cn(c2=O)C1]

(6R,13R)-9-fluoro-13-methyl-2,11,15,19,20,23-hexaazapentacyclo[15.5.2.1$^{7,11}$.0$^{2,6}$.0$^{20,24}$]pentacosa-1(23),7,9,17(24),18,21-hexaene-16,25-dione Step A: Preparation of (R)-methyl 5-(2-(5-fluoro-2-hydroxypyridin-3-yl)pyrrolidin-1-yl)pyrazolo[1,5-a]pyrimidine-3-carboxylate To a suspension of (R)-5-(2-(5-fluoro-2-methoxypyridin-3-yl)pyrrolidin-1-yl)pyrazolo[1,5-a]pyrimidine-3-carboxylic acid (Preparation B; 5.01 g, 14.0 mmol) in MeOH (150 mL) was added dropwise TMSCHN$_2$ (8.41 mL, 16.8 mmol). The reaction was stirred for 30 minutes, and then quenched with 1 mL of acetic acid. The solvent was removed under reduced pressure and the residue was dried under high vacuum to give the crude methyl ester. To the crude methyl ester was added 4N HCl in dioxane (100 mL) and the reaction was sealed and heated to 90° C. for 2 hours. The reaction mixture was concentrated under reduced pressure and the residue was dissolved in DCM (100 mL) and washed with saturated NaHCO$_3$ (40 mL). The organic layer was dried over Na$_2$SO$_4$, filtered and concentrated under reduced pressure to give the crude desired product (4.67 g, 93.2% yield). MS (apci) m/z=357.9 (M+H).

Step B: Preparation of methyl 5-((R)-2-(1-((S)-3-(1,3-dioxoisoindolin-2-yl)-2-methylpropyl)-5-fluoro-2-oxo-1,2-dihydropyridin-3-yl)pyrrolidin-1-yl)pyrazolo[1,5-a]pyrimidine-3-carboxylate To a solution of (R)-methyl 5-(2-(5-fluoro-2-hydroxypyridin-3-yl)pyrrolidin-1-yl)pyrazolo[1,5-a]pyrimidine-3-carboxylate (202 mg, 0.565 mmol) in DMF (5 mL) was added lithium hydride (22.5 mg, 2.83 mmol) and (R)-2-(3-bromo-2-methylpropyl)isoindoline-1,3-dione (prepared according to the procedure described in Euro. J. Med. Chem. 2000, 147-156) (239 mg, 0.848 mmol). The reaction was stirred for 2 hours at 70° C., and then cooled to ambient temperature. The reaction mixture was diluted with EtOAc (20 mL) and washed with water (2×10 mL). The organic layer was dried with Na$_2$SO$_4$, filtered and concentrated under reduced pressure. The residue was purified by silica column chromatography, eluting with 66% EtOAc/Hexanes to afford the product (110 mg, 34.8% yield). MS (apci) m/z=559.0 (M+H).

Step C: Preparation of methyl 5-((R)-2-(1-((R)-3-amino-2-methylpropyl-5-fluoro-2-oxo-1,2-dihydropyridin-3-yl)pyrrolidin-1-yl)pyrazolo[1,5-a]pyrimidine-3-carboxylate To a solution of methyl 5-((R)-2-(1-((S)-3-(1,3-dioxoisoindolin-2-yl)-2-methylpropyl)-5-fluoro-2-oxo-1,2-dihydropyridin-3-yl)pyrrolidin-1-yl)pyrazolo[1,5-a]pyrimidine-3-carboxylate (110 mg, 0.197 mmol) in MeOH/THF (3 mL/3 mL) was added hydrazine (31.6 mg, 0.985 mmol). The reaction was stirred for 14 hours at 50° C. After cooling, the reaction mixture was concentrated and the resulting residue was diluted with EtOAc (20 mL) and washed with saturated aqueous NaHCO$_3$ (5 mL), water (2×5 mL) and brine (5 mL). The organic layer was dried with Na$_2$SO$_4$, filtered and concentrated under reduced pressure. The residue was purified by silica column chromatography, eluting with EtOAc/MeOH/NH$_4$OH 10:1:0.1 to give the desired product (65 mg, 77% yield). MS (apci) m/z=429.2 (M+H).

Step D: Preparation of (6R,13R)-9-fluoro-13-methyl-2,11,15,19,20,23-hexaazapentacyclo [15.5.2.1$^{7,11}$.0$^{2,6}$.0$^{20,24}$]pentacosa-1(23),7,9,17(24),18,21-hexaene-16,25-dione To a solution of methyl 5-((R)-2-(1-((R)-3-amino-2-methylpropyl)-5-fluoro-2-oxo-1,2-dihydropyridin-3-yl)pyrrolidin-1-yl)pyrazolo[1,5-a]pyrimidine-3-carboxylate (65 mg, 0.15 mmol) in THF/MeOH (6 mL/2 mL) was added lithium hydroxide (455 µL, 0.91 mmol). The reaction was stirred at 70° C. for 3 hours, then quenched with hydrogen chloride (910 µL, 0.91 mmol). The solvent was removed under reduced pressure and the residue was dried under high vacuum. To the resulting crude residue was added DMF (10 mL), HATU (115 mg, 0.30 mmol) and N-ethyl-N-isopropylpropan-2-amine (78 mg, 0.61 mmol). The reaction was stirred for 3 hours, and the solvent was removed under reduced pressure. The residue was purified by silica column chromatography, eluting with 10% MeOH/EtOAc to afford the title compound (6.0 mg, 10% yield). MS (apci) m/z=397.3 (M+H).

Example 35

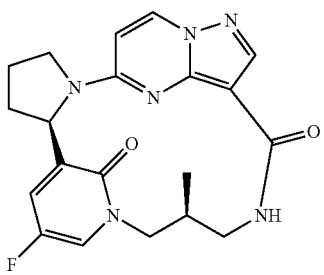 [SMILES: C[C@H]1CNC(=O)c2cnn3ccc(nc23)N2CCC[C@@H]2c2cc(F)cn(c2=O)C1]

(6R,13S)-9-fluoro-13-methyl-2,11,15,19,20,23-hexaazapentacyclo[15.5.2.1$^{7,11}$.0$^{2,6}$.0$^{20,24}$]pentacosa-1(23),7,9,17(24),18,21-hexaene-16,25-dione Prepared according to the method of Example 34, substituting (S)-2-(3-bromo-2-methylpropyl)isoindoline-1,3-dione (prepared according to the procedure described in Euro. J. Med. Chem. 2000, 147-156) for (R)-2-(3-bromo-2-methylpropyl)isoindoline-1,3-dione in Step B. MS (apci) m/z=397.3 (M+H).

Example 36

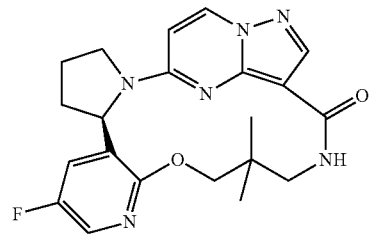 [SMILES: CC1(C)CNC(=O)c2cnn3ccc(nc23)N2CCC[C@@H]2c2cc(F)cnc2OC1]

(6R)-9-fluoro-15,15-dimethyl-13-oxa-2,11,17,21,22,25-hexaazapentacyclo[17.5.2.0$^{2,6}$.0$^{7,12}$.0$^{22,26}$]hexacosa-1(25),7,9,11,19(26),20,23-heptaen-18-one Prepared according to the procedure for Example 3, substituting 3-amino-2,2-dimethylpropan-1-ol for 3-aminopropan-1-ol in Step A. MS (apci) m/z=411.2 (M+H).

Example 37

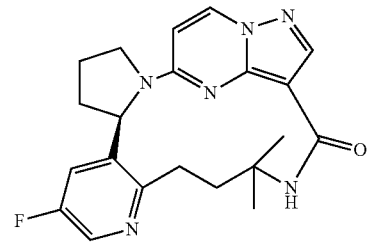 [SMILES: CN1C(=O)c2cnn3ccc(nc23)N2CCC[C@@H]2c2cc(F)cnc2CCC1(C)C]

(6R)-9-fluoro-15,15-dimethyl-2,11,16,20,21,24-hexaazapentacyclo[16.5.2.0$^{2,6}$.0$^{7,12}$.0$^{21,25}$]pentacosa-1(24),7,9,11,18(25),19,22-heptaen-17-one Step A: Preparation of (R)-methyl 5-(2-(5-fluoro-2-(trifluoromethyl-sulfonyloxy)pyridin-3-yl)pyrrolidin-1-yl)pyrazolo[1,5-a]pyrimidine-3-carboxylate To a solution of (R)-methyl 5-(2-(5-fluoro-2-hydroxypyridin-3-yl)pyrrolidin-1-yl)pyrazolo[1,5-a]pyrimidine-3-carboxylate (Prepared according to Example 34, Step A; 2.31 g, 6.46 mmol) in DMF (20 mL) was added 1,1,1-trifluoro-N-phenyl-N-(trifluoromethyl-sulfonyl)methanesulfonamide (2.54 g, 7.11 mmol) and triethylamine (0.785 g, 7.76 mmol). The reaction was stirred for 18 hours. The solvent was removed under reduced pressure and the residue was purified by silica column chromatography, eluting with 33% EtOAc/Hexanes to afford the desired product (2.36 g, 74.6% yield). MS (apci) m/z=490.0 (M+H).

Step B: Preparation of (R)-methyl 5-(2-(2-(3-(tert-butoxycarbonylamino)-3-methylbutyl)-5-fluoropyridin-3-yl)pyrrolidin-1-yl)pyrazolo[1,5-a]pyrimidine-3-carboxylate To (R)-methyl 5-(2-(5-fluoro-2-(trifluoromethylsulfonyloxy)pyridin-3-yl)pyrrolidin-1-yl)pyrazolo[1,5-a]pyrimidine-3-carboxylate (503 mg, 1.03 mmol) in DMF (2 mL)

was added tert-butyl 2-methylbut-3-yn-2-ylcarbamate (377 mg, 2.06 mmol), copper(I) iodide (39.1 mg, 0.206 mmol), di-triphenylphosphine palladium(II) chloride (144 mg, 0.206 mmol), diisopropylamine (260 mg, 2.57 mmol). The reaction mixture was sealed and heated to 65 OC for 8 hours. The solvent was removed under reduced pressure. The residue was purified by silica column chromatography, eluting with 66% EtOAc/Hexanes to give (R)-methyl 5-(2-(2-(3-(tert-butoxycarbonylamino)-3-methylbut-1-ynyl)-5-fluoropyridin-3-yl)pyrrolidin-1-yl)pyrazolo[1,5-a]pyrimidine-3-carboxylate mixed with $Ph_3P$, which was immediately hydrogenated using dihydroxypalladium on carbon (200 mg, 0.285 mmol) in MeOH (20 mL) under a $H_2$ balloon for 15 hours. After filtering through a pad of Celite® and washing with MeOH, the filtrate was concentrated under reduced pressure and purified by silica column chromatography, eluting with 66% EtOAc/Hexanes to afford the product (166 mg, 30.7% yield). MS (apci) m/z=527.1 (M+H).

Step C: Preparation of (6R)-9-fluoro-15,15-dimethyl-2,11,16,20,21,24-hexaazapentacyclo[16.5.2.$0^{2,6}.0^{7,12}.0^{21,25}$]pentacosa-1(24),7,9,11,18(25),19,22-heptaen-17-one To (R)-methyl 5-(2-(2-(3-(tert-butoxycarbonylamino)-3-methylbutyl)-5-fluoropyridin-3-yl)pyrrolidin-1-yl)pyrazolo[1,5-a]pyrimidine-3-carboxylate (166 mg, 0.315 mmol) in THF/MeOH (3 mL/1 mL) was added lithium hydroxide (946 µL, 1.89 mmol). The reaction vessel was sealed and heated to 70° C. for 3 hours. The reaction mixture was then dried under reduced pressure and HCl (4 mL, 4M in dioxane) was added. The reaction mixture was stirred for one hour, then the solvent was removed and the residue was dried under high vacuum for two hours. To the residue was then added DMF (8 mL), HOBT-$H_2O$ (96.5 mg, 0.630 mmol), EDCI (121 mg, 0.630 mmol) and triethylamine (159 mg, 1.58 mmol). The reaction mixture was stirred at 45° C. for 18 hours, then concentrated under vacuum The residue was purified by silica column chromatography eluting with 5% MeOH/DCM to afford the title compound (60.0 mg, 48.3% yield). MS (apci) m/z=395.1 (M+H).

Example 38

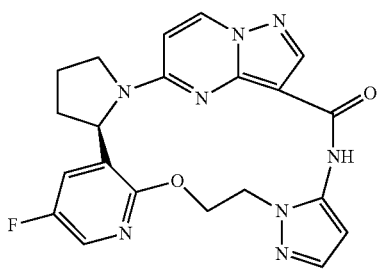 [SMILES: O=C1Nc2ccnn2CCOc2ncc(F)cc2[C@H]2CCCN2c2ccn3ncc1c3n2]

(6R)-9-fluoro-13-oxa-2,11,16,17,21,25,26,29-octaazahexacyclo[21.5.2.$0^{2,6}.0^{7,12}.0^{16,20}.0^{26,30}$]triaconta-1(29),7,9,11,17,19,23(30),24,27-nonaen-22-one Step A: Preparation of 1-(2-(tert-butyldiphenylsilyloxy)ethyl)-1H-pyrazol-5-amine To a suspension of 2-(5-amino-1H-pyrazol-1-yl)ethanol (2.07 g, 16.0 mmol) and 1H-imidazole (5.43 g, 79.8 mmol) in DMF (10 mL) was added dropwise tert-butylchlorodiphenylsilane (4.96 mL, 19.1 mmol). The reaction was stirred for 15 hours. The solvent was removed under reduced pressure and the residue was diluted with DCM (40 mL). The organic layer was washed with 1N HCl (10 mL), water (10 mL) and brine (10 mL), then concentrated to give crude desired product (5.62 g, 96.4% yield), which was used in the next step without purification.

Step B: Preparation of (R)—N-(1-(2-(tert-butyldiphenylsilyloxy)ethyl)-1H-pyrazol-5-yl)-5-(2-(5-fluoro-2-methoxypyridin-3-yl)pyrrolidin-1-yl)pyrazolo[1,5-a]pyrimidine-3-carboxamide To a suspension of (R)-5-(2-(5-fluoro-2-methoxypyridin-3-yl)pyrrolidin-1-yl)pyrazolo[1,5-a]pyrimidine-3-carboxylic acid (220 mg, 0.616 mmol) in DMF (5 mL) was added dropwise 2,4,6-trichlorobenzoyl chloride (106 µL, 0.677 mmol) and triethylamine (81.0 mg, 0.800 mmol). The reaction was stirred for 2 hours, and 1-(2-(tert-butyldiphenylsilyloxy)ethyl)-1H-pyrazol-5-amine (338 mg, 0.923 mmol) was added to the reaction mixture. The reaction was heated to 60° C. for 3 hours and then cooled to ambient temperature. The solvent was removed under reduced pressure and the residue was purified by silica column chromatography to afford the desired product (201 mg, 46.3% yield). MS (apci) m/z=705.1 (M+H).

Step C: Preparation of (6R)-9-fluoro-13-oxa-2,11,16,17,21,25,26,29-octaazahexacyclo[21.5.2.$0^{2,6}.0^{7,12}.0^{16,20}.0^{26,30}$]triaconta-1 (29),7,9,11,17,19,23(30),24,27-nonaen-22-one A suspension of (R)—N-(1-(2-(tert-butyldiphenylsilyloxy)ethyl)-1H-pyrazol-5-yl)-5-(2-(5-fluoro-2-methoxypyridin-3-yl)pyrrolidin-1-yl)pyrazolo[1,5-a]pyrimidine-3-carboxamide (201 mg, 0.285 mmol) in 4M HCl in dioxane (6 mL) was sealed and heated to 100° C. for fours hours. The reaction mixture was cooled to ambient temperature and concentrated under reduced pressure. The residue was diluted with DCM (20 mL) and washed with saturated $NaHCO_3$ (5 mL), water (5 mL) and brine (5 mL). The organic layer was concentrated to give crude (R)-5-(2-(5-fluoro-2-hydroxypyridin-3-yl)pyrrolidin-1-yl)-N-(1-(2-hydroxyethyl)-1H-pyrazol-5-yl)pyrazolo[1,5-a]pyrimidine-3-carboxamide, to which was added THF (20 mL), DEAD (53.9 µL, 0.342 mmol) and triphenylphosphine (89.8 mg, 0.342 mmol). The reaction mixture was stirred for 18 hours, then concentrated under vacuum. The residue was purified by silica column chromatography, eluting with 10% MeOH/DCM to afford the title compound (1.8 mg, 1.5% yield). MS (apci) m/z=435.3 (M+H).

Example 39

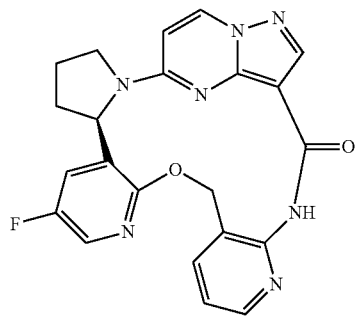 [SMILES: O=C1Nc2ncccc2COc2ncc(F)cc2[C@H]2CCCN2c2ccn3ncc1c3n2]

(6R)-9-fluoro-13-oxa-2,11,19,21,25,26,29-heptaaza-hexacyclo[21.5.2.0$^{2,6}$.0$^{7,12}$.0$^{15,20}$.0$^{26,30}$]triaconta-1(29),7,9,11,15(20),16,18,23(30),24,27-decaen-22-one Step A: Preparation of 3-((tert-butyldiphenylsilyloxy)methyl)pyridin-2-amine To a suspension of (2-aminopyridin-3-yl)methanol (2.19 g, 17.6 mmol) and 1H-imidazole (6.00 g, 88.2 mmol) in DMF (10 mL) was added dropwise tert-butylchlorodiphenylsilane (5.49 mL, 21.2 mmol). The reaction was stirred for 15 hours. The solvent was removed under reduced pressure and the residue was diluted with DCM (40 mL). The organic layer was washed with 1N HCl (10 mL), water (10 mL) and brine (10 mL) and then concentrated to give crude product (6.03 g, 94.3% yield). MS (apci) m/z=363.1 (M+H).

Step B: Preparation of (6R)-9-fluoro-13-oxa-2,11,19,21,25,26,29-heptaazahexacyclo[21.5.2.0$^{2,6}$.0$^{7,12}$.0$^{15,20}$.0$^{26,30}$]triaconta-1(29),7,9,11,15(20),16,18,23(30),24,27-decaen-22-one To a suspension of (R)-5-(2-(5-fluoro-2-methoxypyridin-3-yl)pyrrolidin-1-yl)pyrazolo[1,5-a]pyrimidine-3-carboxylic acid (303 mg, 0.848 mmol) in DMF (5 mL) was added triethylamine (103 mg, 1.02 mmol), followed by dropwise addition of 2,4,6-trichlorobenzoyl chloride (227 mg, 0.933 mmol). The reaction was stirred for two hours. 3-((tert-Butyldiphenylsilyloxy)methyl)pyridin-2-amine (369 mg, 1.02 mmol) was added and the reaction mixture was heated to 60° C. for 5 hours. The solvent was removed under reduced pressure and the residue was purified by silica column chromatography, eluting with 10% MeOH/DCM to give (R)—N-(3-((tert-butyldiphenylsilyloxy)methyl)pyridin-2-yl)-5-(2-(5-fluoro-2-methoxypyridin-3-yl)pyrrolidin-1-yl)pyrazolo[1,5-a]pyrimidine-3-carboxamide, to which was added THF (5 mL) and TBAF (848 µL, 0.848 mmol). The reaction mixture was stirred for one hour, then quenched with saturated NH$_4$Cl (1 mL) and then concentrated under reduced pressure to give crude (R)-5-(2-(5-fluoro-2-methoxypyridin-3-yl)pyrrolidin-1-yl)-N-(3-(hydroxymethyl)pyridin-2-yl)pyrazolo[1,5-a]pyrimidine-3-carboxamide, to which was added HCl (4M in dioxane, 5 mL). The reaction mixture was sealed and heated to 100° C. for four hours. The reaction mixture was cooled to ambient temperature and concentrated under reduced pressure. The residue was diluted with DCM (20 mL) and the organic layer was washed with saturated NaHCO$_3$ (5 mL), water (5 mL) and brine (5 mL). The organic layer was concentrated under reduced pressure to give crude (R)—N-(3-(chloromethyl)pyridin-2-yl)-5-(2-(5-fluoro-2-hydroxypyridin-3-yl)pyrrolidin-1-yl)pyrazolo[1,5-a]pyrimidine-3-carboxamide, to which was added DMF (10 mL) and Cs$_2$CO$_3$ (276 mg, 0.848 mmol). The reaction mixture was heated to 60° C. for 4 hours, then cooled to ambient temperature and concentrated under reduced pressure. The residue was purified by silica column chromatography, eluting with 10% MeOH/DCM to afford the title compound (8.0 mg, 2.2% yield). MS (apci) m/z=432.3 (M+H).

Example 40

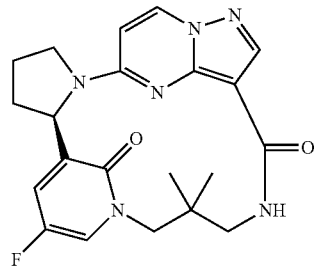 [SMILES: CC1(C)CNC(=O)c2cnn3ccc(nc23)N2CCC[C@@H]2c2cc(F)cn(c2=O)C1]

(6R)-9-fluoro-13,13-dimethyl-2,11,15,19,20,23-hexaazapentacyclo[15.5.2.1$^{7,11}$.0$^{2,6}$.0$^{20,24}$]pentacosa-1(23),7,9,17(24),18,21-hexaene-16,25-dione Step A: Preparation of 3-bromo-2,2-dimethylpropan-1-amine hydrobromide A mixture of 2-(3-bromo-2,2-dimethylpropyl)isoindoline-1,3-dione (1.00 g, 3.38 mmol) in 48% aqueous HBr (10 mL) was refluxed for 18 hours. The reaction mixture was cooled to ambient temperature and the solids formed were filtered off. The filtrate was concentrated under reduced pressure to give the crude material that was azeotroped with toluene (3×) followed by acetonitrile until solids formed. The crude material was triturated with ether and dried under reduced pressure to afford 3-bromo-2,2-dimethylpropan-1-amine hydrobromide (0.816 g, 3.07 mmol, 91.0% yield) (confirmed by $^1$H-NMR and posAPCI-MS). The isolated product was used directly without further purification.

Step B: Preparation of (R)—N-(3-bromo-2,2-dimethylpropyl)-5-(2-(5-fluoro-2-hydroxypyridin-3-yl)pyrrolidin-1-yl)pyrazolo[1,5-a]pyrimidine-3-carboxamide To a solution of (R)-5-(2-(5-fluoro-2-methoxypyridin-3-yl)pyrrolidin-1-yl)pyrazolo[1,5-a]pyrimidine-3-carboxylic acid (Preparation B; 150 mg, 0.420 mmol), EDCI (88.5 mg, 0.462 mmol), and HOBT-H$_2$O (70.7 mg, 0.462 mmol) in DMF (10 mL) was added 3-bromo-2,2-dimethylpropan-1-amine hydrobromide (124 mg, 0.504 mmol) followed by triethylamine (55.2 mg, 0.546 mmol). The reaction was stirred for 18 hours. The solvent was removed under reduced pressure and the residue was purified by silica column chromatography, eluting with 50% EtOAc/Hexanes to provide (R)—N-(3-bromo-2,2-dimethylpropyl)-5-(2-(5-fluoro-2-methoxypyridin-3-yl)pyrrolidin-1-yl)pyrazolo[1,5-a]pyrimidine-3-carboxamide (180 mg), to which was added HCl (5 mL, 4M in dioxane). The reaction was sealed and heated to 90° C. for 2 hours. The solvent was removed under reduced pressure and the residue was purified by silica column chromatography, eluting with 20% Hexanes/EtOAc to provide the desired product (130 mg, 63% yield).

Step C: Preparation of (6R)-9-fluoro-13,13-dimethyl-2,11,15,19,20,23-hexaazapentacyclo[15.5.2.1$^{7,11}$.0$^{2,6}$.0$^{20,24}$]pentacosa-1(23),7,9,17(24),18,21-hexaene-16,25-dione To a solution of (R)—N-(3-bromo-2,2-dimethylpropyl)-5-(2-(5-fluoro-2-hydroxypyridin-3-yl)pyrrolidin-1-yl)pyrazolo[1,5-a]pyrimidine-3-carboxamide (30 mg, 0.061 mmol) in THF (5 mL) was added drop-wise potassium 2-methylpropan-2-olate (153 μL, 0.15 mmol). The reaction was heated at 50° C. for two hours. The solvent was removed under reduced pressure and the residue was purified by silica column chromatography, eluting with 10% MeOH/DCM to provide the title compound (15 mg, 60% yield). MS (apci) m/z=411.0 (M+H).

Example 41

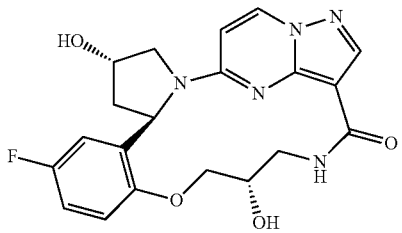 [SMILES: O=C1NC[C@H](O)COc2ccc(F)cc2[C@H]2C[C@H](O)CN2c2ccn3ncc1c3n2]

(4R,6R,15S)-9-fluoro-4,15-dihydroxy-13-oxa-2,17,21,22,25-pentaazapentacyclo[17.5.2.0$^{2,6}$.0$^{7,12}$.0$^{22,26}$]hexacosa-1(25),7(12),8,10,19(26),20,23-heptaen-18-one Step A: Preparation of N—((S)-3-chloro-2-hydroxypropyl)-5-((R)-2-(5-fluoro-2-hydroxyphenyl)-4-hydroxypyrrolidin-1-yl)pyrazolo[1,5-a]pyrimidine-3-carboxamide To a suspension of (R)-5-(2-(5-fluoro-2-hydroxyphenyl)-4-hydroxypyrrolidin-1-yl)pyrazolo[1,5-a]pyrimidine-3-carboxylic acid (Preparation D; 0.0339 g, 0.0946 mmol) and HATU (0.0540 g, 0.142 mmol) in DMF (0.5 mL) at 0° C. was added (S)-1-amino-3-chloropropan-2-ol hydrochloride (Example 19, Step A; 0.0155 g, 0.142 mmol; prepared according to the method described in Org. Process Res. Dev. 2003, vol. 7, p. 533) and N,N-diisopropylethylamine (0.0494 mL, 0.284 mmol). The resulting mixture was warmed to ambient temperature and stirred for 18 hours. The reaction mixture was diluted with EtOAc (10 mL), washed with brine, dried over MgSO$_4$, filtered, and concentrated under reduced pressure to give the crude material which was purified by silica column chromatography, eluting with 0-20% MeOH/DCM to afford N—((S)-3-chloro-2-hydroxypropyl)-5-((R)-2-(5-fluoro-2-hydroxyphenyl)-4-hydroxypyrrolidin-1-yl)pyrazolo[1,5-a]pyrimidine-3-carboxamide (as a mixture of cis and trans isomers, 0.0407 g, 82.2% yield, 86% purity). LC/MS (ES+APCI) m/z=448.1 (M−H).

Step B: Preparation of (4R,6R,15S)-9-fluoro-4,15-dihydroxy-13-oxa-2,17,21,22,25-pentaazapentacyclo[17.5.2.0$^{2,6}$.0$^{7,12}$.0$^{22,26}$]hexacosa-1 (25),7(12),8,10,19(26),20,23-heptaen-18-one A mixture of N—((S)-3-chloro-2-hydroxypropyl)-5-((R)-2-(5-fluoro-2-hydroxyphenyl)-4-hydroxypyrrolidin-1-yl)pyrazolo[1,5-a]pyrimidine-3-carboxamide (0.0407 g, 0.0778 mmol) and Cs$_2$CO$_3$ (0.127 g, 0.389 mmol) in DMF (3.6 mL) was heated at 85° C. for 30 minutes. The reaction mixture was cooled to ambient temperature and filtered. The filtrate was concentrated under reduced pressure to give the crude material which was purified by silica column chromatography, eluting with 0-20% MeOH/EtOAc to afford the crude product. The crude material was purified using chiral column chromatography (Chiral Tech OD-H column, 20% EtOH in hexanes). Isolation of the material having a retention time of about 21.8 minutes afforded the title compound (0.0052 g, 16.2% yield). The stereochemistry of the title compound was confirmed by $^1$H-NMR nOe experiment. LC/MS (ES+APCI) m/z=414.1 (M+H).

Example 41-B

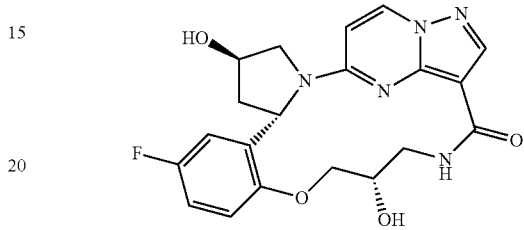

(4R,6S,15S)-9-fluoro-4,15-dihydroxy-13-oxa-2,17,21,22,25-pentaazapentacyclo[17.5.2.0$^{2,6}$.0$^{7,12}$.0$^{22,26}$]hexacosa-1(25),7(12),8,10,19(26),20,23-heptaen-18-one The title compound was isolated during chiral separation reported in Example 41 from fractions having a retention time of about 30.6 minutes, to provide 5.4 mg (16.8% yield) of the compound which may have been isolated along with the enantiomer and/or one or more diastereomers. The stereochemistry of the title compound was confirmed by $^1$H-NMR nOe experiment), LC/MS (ES+APCI) m/z=414.1 (M+H).

Example 42

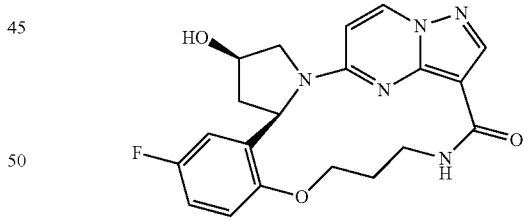

(4R,6R)-9-fluoro-4-hydroxy-13-oxa-2,17,21,22,25-pentaazapentacyclo[17.5.2.0$^{2,6}$.0$^{7,12}$.0$^{22,26}$]hexacosa-1 (25),7(12),8,10,19(26),20,23-heptaen-18-one The title compound was prepared according to the method of Example 41, substituting 3-chloropropan-1-amine hydrochloride for (S)-1-amino-3-chloropropan-2-ol hydrochloride in Step A: 13.8 mg (16% yield; Chiral Tech OD-H column, 20% EtOH in hexanes, retention time about 17.2 minutes). The stereochemistry of the title compound was confirmed by $^1$H-NMR nOe experiment. LC/MS (ES+APCI) m/z=398.1 (M−H).

Example 42-B

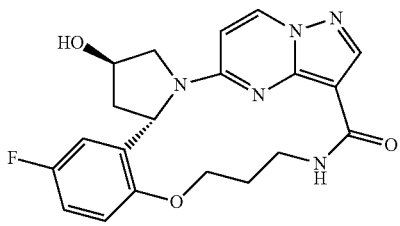 [SMILES: O=C1NCCCOc2ccc(F)cc2[C@@H]2C[C@@H](O)CN2c2ccn3ncc1c3n2]

(4R,6S)-9-fluoro-4-hydroxy-13-oxa-2,17,21,22,25-pentaazapentacyclo[17.5.2.0$^{2,6}$.0$^{7,12}$.0$^{22,26}$]hexacosa-1(25),7(12),8,10,19(26),20,23-heptaen-18-one The title compound was prepared during the chiral separation reported in Example 42 by isolating the fractions having retention time about 26.2 minutes (21.1 mg, 24.5% yield) which may have been isolated along with enantiomer and/or one or more diastereomers. The stereochemistry of the title compound was confirmed by $^1$H-NMR nOe experiment. LC/MS (ES+APCI) m/z=398.1 (M+H).

Example 43

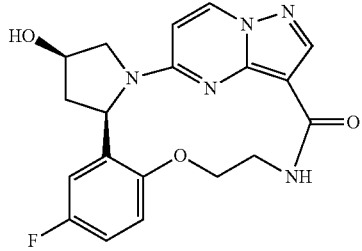 [SMILES: O=C1NCCOc2ccc(F)cc2[C@H]2C[C@@H](O)CN2c2ccn3ncc1c3n2]

(4R,6R)-9-fluoro-4-hydroxy-13-oxa-2,16,20,21,24-pentaazapentacyclo[16.5.2.0$^{2,6}$.0$^{7,12}$.0$^{21,25}$]pentacosa-1(24),7,9,11,18(25),19,22-heptaen-17-one The title compound was prepared according to the method of Example 41, substituting 2-chloroethylamine hydrochloride for (S)-1-amino-3-chloropropan-2-ol hydrochloride in Step A. The title compound was purified using a Chiral Tech OJ-H column, 20% EtOH in hexanes, by isolating fractions having a retention time of about 15.7 minutes (10.7 mg, 14.2% yield). The stereochemistry of the title compound was confirmed by $^1$H-NMR nOe experiment. LC/MS (ES+APCI) m/z=384.1 (M+H).

Example 43-B

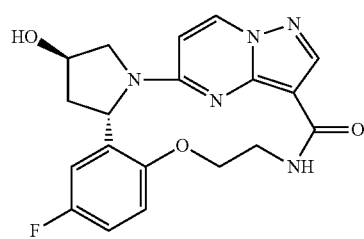 [SMILES: O=C1NCCOc2ccc(F)cc2[C@@H]2C[C@@H](O)CN2c2ccn3ncc1c3n2]

(4R,6S)-9-fluoro-4-hydroxy-13-oxa-2,16,20,21,24-pentaazapentacyclo[16.5.2.0$^{2,6}$.0$^{7,12}$.0$^{21,25}$]pentacosa-1(24),7,9,11,18(25),19,22-heptaen-17-one The title compound was isolated during the chiral separation reported in Example 43 by isolating fractions having a retention time of about 21.3 minutes (15.9 mg, 21.1% yield) which may have been isolated along with the enantiomer and/or one or more diastereomers. The stereochemistry of the title compound was confirmed by $^1$H-NMR nOe experiment), LC/MS (ES+APCI) m/z=384.1 (M+H).

Example 44

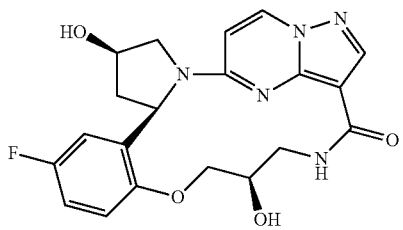 [SMILES: O=C1NC[C@@H](O)COc2ccc(F)cc2[C@H]2C[C@@H](O)CN2c2ccn3ncc1c3n2]

(4R,6R,15R)-9-fluoro-4,15-dihydroxy-13-oxa-2,17,21,22,25-pentaazapentacyclo[17.5.2.0$^{2,6}$.0$^{7,12}$.0$^{22,26}$]hexacosa-1(25),7(12),8,10,19(26),20,23-heptaen-18-one The title compound was prepared according to the method of Example 41, substituting (R)-1-amino-3-chloropropan-2-ol hydrochloride (prepared according to the procedure described in Example 19, Step A using (R)-2-(chloromethyl)oxirane) for (S)-1-amino-3-chloropropan-2-ol hydrochloride in Step A. The crude material was purified on a silica gel column, eluting with CH$_2$Cl$_2$ to NH$_4$OH:MeOH:CH$_2$Cl$_2$ (0.5:5:95) (4 runs). Fractions containing the earlier eluting compound were collected to provide 12 mg (10.9% yield) of the desired material. The stereochemistry of the title compound was confirmed by $^1$H-NMR nOe experiment. LC/MS (ES+APCI) m/z=414.0 (M+H).

Example 44-B

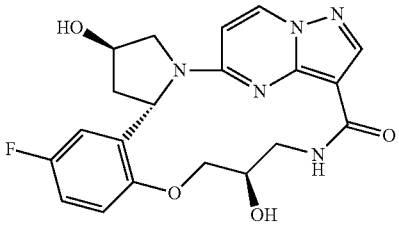 [SMILES: O=C1NC[C@@H](O)COc2ccc(F)cc2[C@@H]2C[C@@H](O)CN2c2ccn3ncc1c3n2]

(4R,6S,15R)-9-fluoro-4,5-dihydroxy-13-oxa-2,17,21,22,25-pentaazapentacyclo[17.5.2.0$^{2,6}$.0$^{7,12}$.0$^{22,26}$]hexacosa-1(25),7(12),8,10,19(26),20,23-heptaen-18-one The title compound was isolated during the purification reported in Example 44. Fractions containing the later eluting compound were collected to provide 15 mg (13.6% yield) of the title compound, which may have been isolated along with the enantiomer and/or one or more diastereomers. The stereochemistry of the title compound was confirmed by $^1$H-NMR nOe experiment); LC/MS (ES+APCI) m/z=414.1 (M+H).

Example 45

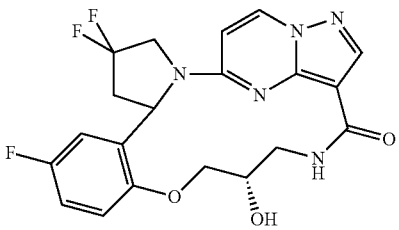 [SMILES: O=C1NC[C@H](O)COc2ccc(F)cc2C2CC(F)(F)CN2c2ccn3ncc1c3n2]

Diastereomer 1 and Diastereomer 2 of (15S)-4,4,9-trifluoro-15-hydroxy-13-oxa-2,17,21,22,25-pentaazapentacyclo[17.5.2.0$^{2,6}$.0$^{7,12}$.0$^{22,26}$]hexacosa-1(25),7(12),8,10,19(26),20,23-heptaen-18-one

Step A: Preparation of (R)-5-(5-fluoro-2-methoxyphenyl)pyrrolidin-3-ol hydrochloride To solution of (R)-tert-butyl 4-(tert-butyldimethylsilyloxy)-2-(5-fluoro-2-methoxyphenyl)pyrrolidine-1-carboxylate (1.01 g, 2.37 mmol) in CH$_2$Cl$_2$ (10 mL) at 0° C. was added 4M HCl in dioxane (5.93 mL, 23.7 mmol). The resulting mixture was warmed to ambient temperature and stirred for 8 hours. The reaction mixture was concentrated under reduced pressure to give the crude material that was triturated with ether. The resulting solids were filtered and dried under reduced pressure to afford (R)-5-(5-fluoro-2-methoxyphenyl)pyrrolidin-3-ol hydrochloride (0.577 g, 2.33 mmol, 98.2% yield). MS (APCI) m/z=212.0 (M+H).

Step B: Preparation of (R)-ethyl 5-(2-(5-fluoro-2-methoxyphenyl)-4-hydroxypyrrolidin-1-yl)pyrazolo[1,5-a]pyrimidine-3-carboxylate To a suspension of ethyl 5-hydroxypyrazolo[1,5-a]pyrimidine-3-carboxylate (0.541 g, 2.61 mmol) and BOP reagent (1.57 g, 3.56 mmol) in DMF/CH$_2$Cl$_2$ (3 mL/3 mL) at 0° C. was added (R)-5-(5-fluoro-2-methoxyphenyl)pyrrolidin-3-ol hydrochloride (0.588 g, 2.37 mmol) followed by DIEA (1.66 mL, 9.50 mmol). The resulting mixture was warmed to ambient temperature and stirred for 18 hours. The reaction mixture was concentrated under reduced pressure to give the crude material that was diluted again with EtOAc (30 mL). The organic layer was washed with saturated aqueous NaHCO$_3$ followed by brine, dried over MgSO$_4$, filtered, and concentrated under reduced pressure to give the crude material that was purified by silica gel flash column chromatography, eluting with CH$_2$Cl$_2$ to 5% MeOH in CH$_2$Cl$_2$ to afford (R)-ethyl 5-(2-(5-fluoro-2-methoxyphenyl)-4-hydroxypyrrolidin-1-yl)pyrazolo[1,5-a]pyrimidine-3-carboxylate (0.735 g, 1.84 mmol, 77.3% yield). LC/MS (ES+APCI) m/z=401.1 (M+H).

Step C: Preparation of ethyl 5-(2-(5-fluoro-2-methoxyphenyl)-4-oxopyrrolidin-1-yl)pyrazolo[1,5-a]pyrimidine-3-carboxylate To a suspension of Dess-Martin periodinane (0.233 g, 0.549 mmol) in CH$_2$Cl$_2$ (2.2 mL) at 0° C. was added a solution of (R)-ethyl 5-(2-(5-fluoro-2-methoxyphenyl)-4-hydroxypyrrolidin-1-yl)pyrazolo[1,5-a]pyrimidine-3-carboxylate (0.200 g, 0.499 mmol) in CH$_2$Cl$_2$ (1.5 mL). The resulting mixture was warmed to ambient temperature and stirred for 18 hours. The reaction mixture was cooled to 0° C. and quenched with saturated aqueous NaHCO$_3$ (5 mL) containing Na$_2$S$_2$O$_3$ (0.608 g, 3.85 mmol). The resulting mixture was warmed to ambient temperature and stirred for 10 minutes. The organic layer was separated, washed with saturated aqueous NaHCO$_3$ (10 mL) followed by brine (10 mL), dried over MgSO$_4$, filtered, and concentrated under reduced pressure to afford ethyl 5-(2-(5-fluoro-2-methoxyphenyl)-4-oxopyrrolidin-1-yl)pyrazolo[1,5-a]pyrimidine-3-carboxylate (0.164 g, 82.4% yield). LC/MS (ES+APCI) m/z=399.1 (M+H).

Step D: Preparation of ethyl 5-(4,4-difluoro-2-(5-fluoro-2-methoxyphenyl)pyrrolidin-1-yl)pyrazolo[1,5-a]pyrimidine-3-carboxylate To a solution of ethyl 5-(2-(5-fluoro-2-methoxyphenyl)-4-oxopyrrolidin-1-yl)pyrazolo[1,5-a]pyrimidine-3-carboxylate (0.162 g, 0.407 mmol) in CH$_2$Cl$_2$ (3 mL) was added a solution of bis(2-methoxyethyl)aminosulfur trifluoride (0.134 mL, 0.691 mmol) followed by EtOH (0.00475 mL, 0.0813 mmol). The resulting mixture was stirred at ambient temperature for 18 hours. The reaction mixture was poured into saturated aqueous NaHCO$_3$ (6 mL) and extracted with CH$_2$Cl$_2$ (2×10 mL). The combined organic layers were dried over MgSO$_4$, filtered, and concentrated under reduced pressure to give the crude material that was purified by silica column chromatography, eluting with 0-50% EtOAc/Hexanes to afford ethyl 5-(4,4-difluoro-2-(5-fluoro-2-methoxyphenyl)pyrrolidin-1-yl)pyrazolo[1,5-a]pyrimidine-3-carboxylate (0.126 g, 65.6% yield). MS (APCI) m/z=420.9 (M+H).

Step E: Preparation of 5-(4,4-difluoro-2-(5-fluoro-2-hydroxyphenyl)pyrrolidin-1-yl)pyrazolo[1,5-a]pyrimidine-3-carboxylic acid To a solution of ethyl 5-(4,4-difluoro-2-(5-fluoro-2-methoxyphenyl)pyrrolidin-1-yl)pyrazolo[1,5-a]pyrimidine-3-carboxylate (0.126 g, 0.267 mmol) in CH$_2$Cl$_2$ (1.3 mL) at 0° C. was added 1M BBr₃ in CH₂Cl₂ (1.50 mL, 1.50 mmol). The resulting mixture was warmed to ambient temperature and stirred for 18 hours. The reaction mixture was diluted with CH₂Cl₂ (5 mL) and poured into a mixture of ice and saturated aqueous NaHCO₃ (3 mL). The aqueous layer was then acidified to about pH 3 with 1N aqueous HCl. The aqueous layer was extracted with CH₂Cl₂ (3×10 mL). The combined organic layers were dried over MgSO₄, filtered, and concentrated under reduced pressure to give a mixture of ethyl 5-(4,4-difluoro-2-(5-fluoro-2-hydroxyphenyl)pyrrolidin-1-yl)pyrazolo[1,5-a]pyrimidine-3-carboxylate and 5-(4,4-difluoro-2-(5-fluoro-2-hydroxyphenyl)pyrrolidin-1-yl)pyrazolo[1,5-a]pyrimidine-3-carboxylic acid. This mixture was taken up in MeOH-THF (0.25 mL/0.75 mL) at ambient temperature, and 2N aqueous LiOH (0.667 mL, 1.33 mmol) was added. The resulting mixture was heated at 50° C. for 24 hours. The reaction mixture was cooled to ambient temperature and concentrated under reduced pressure to remove the organic solvents. The residue was diluted with 5 mL of EtOAc and acidified to pH 3 to 4 with 6N aqueous HCl with stirring. The organic layer was separated and the acidic aqueous layer was extracted with EtOAc (2×5 mL). The combined organic layers were dried over MgSO₄, filtered, and concentrated under reduced pressure to afford 5-(4,4-difluoro-2-(5-fluoro-2-hydroxyphenyl)pyrrolidin-1-yl)pyrazolo[1,5-a]pyrimidine-3-carboxylic acid (0.094 g, 93.1% yield). MS (APCI) m/z=378.9 (M+H).

Step F: Preparation of N—((S)-3-chloro-2-hydroxypropyl)-5-(4,4-difluoro-2-(5-fluoro-2-hydroxyphenyl)pyrrolidin-1-yl)pyrazolo[1,5-a]pyrimidin-3-carboxamide To a mixture of 5-(4,4-difluoro-2-(5-fluoro-2-hydroxyphenyl)pyrrolidin-1-yl)pyrazolo[1,5-a]pyrimidine-3-carboxylic acid (0.047 g, 0.124 mmol) and HOBT (0.0252 g, 0.186 mmol) in DMF (1 mL) at ambient temperature was added EDCI (0.0357 g, 0.186 mmol). The resulting mixture was stirred for 1 hour. To this mixture was added (S)-1-amino-3-chloropropan-2-ol hydrochloride (Example 19, Step A; 0.0218 g, 0.149 mmol) followed by DIEA (0.0656 mL, 0.373 mmol) at ambient temperature. The resulting mixture was stirred for 48 hours. The reaction mixture was diluted with EtOAc (10 mL), and the organic layer was washed with a 1:1 mixture of brine and water. The aqueous layer was separated and extracted with EtOAc (2×10 mL). The combined organic layers were washed with a 1:1 mixture of brine and water (15 mL) and combined with the organic layer obtained previously. The organic layer was dried over MgSO₄, filtered, and concentrated under reduced pressure to afford N—((S)-3-chloro-2-hydroxypropyl)-5-(4,4-difluoro-2-(5-fluoro-2-hydroxyphenyl)pyrrolidin-1-yl)pyrazolo[1,5-a]pyrimidine-3-carboxamide (0.061 g, 105% yield). LC/MS (ES+APCI) m/z=468.1 (M−H).

Step G: Preparation of Diastereomers 1 and 2 of (15S)-4,4,9-trifluoro-15-hydroxy-13-oxa-2,17,21,22,25-pentaazapentacyclo[17.5.2.0²,⁶.0⁷,¹².0²²,²⁶]hexacosa-1 (25),7 (12),8,10,19(26),20,23-heptaen-18-one A mixture of N—((S)-3-chloro-2-hydroxypropyl)-5-(4,4-difluoro-2-(5-fluoro-2-hydroxyphenyl)pyrrolidin-1-yl)pyrazolo[1,5-a]pyrimidine-3-carboxamide (0.060 g, 0.128 mmol) and Cs₂CO₃ (0.208 g, 0.639 mmol) in DMF (6.4 mL) was heated at 85° C. for 30 minutes. The reaction mixture was cooled to ambient temperature and filtered. The filtrate was concentrated under reduced pressure to give the crude material which was purified by silica gel flash column chromatography (CH₂Cl₂ to NH₄OH:MeOH:CH₂Cl₂=0.5:5:95) to afford a mixture of the diastereomers. The isolated diastereomers were further purified by chiral column chromatography (Chiral Tech OD-H column, 20% EtOH in hexanes). Fractions having a retention time of about 17.1 minutes were isolated to afford the title compound designated as Diastereomer 1 (11 mg, 20% yield; MS (APCI) m/z=434.2 (M+H). Fractions having a retention time of about 21.0 minutes were isolated to provide the title compound designated as Diastereomer 2 (13 mg; 24% yield); MS (APCI) m/z=434.2 (M+H).

What is claimed is:
1. A compound of Formula I

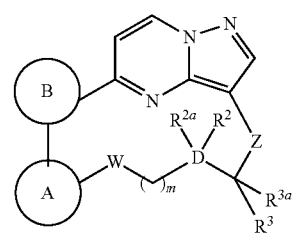

or pharmaceutically acceptable salts thereof, wherein:
ring A is selected from rings A-1 and A-2 having the structures:

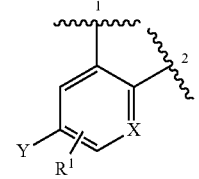

A-1

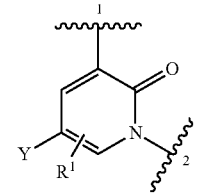

A-2 wherein the wavy line labeled 1 indicates the point of attachment of ring A to ring B and the wavy line labeled 2 indicates the point of attachment of ring A to W;
X is N or CH;
Y is H or F;
$R^1$ is H, (1-3C)alkyl, (1-3C)alkoxy or halogen;
B is B-1:

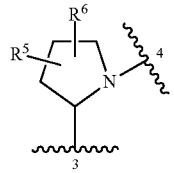

B-1 wherein the wavy line labeled 3 indicates the point of attachment to ring A and the wavy line labeled 4 indicates the point of attachment to the pyrazolo[1,5-a]pyrimidine ring of Formula I;
W is O, NH or $CH_2$, wherein when ring A is A-2, then W is $CH_2$;
m is 0, 1 or 2;
D is carbon, $R^2$ and $R^{2a}$ are independently H, F, (1-3C)alkyl or OH (provided that $R^2$ and $R^{2a}$ are not both OH), and $R^3$ and $R^{3a}$ are independently H, (1-3C)alkyl or hydroxy(1-3 C)alkyl;
Z is *—$NR^{4a}C(=O)$—, wherein the asterisk indicates the point of attachment of Z to the carbon bearing $R^3$;
$R^{4a}$ is H, (1-6C)alkyl, fluoro(1-6C)alkyl, difluoro(1-6C)alkyl, trifluoro(1-6C)alkyl, hydroxy(1-6C alkyl) or dihydroxy(2-6C alkyl); and
$R^5$ and $R^6$ are independently H, halogen, OH, (1-6C) alkyl or hydroxy(1-6C)alkyl.

2. The compound according to claim 1, wherein ring A is ring A-1 having the structure

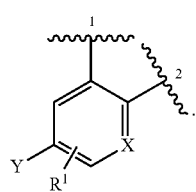

A-1

3. The compound according to claim 1, wherein ring A is ring A-2 having the structure

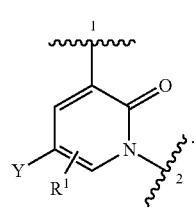

A-2

4. The compound of claim 1, wherein Y is F.
5. The compound of claim 1, wherein $R^1$ is H.
6. The compound of claim 1, wherein $R^{4a}$ is hydrogen.
7. The compound of claim 1, wherein $R^2$ and $R^{2a}$ are each hydrogen.
8. The compound of claim 1, wherein W is $CH_2$.
9. The compound of claim 1, wherein m is 0.
10. The compound of claim 1, wherein m is 1.
11. The compound of claim 1, selected from the group consisting of:
(6R)-9-fluoro-2,11,15,19,20,23-hexaazapentacyclo[15.5.2.1$^{7,11}$.0$^{2,6}$.0$^{20,24}$]pentacosa-1(23),7,9,17(24),18, 21-hexaene-16,25-dione;
(6R)-9-fluoro-13-oxa-2,11,17,21,22,25-hexaazapentacyclo[17.5.2.0$^{2,6}$.0$^{7,12}$.0$^{22,26}$]hexacosa-1(25),7,9,11,19 (26),20,23-heptaen-18-one;
(6R)-9-fluoro-15-hydroxy-13-oxa-2,11,17,21,22,25-hexaazapentacyclo[17.5.2.0$^{2,6}$.0$^{7,12}$.0$^{22,26}$]hexacosa-1(25),7,9,11,19(26),20,23-heptaen-18-one;
(6R,13S)-9-fluoro-13-hydroxy-2,11,15,19,20,23-hexaazapentacyclo-[15.5.2.1$^{7,11}$.0$^{2,6}$.0$^{20,24}$]pentacosa-1(23),7,9,17(24),18,21-hexaene-16,25-dione;
(6R,15R)-9-fluoro-15-hydroxy-13-oxa-2,11,17,21,22,25-hexaazapentacyclo-[17.5.2.0$^{2,6}$.0$^{7,12}$.0$^{22,26}$]hexacosa-1(25),7,9,11,19(26),20,23-heptaen-18-one;
(6R,13R)-9-fluoro-13-hydroxy-2,11,15,19,20,23-hexaazapentacyclo-[15.5.2.1$^{7,11}$.0$^{2,6}$.0$^{20,24}$]pentacosa-1(23),7,9,17(24),18,21-hexaene-16,25-dione;
(6R)-9-fluoro-13-oxa-2,11,16,20,21,24-hexaazapentacyclo[16.5.2.0$^{2,6}$.0$^{7,12}$.0$^{21,25}$]pentacosa-1(24),7, 9,11,18 (25),19,22-heptaen-17-one;
(6R)-9-fluoro-13-oxa-2,11,18,22,23,26-hexaazapentacyclo[18.5.2.0$^{2,6}$.0$^{7,12}$.0$^{23,27}$]heptacosa-1(26),7,9,11,20 (27),21,24-heptaen-19-one;
(6R)-9-fluoro-2,11,16,20,21,24-hexaazapentacyclo [16.5.2.1$^{7,11}$.0$^{2,6}$.0$^{21,25}$]hexacosa-1(24),7,9,18(25),19, 22-hexaene-17,26-dione;
(6R)-9-fluoro-2,11,13,16,20,21,24-heptaazapentacyclo [16.5.2.0$^{2,6}$.0$^{7,12}$.0$^{21,25}$]pentacosa-1(24),7,9,11,18(25), 19,22-heptaen-17-one;
(6R)-9-fluoro-2,11,13,17,21,22,25-heptaazapentacyclo [17.5.2.0$^{2,6}$.0$^{7,12}$.0$^{22,26}$]hexacosa-1(25),7,9,11,19(26), 20,23-heptaen-18-one;
(6R)-9-fluoro-14-oxa-2,11,18,19,22-pentaazapentacyclo [14.5.2.1$^{7,11}$.0$^{2,6}$.0$^{19,23}$]tetracosa-1(22),7,9,16(23),17, 20-hexaene-15,24-dione;
(6R,13R)-9,13-difluoro-2,11,15,19,20,23-hexaazapentacyclo[15.5.2.1$^{7,11}$.0$^{2,6}$.0$^{20,24}$]pentacosa-1(23), 7,9,17 (24),18,21-hexaene-16,25-dione;
(6R)-9-fluoro-17-methyl-13-oxa-2,11,17,21,22,25-hexaazapentacyclo[17.5.2.0$^{2,6}$.0$^{7,12}$.0$^{22,26}$]hexacosa-1 (25),7,9,11,19(26),20,23-heptaen-18-one;
(6R)-9,15,15-trifluoro-13-oxa-2,11,17,21,22,25-hexaazapentacyclo[17.5.2.0$^{2,6}$.0$^{7,12}$.0$^{22,26}$]hexacosa-1(25),7,9, 11,19(26),20,23-heptaen-18-one;
(6R)-9-fluoro-2,11,16,20,21,24-hexaazapentacyclo [16.5.2.0$^{2,6}$.0$^{7,12}$.0$^{21,25}$]pentacosa-1(24),7,9,11,18(25), 19,22-heptaen-17-one;
(6R)-9-fluoro-15-methyl-2,11,16,20,21,24-hexaazapentacyclo[16.5.2.0$^{2,6}$.0$^{7,12}$.0$^{21,25}$]pentacosa-1(24),7,9,11, 18(25),19,22-heptaen-17-one;
(6R,13R)-9-fluoro-13-methyl-2,11,15,19,20,23-hexaazapentacyclo[15.5.2.1$^{7,11}$.0$^{2,6}$.0$^{20,24}$]pentacosa-1(23),7,9, 17(24),18,21-hexaene-16,25-dione;
(6R,13S)-9-fluoro-13-methyl-2,11,15,19,20,23-hexaazapentacyclo [15.5.2.1$^{7,11}$.0$^{2,6}$.0$^{20,24}$]pentacosa-1(23),7, 9,17(24),18,21-hexaene-16,25-dione;
(6R)-9-fluoro-15,15-dimethyl-13-oxa-2,11,17,21,22,25-hexaazapentacyclo [17.5.2.0$^{2,6}$.0$^{7,12}$.0$^{22,26}$]hexacosa-1 (25),7,9,11,19(26),20,23-heptaen-18-one;
(6R)-9-fluoro-15,15-dimethyl-2,11,16,20,21,24-hexaazapentacyclo[16.5.2.0$^{2,6}$.0$^{7,12}$.0$^{21,25}$]pentacosa-1(24),7, 9,11,18(25),19,22-heptaen-17-one; and
(6R)-9-fluoro-13,13-dimethyl-2,11,15,19,20,23-hexaazapentacyclo[15.5.2.1$^{7,11}$.0$^{2,6}$.0$^{20,24}$]pentacosa-1(23),7,9, 17(24),18,21-hexaene-16,25-dione; or a pharmaceutically acceptable salt thereof.

12. The compound of claim 1, selected from:
(6R)-9-fluoro-13-oxa-2,11,17,21,22,25-hexaazapentacyclo[17.5.2.0$^{2,6}$.0$^{7,12}$.0$^{22,26}$]hexacosa-1(25),7,9,11,19 (26),20,23-heptaen-18-one;
(6R)-9-fluoro-15-hydroxy-13-oxa-2,11,17,21,22,25-hexaazapentacyclo[17.5.2.0$^{2,6}$.0$^{7,12}$.0$^{22,26}$]hexacosa-1 (25),7,9,11,19(26),20,23-heptaen-18-one;
(6R,15R)-9-fluoro-15-hydroxy-13-oxa-2,11,17,21,22,25-hexaazapentacyclo-[17.5.2.0$^{2,6}$.0$^{7,12}$.0$^{22,26}$]hexacosa-1 (25),7,9,11,19(26),20,23-heptaen-18-one;

(6R)-9-fluoro-13-oxa-2,11,16,20,21,24-hexaazapentacyclo[16.5.2.0$^{2,6}$.0$^{7,12}$.0$^{21,25}$]pentacosa-1(24),7, 9,11,18(25),19,22-heptaen-17-one;

(6R)-9-fluoro-13-oxa-2,11,18,22,23,26-hexaazapentacyclo[18.5.2.0$^{2,6}$.0$^{7,12}$.0$^{23,27}$]heptacosa-1(26),7,9,11,20(27),21,24-heptaen-19-one;

(6R)-9-fluoro-2,11,13,16,20,21,24-heptaazapentacyclo[16.5.2.0$^{2,6}$.0$^{7,12}$.0$^{21,25}$]pentacosa-1(24),7,9,11,18(25),19,22-heptaen-17-one;

(6R)-9-fluoro-2,11,13,17,21,22,25-heptaazapentacyclo[17.5.2.0$^{2,6}$.0$^{7,12}$.0$^{22,26}$]hexacosa-1(25),7,9,11,19(26),20,23-heptaen-18-one;

(6R)-9-fluoro-17-methyl-13-oxa-2,11,17,21,22,25-hexaazapentacyclo[17.5.2.0$^{2,6}$.0$^{7,12}$.0$^{22,26}$]hexacosa-1(25),7,9,11,19(26),20,23-heptaen-18-one;

(6R)-9,15,15-trifluoro-13-oxa-2,11,17,21,22,25-hexaazapentacyclo[17.5.2.0$^{2,6}$.0$^{7,12}$.0$^{22,26}$]hexacosa-1(25),7,9,11,19(26),20,23-heptaen-18-one;

(6R)-9-fluoro-2,11,16,20,21,24-hexaazapentacyclo[16.5.2.0$^{2,6}$.0$^{7,12}$.0$^{21,25}$]pentacosa-1(24),7,9,11,18(25),19,22-heptaen-17-one;

(6R)-9-fluoro-15-methyl-2,11,16,20,21,24-hexaazapentacyclo[16.5.2.0$^{2,6}$.0$^{7,12}$.0$^{21,25}$]pentacosa-1(24),7,9,11,18(25),19,22-heptaen-17-one;

(6R)-9-fluoro-15,15-dimethyl-13-oxa-2,11,17,21,22,25-hexaazapentacyclo [17.5.2.0$^{2,6}$.0$^{7,12}$.0$^{22,26}$]hexacosa-1(25),7,9,11,19(26),20,23-heptaen-18-one; and (6R)-9-fluoro-15,15-dimethyl-2,11,16,20,21,24-hexaazapentacyclo[16.5.2.0$^{2,6}$.0$^{7,12}$.0$^{21,25}$]pentacosa-1(24),7,9,11,18(25),19,22-heptaen-17-one;

or a pharmaceutically acceptable salt thereof.

13. The compound of claim 1, selected from:

(6R)-9-fluoro-2,11,15,19,20,23-hexaazapentacyclo[15.5.2.1$^{7,11}$.0$^{2,6}$.0$^{20,24}$]pentacosa-1(23),7,9,17(24),18,21-hexaene-16,25-dione;

(6R,13S)-9-fluoro-13-hydroxy-2,11,15,19,20,23-hexaazapentacyclo-[15.5.2.1$^{7,11}$.0$^{2,6}$.0$^{20,24}$]pentacosa-1(23),7,9,17(24),18,21-hexaene-16,25-dione;

(6R,13R)-9-fluoro-13-hydroxy-2,11,15,19,20,23-hexaazapentacyclo-[15.5.2.1$^{7,11}$.0$^{2,6}$.0$^{20,24}$]pentacosa-1(23),7,9,17(24),18,21-hexaene-16,25-dione;

(6R)-9-fluoro-2,11,16,20,21,24-hexaazapentacyclo[16.5.2.1$^{7,11}$.0$^{2,6}$.0$^{21,25}$]hexacosa-1(24),7,9,18(25),19,22-hexaene-17,26-dione;

(6R)-9-fluoro-14-oxa-2,11,18,19,22-pentaazapentacyclo[14.5.2.1$^{7,11}$.0$^{2,6}$.0$^{19,23}$]tetracosa-1(22),7,9,16(23),17,20-hexaene-15,24-dione;

(6R,13R)-9,13-difluoro-2,11,15,19,20,23-hexaazapentacyclo[15.5.2.1$^{7,11}$.0$^{2,6}$.0$^{20,24}$]pentacosa-1(23),7,9,17(24),18,21-hexaene-16,25-dione;

(6R,13R)-9-fluoro-13-methyl-2,11,15,19,20,23-hexaazapentacyclo[15.5.2.1$^{7,11}$.0$^{2,6}$.0$^{20,24}$]pentacosa-1(23),7,9,17(24),18,21-hexaene-16,25-dione;

(6R,13S)-9-fluoro-13-methyl-2,11,15,19,20,23-hexaazapentacyclo[15.5.2.1$^{7,11}$.0$^{2,6}$.0$^{20,24}$]pentacosa-1(23),7,9,17(24),18,21-hexaene-16,25-dione; and (6R)-9-fluoro-13,13-dimethyl-2,11,15,19,20,23-hexaazapentacyclo[15.5.2.1$^{7,11}$.0$^{2,6}$.0$^{20,24}$]pentacosa-1(23),7,9,17(24),18,21-hexaene-16,25-dione; or a pharmaceutically acceptable salt thereof.

14. A pharmaceutical composition, which comprises a compound of Formula I

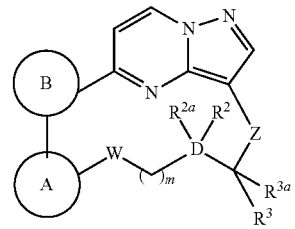

I or pharmaceutically acceptable salts thereof, wherein:
ring A is selected from rings A-1 and A-2 having the structures:

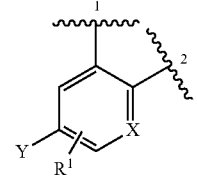

A-1

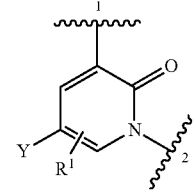

A-2 wherein the wavy line labeled 1 indicates the point of attachment of ring A to ring B and the wavy line labeled 2 indicates the point of attachment of ring A to W;
X is N or CH;
Y is H or F;
$R^1$ is H, (1-3C)alkyl, (1-3C)alkoxy or halogen;
B is B-1:

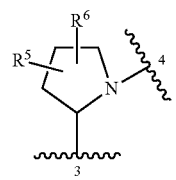

B-1 wherein the wavy line labeled 3 indicates the point of attachment to ring A and the wavy line labeled 4 indicates the point of attachment to the pyrazolo[1,5-a]pyrimidine ring of Formula I;
W is O, NH or CH$_2$, wherein when ring A is A-2, then W is CH$_2$;
m is 0, 1 or 2;
D is carbon, $R^2$ and $R^{2a}$ are independently H, F, (1-3C)alkyl or OH (provided that $R^2$ and $R^{2a}$ are not both OH), and $R^3$ and $R^{3a}$ are independently H, (1-3C)alkyl or hydroxy(1-3 C)alkyl;
Z is *—NR$^{4a}$C(=O)—, wherein the asterisk indicates the point of attachment of Z to the carbon bearing $R^3$;

$R^{4a}$ is H, (1-6C)alkyl, fluoro(1-6C)alkyl, difluoro(1-6C)alkyl, trifluoro(1-6C)alkyl, hydroxy(1-6C alkyl) or dihydroxy(2-6C alkyl); and $R^5$ and $R^6$ are independently H, halogen, OH, (1-6C)alkyl or hydroxy(1-6C)alkyl; and a pharmaceutically acceptable diluent or carrier.

* * * * *

UNITED STATES PATENT AND TRADEMARK OFFICE
CERTIFICATE OF CORRECTION

PATENT NO. : 9,493,476 B2
APPLICATION NO. : 14/575663
DATED : November 15, 2016
INVENTOR(S) : Steven Wade Andrews et al.

Page 1 of 2

It is certified that error appears in the above-identified patent and that said Letters Patent is hereby corrected as shown below:

On the Title Page

Column 1, Line 1 (Name of the First Inventor), delete "W." and insert -- Wade --, therefor.

In the Specification

Column 21, Lines 52-62, replace " 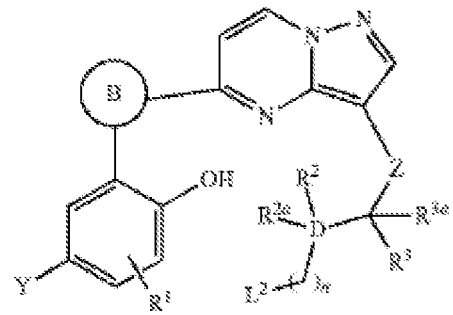 " with 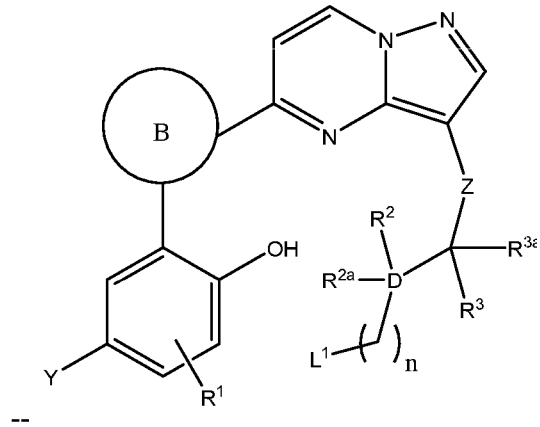 --, therefor.

Signed and Sealed this
Thirty-first Day of January, 2017

Michelle K. Lee
*Director of the United States Patent and Trademark Office*

CERTIFICATE OF CORRECTION (continued)
U.S. Pat. No. 9,493,476 B2

Column 77, Lines 12-22, replace " 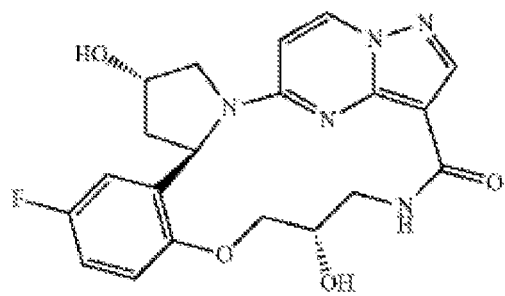 " with 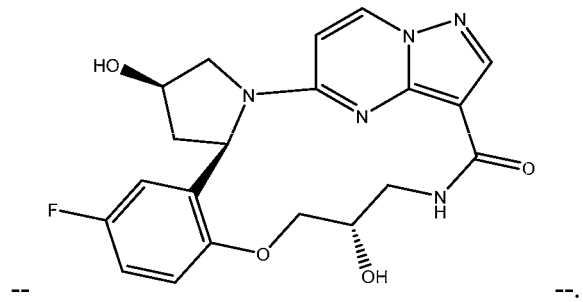 --.

In the Claims

Column 86, Line 27, in Claim 11, delete "(23), 7,9,17" and insert -- (23),7,9,17 --, therefor.

Column 86, Lines 45-46, in Claim 11, delete "hexaazapentacyclo [15" and insert -- hexaazapentacyclo[15 --, therefor.

Column 86, Line 49, Claim 11, delete "hexaazapentacyclo [17" and insert -- hexaazapentacyclo[17 --, therefor.

Column 87, Line 27, in Claim 12, delete "hexaazapentacyclo [17" and insert -- hexaazapentacyclo[17 --, therefor.